United States Patent
Freichels et al.

(10) Patent No.: US 11,618,769 B2
(45) Date of Patent: Apr. 4, 2023

(54) ANTIBODY PURIFICATION

(71) Applicant: BIO-SOURCING S.A., Liège (BE)

(72) Inventors: Régine Freichels, Angleur (BE); Olivier Favre-Bulle, Saint-Cloud (FR); François Côte, Hogne (BE); Bertrand Mérot, Brussels (BE)

(*) Notice: Subject to any disclaimer, the term of this patent is extended or adjusted under 35 U.S.C. 154(b) by 345 days.

(21) Appl. No.: 16/763,863

(22) PCT Filed: Nov. 13, 2018

(86) PCT No.: PCT/EP2018/081060
§ 371 (c)(1),
(2) Date: May 13, 2020

(87) PCT Pub. No.: WO2019/096777
PCT Pub. Date: May 23, 2019

(65) Prior Publication Data
US 2020/0283473 A1    Sep. 10, 2020

(30) Foreign Application Priority Data

Nov. 14, 2017   (EP) .................... 17201536

(51) Int. Cl.
C07K 1/22        (2006.01)
C07K 16/04       (2006.01)
C07K 16/18       (2006.01)

(52) U.S. Cl.
CPC ............. C07K 1/22 (2013.01); C07K 16/04 (2013.01); C07K 16/18 (2013.01); *C07K 2317/12* (2013.01)

(58) Field of Classification Search
None
See application file for complete search history.

(56) References Cited

U.S. PATENT DOCUMENTS

| 4,644,056 A * | 2/1987 | Kothe ............... A61P 31/04 530/832 |
| 2004/0162414 A1 | 8/2004 | Santora et al. |
| 2013/0197197 A1 | 8/2013 | Eckermann et al. |

FOREIGN PATENT DOCUMENTS

| EP | 1614693 A1 | 1/2006 |
| WO | 2010127069 A1 | 11/2010 |
| WO | 2011038894 A1 | 4/2011 |
| WO | 2015186004 A2 | 12/2015 |
| WO | 2016034726 A1 | 3/2016 |

OTHER PUBLICATIONS

Ahuja, Satinder. "Bioseparations: An overview", REFEREX, Feb. 1, 2000 (Feb. 1, 2000), XP040425626. p. 550, p. 580, pp. 575-581.
Echelard, Yann et al. "Transgenic Technology: a Validated Approach for Large-Scale Manufacturing." (XP055131254) Innovations in Pharmaceutical Technology, vol. 29 (Jul. 1, 2009): 50-54.
PCT International Search Report and Written Opinion; Application No. PCT/EP2018/081060 Bio-Sourcing S.A., International Filing date Nov. 13, 2018, Authorized Officer Maria Siaterli, dated Jan. 30, 2019, 12 pages.
Pollock, Daniel P , et al. "Transgenic Milk as a Method for the Production of Recombinant Antibodies." Journal of Immunological Methods, vol. 231, No. 1-2, 1999, pp. 147-157.
Yao, Hongqiang, et al. "Purification and Quantification of Heavy-Chain Antibodies from the Milk of Bactrian Camels." Animal Science Journal, vol. 88, No. 9, 2017, pp. 1446-1450.

* cited by examiner

*Primary Examiner* — Nora M Rooney
(74) *Attorney, Agent, or Firm* — Patent Law Works LLP

(57) ABSTRACT

The present invention relates to methods for purifying heterologous antibodies from caprine milk, such as goat milk. The present invention includes protein A based affinity chromatography to obtain purified transgenically expressed antibodies, in particular concentrates free from endogenous caprine antibodies.

14 Claims, 62 Drawing Sheets

L. Protein standard
1. Eluate fraction n°2 – purolite
2. Eluate fraction n°3 – purolite
3. Eluate fraction n°4 – purolite
4. Eluate fraction n°5 – purolite
5. Eluate fraction n°6 – purolite
6. Eluate fraction n°7 – purolite
7. Eluate fraction n°8 – purolite
8. Eluate fraction n°9 – purolite
9. Eluate fraction n°10 – purolite
10. Eluate fraction n°11 – purolite

FIGURE 15C
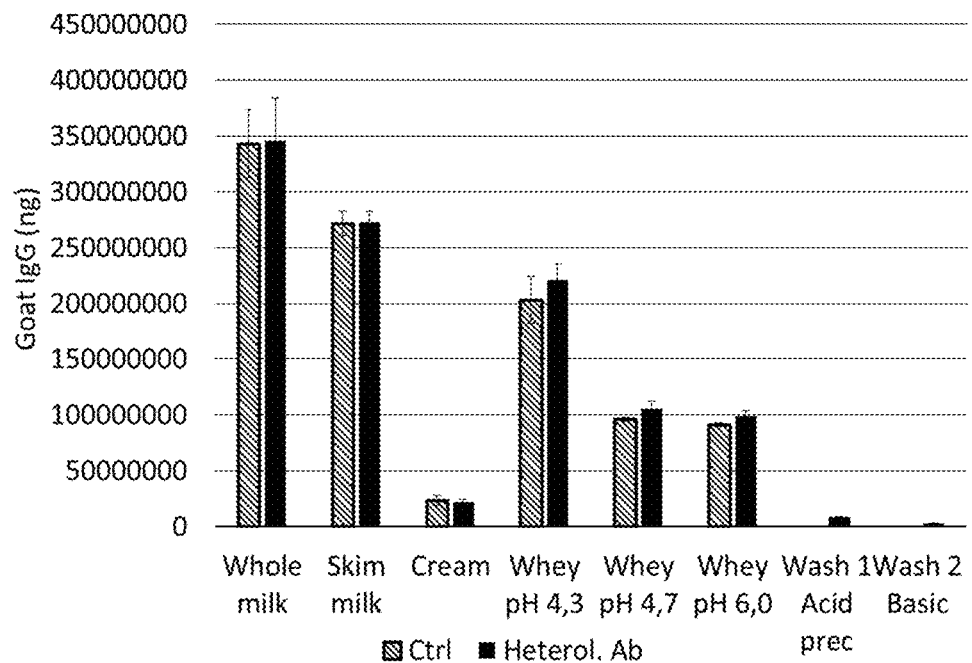
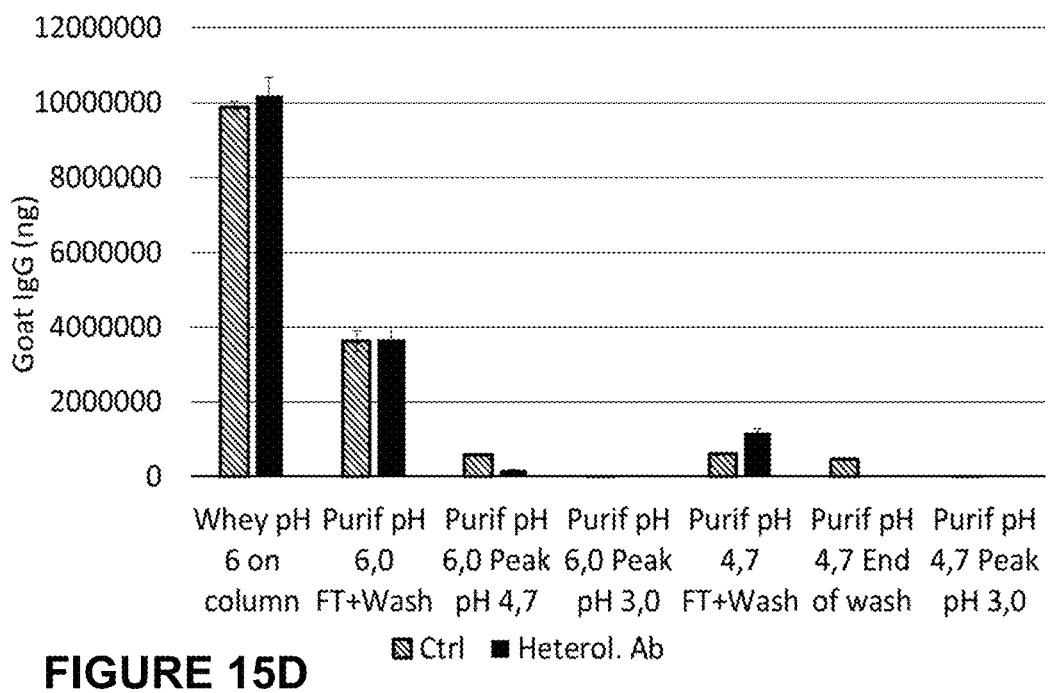
FIGURE 15D

Figure 19D
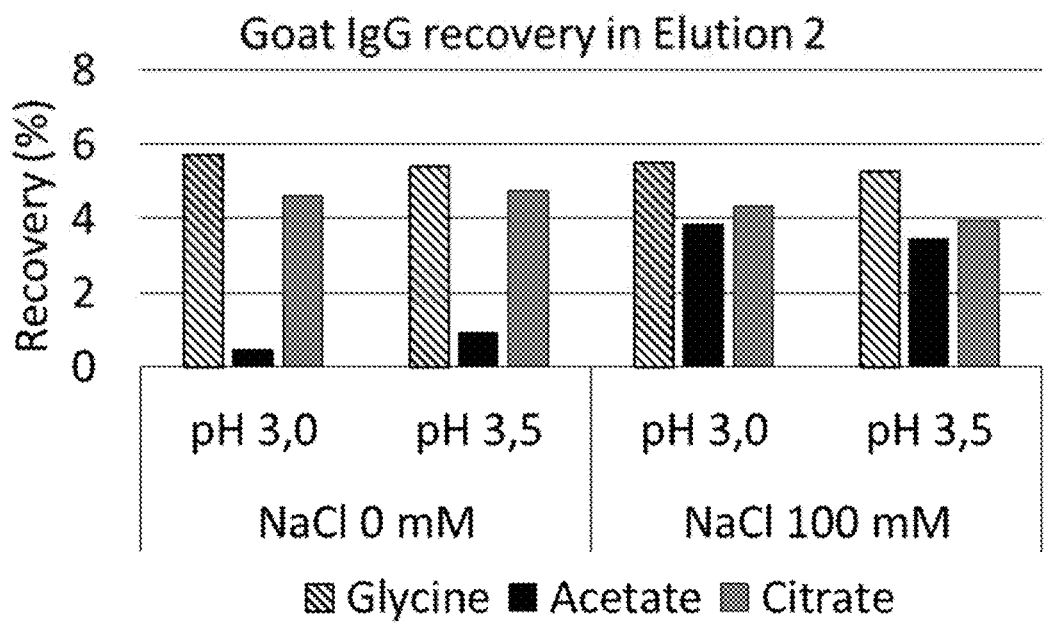
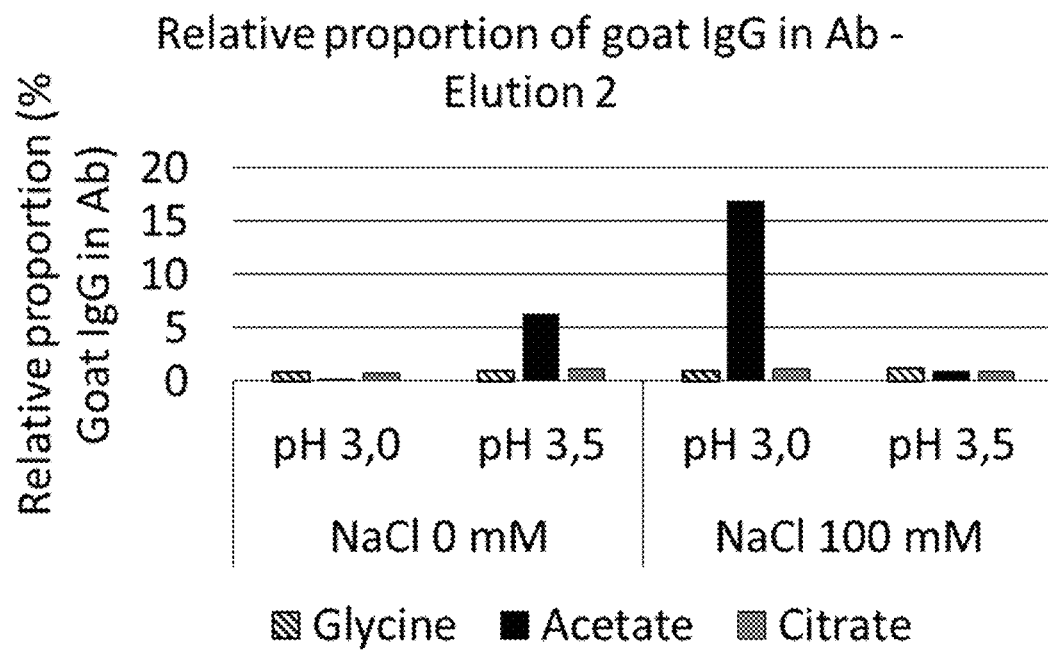
Figure 19E

ANTIBODY PURIFICATION

CROSS-REFERENCE TO RELATED APPLICATIONS

This application is a national phase entry under 35 U.S.C. § 371 of International Patent Application PCT/EP2018/081060, filed Nov. 13, 2018, designating the United States of America and published in English as International Patent Publication WO 2019/096777 on May 23, 2019, which claims the benefit under Article 8 of the Patent Cooperation Treaty to European Patent Application Serial No. 17201536.4, filed Nov. 14, 2017, the disclosure of each of which is hereby incorporated herein in its entirety by this reference.

FIELD OF THE INVENTION

The present invention relates to purification of antibodies, in particular recombinant monoclonal antibodies which are transgenically expressed and secreted in mammalian milk, such as goat milk.

BACKGROUND OF THE INVENTION

Antibodies have been since long used in research and are widely used in diagnostics, and more recently as therapeutic or theranostic agents. Research usage of antibodies includes mainly detection of particular antigens, such as for instance Western blotting, immunohistochemistry, flow cytometry, etc, or alternatively may involve isolation of particular antigens. Diagnostics similarly rely on detection of antigens, such as disease-specific antigens, including pathogenic antigens, but also self-antigens, for instance correlated with cancer or autoimmune diseases. Over the last decades, therapeutic antibodies have gained importance. A plethora of therapeutic antibodies are currently on the market. These antibodies mainly serve to interfere with particular antigen functionalities, such as including neutralizing effects of the antibodies, but alternatively may be involved in modulating the immune system, such as inducing or suppressing particular immune responses.

In 2014, monoclonal antibodies (mAbs) represented more than 20% of the new molecules placed on the market. Whereas polyclonal antibodies are relatively straightforward to produce, the production of monoclonal antibodies, in particular in sufficient quantities to meet these days' demands, including therapeutic usage, is more cost and labour intensive. While monoclonal antibodies typically originate from hybridomas, large scale production often involves isolating the antibody encoding sequences and recombinantly expressing the antibodies in heterologous systems. The most straightforward antibody production systems involve cloning the antibody encoding sequences in bacteria, which may be gram positive bacteria or gram negative bacteria. An advantage of gram positive bacteria is that these lack an outer membrane, thereby facilitating secretion of the produced antibodies into the medium. A major disadvantage of antibody production in bacteria is the possible misfolding of the antibodies, as well as lack of solubility due to sequestration in inclusion bodies. Another disadvantage is that bacteria process proteins in general, and hence in particular recombinant antibodies, quite differently than eukaryotic organisms and cells. In particular, antibodies are glycosylated proteins, and functionality to some extent may depend on proper glycosylation (e.g. stability and kinetics, immune responses, etc.). Hence, absence of glycosylation or different glycosylation patterns such as observed in bacteria may detrimentally affect antibody functionality. For this reason, antibody production in eukaryotic systems has the advantage that glycosylation patterns more closely resemble natural glycosylation. While many different types of eukaryotic cells may be used for antibody production, including yeast or other fungi, protozoans, or insect cells; mammalian cells are currently most widely used at least for therapeutic antibody production.

In general however, antibodies are complex and difficult to produce. Their production costs can range from 100 to 1000 € per gram. In particular, large scale antibody production in for instance mammalian cells in vitro requires large investments in equipment as well as consumables. Furthermore, of particular importance in the production of therapeutic antibodies are yield and purity. While a higher cost may to some extent be acceptable when it comes to human health, therapeutic antibodies also have applications for animal health, where such cost may become unacceptable. To develop such therapeutic antibodies for large animals it is necessary to lower the cost of manufacture below 50 € per gram.

In recent years, alternative methods for antibody production have emerged through the generation of transgenic animals, capable of producing recombinant antibodies. In particular, recombinant antibodies expression and secretion of such antibodies in milk of mammalians, such as goats, has gained interest. While investment in the generation of the transgenic animals is sizable, once the transgenic animals are obtained, production costs of the antibodies are drastically reduced. An important cost however remains in the purification of the antibodies. Furthermore, significant drawbacks remain in yield and purity.

It is therefore an objective of the present invention to address one or more of these shortcomings. In particular, it is an aim of the present invention to provide a method for purifying (recombinant) antibodies, in particular therapeutic antibodies, from mammalian milk, such as goat milk, while meeting regulatory and economic requirements for marketing, in particular at minimal cost and/or with increased purity and/or with increased yield.

SUMMARY OF THE INVENTION

In an aspect, the invention relates to a method for isolating and/or purifying antibodies comprising
   (a) providing caprine whey, optionally skimmed caprine whey, comprising a heterologous antibody;
   (b) contacting said whey with a protein A containing matrix;
   (c) separating said protein A containing solid matrix from said whey; and
   (d) eluting said heterologous antibody from said protein A containing solid matrix.

In a further aspect, the invention relates to a method for isolating and/or purifying antibodies comprising
   (a) providing caprine milk, optionally skimmed caprine milk, comprising a heterologous antibody;
   (b) removing caseins from said milk so as to obtain whey;
   (c) contacting said whey with a protein A containing matrix;
   (d) separating said protein A containing solid matrix from said whey; and
   (e) eluting said heterologous antibody from said protein A containing solid matrix.

In a further aspect, the invention relates to a method for isolating and/or purifying antibodies comprising (a) providing caprine milk comprising a heterologous antibody;
(b) skimming said milk;
(c) removing caseins from said skimmed milk so as to obtain whey;
(d) contacting said whey with a protein A containing matrix;
(e) separating said protein A containing solid matrix from said whey; and
(f) eluting said heterologous antibody from said protein A containing solid matrix.

Advantageously, the methods of the present invention may involve chromatography for purifying antibodies. In certain embodiments, the methods of the present invention involve affinity chromatography. In certain embodiments, the methods involve column chromatography, such as column affinity chromatography. In certain embodiments, the methods involve packed bed (column) chromatography, such as packed bed (column) affinity chromatography. In certain embodiments, the methods of the invention involve continuous chromatography, such as continuous (packed bed column affinity) chromatography. In certain embodiments, the methods of the invention involve continuous packed bed (column) chromatography.

In certain embodiments, skimming the milk comprises removing lipids from said milk. In certain embodiments, skimming said milk comprises centrifugation. In certain embodiments, skimming said milk comprises heating said milk. In certain embodiments, skimming said milk comprises heating said milk prior to centrifugation. In certain embodiments, heating said milk comprises heating said milk to a temperature ranging from about 30° C. to about 60° C. it has been found that heating the milk improves fat removal and at the same time improves subsequent caseins precipitation.

In certain embodiments, caseins are removed from said (skimmed) milk and comprises caseins precipitation. In certain embodiments, caseins removal and/or precipitation comprises acid precipitation. In certain embodiments, caseins removal and/or precipitation comprises adjusting the pH to a pH ranging from about 3.5 to about 5.0. In certain embodiments, caseins are removed from said (skimmed) milk or (skimmed) whey by centrifugation. In certain embodiments, caseins are removed from said (skimmed) milk or (skimmed) whey by filtration. In certain embodiments, caseins are removed from said (skimmed) milk or (skimmed) whey by centrifugation and filtration.

In certain embodiments, skimming the milk is preformed prior to caseins removal. In certain embodiments, caseins removal is performed prior to skimming.

In certain embodiments, prior to contacting the (skimmed) milk or (skimmed) whey with the protein A containing matrix the pH of the milk/whey and/or protein A containing matrix is adjusted to a pH ranging between about 5.0 and 8.0.

In certain embodiments, elution of the heterologous antibody comprises adjusting the pH to a pH ranging from about 3.0 to about 5.0. In certain embodiments, elution of the heterologous antibody comprises adjusting the pH to a pH ranging from about 3.0 to about 4.5.

In certain embodiments, prior to elution of the heterologous antibody, the pH of the (skimmed) milk or (skimmed) whey with the protein A containing matrix is adjusted to a pH ranging from about 4.5 to about 5.0. At this pH levels, it has been found that residual endogenous caprine antibodies can be eluted from the matrix, and hence do not contaminate the subsequently eluted heterologous antibodies.

In certain embodiments, said heterologous antibody is a monoclonal antibody. In certain embodiments, said heterologous antibody is a recombinant antibody. In certain embodiments, said heterologous antibody is transgenically expressed in caprine milk. In certain embodiments, the heterologous antibody is not a caprine antibody. In certain embodiments, the heterologous antibody is a mammalian antibody. In certain embodiments, the heterologous antibody is a murine, bovine, porcine, canine, feline, rabbit, monkey, guinea pig, rat, or equine (including donkey and horse) antibody. In certain embodiments, the heterologous antibody is an IgG antibody. In certain embodiments, the heterologous antibody is not an IgM or IgA antibody. In certain embodiments, the heterologous antibody is a therapeutic antibody. In certain embodiments, the heterologous antibody is for veterinary use. in certain embodiments, said (skimmed) milk or (skimmed) whey comprises endogenous caprine antibodies.

BRIEF DESCRIPTION OF THE FIGURES

FIGS. 15A-15D: ELISA results of the process samples. Heterologous antibody (FIGS. 15A and B) and goat IgG (FIGS. 15C and 15D) recoveries are shown in ctrl versus milk with heterologous antibody at 0.1 g/l. Whey at pH 4.3 was separated in two parts, the first was adjusted at pH 4.7 and the second at pH 6.0 to perform both purifications, i.e with sample loading at either pH 4.7 or pH 6.0. Control: left bar; Heterologous antibody: right bar.

FIGS. 19A-19E: ELISA results—Purification optimization. Different elution buffers were tested to determine the optimum buffer. Heterologous antibody concentrations retrieved in flowthrough (FIG. 19C) and the 2 elutions (pH 4.8 (FIGS. 19A and 19C) and 3.5 or 3.0 (FIGS. 19B and 19D)) are presented in the graphs. A ratio of goat IgG/heterologous antibody was performed to identify the condition were the best separation was observed (FIG. 19E). Glycine buffer: left bar; Acetate buffer: middle bar; Citrate buffer: right bar.

FIGS. 35A and 345B: SDS-PAGE analysis (FIG. 35A) and corresponding canine western blot analysis (FIG. 35B) of the heterologous antibody purification (not reduced conditions). The description of the samples loaded is reported in Table 9.

DETAILED DESCRIPTION OF THE INVENTION

Figure 1:
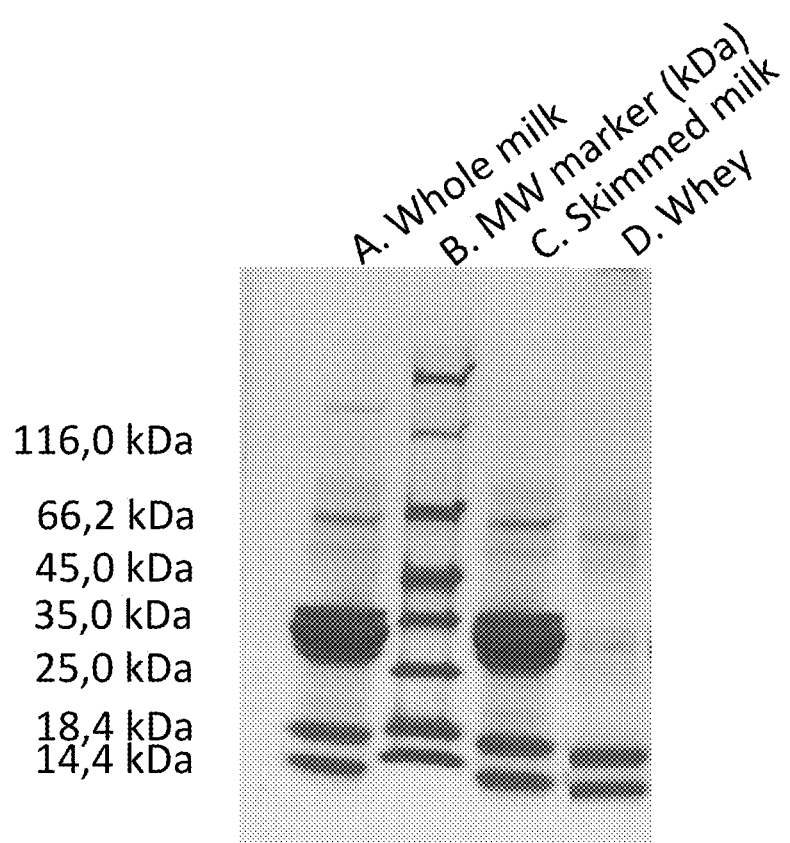
FIG. 1: SDS-PAGE analysis for milk samples. 10 µL of sample diluted 20 times were loaded on the gel. A. Whole milk. Whole milk contains mainly Caseins (MW 19 to 25 kDa), α-lactalbumin (MW≈18 kDa) and β-lactoglobulin (MW≈14 Kda). B. Pierce Unstained Protein Molecular Weight Marker (Thermo Scientific, Rockford, USA). C. Skimmed milk. Some proteins were removed during skimming (fat proteins). Caseins, α-lactalbumin and β-lactoglobulin are the main proteins in skimmed milk. D. Whey. Caseins are removed from skimmed milk to obtain whey.

Before the present system and method of the invention are described, it is to be understood that this invention is not limited to particular systems and methods or combinations described, since such systems and methods and combinations may, of course, vary. It is also to be understood that the terminology used herein is not intended to be limiting, since the scope of the present invention will be limited only by the appended claims.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. It will be appreciated that the terms "comprising", "comprises" and "comprised of" as used herein comprise the terms "consisting of", "consists" and "consists of", as well as the terms "consisting essentially of", "consists essentially" and "consists essentially of".

The recitation of numerical ranges by endpoints includes all numbers and fractions subsumed within the respective ranges, as well as the recited endpoints.

The term "about" or "approximately" as used herein when referring to a measurable value such as a parameter, an amount, a temporal duration, and the like, is meant to encompass variations of +/−20% or less, preferably +/−10% or less, more preferably +/−5% or less, and still more preferably +/−1% or less of and from the specified value, insofar such variations are appropriate to perform in the disclosed invention. It is to be understood that the value to which the modifier "about" or "approximately" refers is itself also specifically, and preferably, disclosed.

Whereas the terms "one or more" or "at least one", such as one or more or at least one member(s) of a group of members, is clear per se, by means of further exemplification, the term encompasses inter alia a reference to any one of said members, or to any two or more of said members, such as, e.g., any ≥3, ≥4, ≥5, ≥6 or ≥7 etc. of said members, and up to all said members.

All references cited in the present specification are hereby incorporated by reference in their entirety. In particular, the teachings of all references herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

In the following detailed description of the invention, reference is made to the accompanying drawings that form a part hereof, and in which are shown by way of illustration only of specific embodiments in which the invention may be practiced. It is to be understood that other embodiments may be utilised and structural or logical changes may be made without departing from the scope of the present invention. The following detailed description, therefore, is not to be taken in a limiting sense, and the scope of the present invention is defined by the appended claims.

Preferred statements (features) and embodiments of this invention are set herein below. Each statements and embodiments of the invention so defined may be combined with any other statement and/or embodiments unless clearly indicated to the contrary. In particular, any feature indicated as being preferred or advantageous may be combined with any other feature or features or statements indicated as being preferred or advantageous. Hereto, the present invention is in particular captured by any one or any combination of one or more of the below numbered aspects and embodiments 1 to 15, with any other statement and/or embodiments.

1. Method for purifying antibodies comprising
   (a) providing caprine whey, optionally skimmed caprine whey, comprising a heterologous antibody;
   (b) contacting said whey with a protein A containing matrix;
   (c) separating said protein A containing solid matrix from said whey; and
   (d) eluting said heterologous antibody from said protein A containing solid matrix.

2. The method according to statement 1, comprising
   (a) providing caprine milk, optionally skimmed caprine milk, comprising a heterologous antibody;
   (b) removing caseins from said milk so as to obtain whey;
   (c) contacting said whey with a protein A containing matrix;
   (d) separating said protein A containing solid matrix from said whey; and
   (e) eluting said heterologous antibody from said protein A containing solid matrix.

3. The method according to statement 1 or 2, comprising
   (a) providing caprine milk comprising a heterologous antibody;
   (b) skimming said milk;
   (c) removing caseins from said skimmed milk so as to obtain whey;
   (d) contacting said whey with a protein A containing matrix;
   (e) separating said protein A containing solid matrix from said whey; and
   (f) eluting said heterologous antibody from said protein A containing solid matrix.

4. The method according to any of statements 1 to 3, further comprising the step of eluting endogenous caprine antibodies prior to eluting said heterologous antibody, preferably at a pH ranging from 4.5 to 5.0.

5. The method according to any of statements 1 to 4, wherein said method comprises chromatography, preferably packed bed (column) chromatography.

6. The method according to any of statements 1 to 5, wherein said protein A solid matrix and/or said whey is equilibrated to a pH ranging from 5 to 8, preferably 6 to 7, before incubation with said whey.

7. The method according to any of statements 1 to 6, wherein eluting said heterologous antibody comprises adjusting the pH to a pH ranging from 3 to 5, preferably from 3.5 to 4.5.

8. The method according to any of statements 1 to 7, wherein said heterologous antibody is not a caprine antibody.

9. The method according to any of statements 1 to 8, wherein said heterologous antibody is an antibody for veterinary use.

10. The method according to any of statements 1 to 9, wherein said heterologous antibody is a murine, bovine, porcine, canine, feline, or equine antibody.

11. The method according to any of statements 1 to 10, wherein said heterologous antibody is an IgG antibody.

12. The method according to any of statements 1 to 11, wherein said heterologous antibody is a monoclonal antibody.

13. The method according to any of statements 1 to 12, wherein said whey comprises native endogenous caprine antibodies.

14. The method according to any of statements 2 to 13, wherein removing caseins comprises adjusting the pH to a pH ranging from 3.5 to 5.0, preferably 4.0 to 4.5, more preferably 4.3, followed by removing precipitated caseins, preferably by filtration and/or centrifugation.

15. The method according to any of statements 3 to 14, wherein skimming said milk comprises heating said milk to a temperature ranging from 30 to 60° C., preferably 45 to 55° C., followed by removing fat, preferably by centrifugation.

16. The method according to any of statements 1 to 15, wherein prior to eluting said heterologous antibody endogenous caprine antibodies are eluted.

17. The method according to statement 16, wherein said endogenous caprine antibodies are eluted at a pH which is higher than the pH for eluting said heterologous antibodies.

18. The method according to statement 16 or 17, wherein said endogenous caprine antibodies are eluted at a pH which is at least 0.1, preferably at least 0.3, more preferably at least 0.5, most preferably at least 1 higher than the pH for eluting said heterologous antibodies.

19. The method according to any of statements 16 to 18, wherein said endogenous caprine antibodies are eluted at a pH higher than or equal to 4.0, preferably higher than or equal to 4.3, more preferably higher than or equal to 4.5.

20. The method according to any of statements 16 to 19, wherein said endogenous caprine antibodies are eluted at a pH between 4.0 and 5.0, preferably between 4.3 and 5.0, more preferably between 4.5 and 5.0.

21. The method according to any of statements 16 to 20, wherein said heterologous antibody is eluted at a pH lower than or equal to 4.5, preferably lower than or equal to 4.3, more preferably higher than or equal to 4.0.

22. The method according to any of statements 16 to 21, wherein said heterologous antibody is eluted at a pH between 4.5 and 2.0, preferably between 4.3 and 2.0, more preferably between 4.0 and 2.0.

23. The method according to any of statements 16 to 23, wherein said endogenous caprine antibodies are eluted at a pH between 4.0 and 5.0, preferably between 4.3 and 5.0, more preferably between 4.5 and 5.0; wherein said heterologous antibody is eluted at a pH between 4.5 and 2.0, preferably between 4.3 and 2.0, more preferably between 4.0 and 2.0; and wherein said endogenous caprine antibodies are eluted at a pH which is at least 0.1, preferably at least 0.3, more preferably at least 0.5, most preferably at least 1 higher than the pH for eluting said heterologous antibodies.

24. The method according to any of statements 16 to 23, wherein said endogenous caprine antibodies are eluted at a pH between 4.0 and 5.0; wherein said heterologous antibody is eluted at a pH between 4.0 and 2.0.

25. The method according to any of statements 16 to 23, wherein said endogenous caprine antibodies are eluted at a pH between 4.3 and 5.0; wherein said heterologous antibody is eluted at a pH between 4.3 and 2.0.

26. The method according to any of statements 16 to 23, wherein said endogenous caprine antibodies are eluted at a pH between 4.5 and 5.0; wherein said heterologous antibody is eluted at a pH between 4.5 and 2.0.

The methods according to the invention aim at isolating and/or purifying antibodies from (skimmed) caprine milk or whey. The methods of the invention result in concentration of the antibodies and/or separation of the antibodies from other constituents of the milk or whey. In certain embodiments, the methods of the invention result in compositions having a protein content, wherein at least 80 wt % of the protein consists of the antibodies, in particular the heterologous antibodies. Preferably, at least 90 wt % of the protein consists of the antibodies, in particular the heterologous antibodies. More preferably, at least 95 wt % of the protein consists of the antibodies, in particular the heterologous antibodies. Even more preferably, at least 98 wt % of the protein consists of the antibodies, in particular the heterologous antibodies. Most preferably, at least 99 wt % of the protein consists of the antibodies, in particular the heterologous antibodies, such as 99.1, 99.2, 99.3, 99.4, 99.5, 99.6, 99.7, 99.8, 99.9, or more wt %, preferably at least 99.5 wt %, more preferably at least 99.9 wt %. In certain embodiments, the methods of the invention result in compositions wherein at least 80 wt % of the non-aqueous constituents or dry matter consists of the antibodies, in particular the heterologous antibodies. Preferably, at least 90 wt % of the non-aqueous constituents consists of the antibodies, in particular the heterologous antibodies. More preferably, at least 95 wt % of the non-aqueous constituents consists of the antibodies, in particular the heterologous antibodies. Even more preferably, at least 98 wt % of the non-aqueous constituents consists of the antibodies, in particular the heterologous antibodies, such as 98.5, 99.0, 99.5, or more wt %.

As used herein, the term "whey" has its ordinary meaning in the art. By means of further guidance, and without limitation, whey may be obtained by curdling milk and subsequent straining, filtration, or centrifugation. Essentially, curdling may entail coagulating or precipitating caseins. Alternatively, whey may be obtained by ultrafiltration, whereby caseins, in particular caseins micelles, are removed. Removal of (coagulated or precipitated) caseins results in whey. Curdling may involve addition of rennet (or an equivalent enzyme mixture) to the milk. Alternatively, curdling may involve adding acid to the milk. It will be understood that preferably substantially all caseins are removed in whey. In certain embodiments, less than 10 wt % caseins remain in the whey. Preferably less than 5 wt % caseins remain in the whey (based on the total mass of the whey or based on the total initial mass of caseins). More preferably, less than 3 wt % caseins remain in the whey. Most preferably, less than 1 wt % caseins remain in the whey. It will be understood that certain other components from the milk may equally be removed during or after curdling. For instance, a certain percentage of milk fats may be trapped in the curd and hence removed together with the precipitated or coagulated caseins. Similarly, a certain percentage of proteins other than caseins may similarly be precipitated or coagulated and hence remover together with the precipitated or coagulated caseins.

In certain embodiments, caseins are removed from the (skimmed) milk by coagulation, aggregation, or precipitation followed by straining, centrifugation, or filtration. In certain embodiments, caseins are removed from the (skimmed) milk by curdling or curding followed by straining, centrifugation, or filtration. In certain embodiments, caseins removal comprises acid caseins coagulation, precipitation, or aggregation. It has surprisingly found that acid precipitation yields superior results in terms of final purity and/or yield, compared to other methods of caseins precipitation and removal, such as calcium precipitation of ammonium sulphate precipitation. In certain embodiments, caseins are aggregated, coagulated, or precipitated by adjustment of the pH, preferably to a pH ranging from about 3.5 to about 5.0, such as 3.5, 3.6, 3.7, 3.8, 3.9, 4.0, 4.1, 4.2, 4.3, 4.4, 4.5, 4.6, 4.7, 4.8, 4.9, or 5.0. In certain embodiments, caseins are aggregated, coagulated, or precipitated by adjustment of the pH, preferably to a pH ranging from about 3.7 to about 4.8. In certain embodiments, caseins are aggregated, coagulated, or precipitated by adjustment of the pH, preferably to a pH ranging from about 3.9 to about 4.6. In certain embodiments, caseins are aggregated, coagulated, or precipitated by adjustment of the pH, preferably to a pH ranging from about 4.1 to about 4.4. In certain embodiments, caseins are aggregated, coagulated, or precipitated by adjustment of the pH, preferably to a pH of about 4.3. Adjustment of the pH may be performed with any acid, such as without limitation citric acid, HCl, acetic acid, sulfuric acid, nitric acid, carbonic acid, succinic acid, capric acid, propionic acid, pyruvic acid. Alternatively, rennet may also be used. The pH may be adjusted by adding the required amount of acid at once. Alternatively, the pH may be adjusted by adding the acid progressively. After the pH is adjusted, in certain embodiments the acidified (skimmed) milk or whey is immediately processed (i.e caseins removal). Alternatively, after the pH is adjusted, in certain embodiments the acidified (skimmed) milk or whey is incubated for a period of at least about 3 minutes, such as at least 4, 5, 6, 7, 8, 9, or 10 minutes. After the pH is adjusted, in certain embodiments the acidified (skimmed) milk or whey is incubated for at least about 3 minutes, such as a period ranging between about 3 minutes to about 120 minutes. After the pH is adjusted, in certain embodiments the acidified (skimmed) milk or whey is incubated for a period ranging between about 3 minutes to about 60 minutes. After the pH is adjusted, in certain embodiments the acidified (skimmed) milk or whey is incubated for a period ranging between about 3 minutes to about 30 minutes, such as 3, 4, 5, 6, 7, 8, 9, 10, 11, 12, 13, 14, 15, 16, 17, 18, 19, 20, 21, 22, 23, 24, 25, 26, 27, 28, 29, or 30 minutes. After the pH is adjusted, in certain embodiments the acidified (skimmed) milk or whey is incubated for a period ranging between about 5 minutes to about 20 minutes. After the pH is adjusted, in certain embodiments the acidified (skimmed) milk or whey is incubated for a period ranging between about 10 minutes to about 20 minutes. After the pH is adjusted, in certain embodiments the acidified (skimmed) milk or whey is incubated for a period of about 15 minutes. In certain embodiments, during this incubation, the temperature is maintained at a temperature ranging between about 20° C. to about 55° C., such as between about 20° C. to about 50° C. In certain embodiments, during this incubation, the temperature is maintained at a temperature ranging from about 20° C. to about 50° C.

In certain embodiments, during this incubation, the temperature is maintained at a temperature ranging from about 20° C. to about 45° C. In certain embodiments, during this incubation, the temperature is maintained at a temperature ranging from about 20° C. to about 40° C. In certain embodiments, during this incubation, the temperature is maintained at a temperature ranging from about 20° C. to about 35° C. In certain embodiments, during this incubation, the temperature is maintained at a temperature ranging from about 20° C. to about 30° C. In certain embodiments, during this incubation, the temperature is maintained at a temperature ranging from about 25° C. to about 60° C. In certain embodiments, during this incubation, the temperature is maintained at a temperature ranging from about 25° C. to about 55° C. In certain embodiments, during this incubation, the temperature is maintained at a temperature ranging from about 25° C. to about 50° C. In certain embodiments, during this incubation, the temperature is maintained at a temperature ranging from about 25° C. to about 45° C. In certain embodiments, during this incubation, the temperature is maintained at a temperature ranging from about 25° C. to about 40° C. In certain embodiments, during this incubation, the temperature is maintained at a temperature ranging from about 25° C. to about 35° C. In certain embodiments, during this incubation, the temperature is maintained at a temperature ranging from about 25° C. to about 30° C. In certain embodiments, during this incubation, the temperature is maintained at a temperature ranging from about 30° C. to about 60° C. In certain embodiments, during this incubation, the temperature is maintained at a temperature ranging from about 30° C. to about 55° C. In certain embodiments, during this incubation, the temperature is maintained at a temperature ranging from about 30° C. to about 50° C. In certain embodiments, during this incubation, the temperature is maintained at a temperature ranging from about 30° C. to about 45° C. In certain embodiments, during this incubation, the temperature is maintained at a temperature ranging from about 30° C. to about 40° C. In certain embodiments, during this incubation, the temperature is maintained at a temperature ranging from about 30° C. to about 35° C. In certain embodiments, during this incubation, the temperature is maintained at a temperature ranging from about 35° C. to about 60° C. In certain embodiments, during this incubation, the temperature is maintained at a temperature ranging from about 35° C. to about 55° C. In certain embodiments, during this incubation, the temperature is maintained at a temperature ranging from about 35° C. to about 50° C. In certain embodiments, during this incubation, the temperature is maintained at a temperature ranging from about 35° C. to about 45° C. In certain embodiments, during this incubation, the temperature is maintained at a temperature ranging from about 35° C. to about 40° C. In certain embodiments, during this incubation, the temperature is maintained at a temperature ranging from about 40° C. to about 60° C. In certain embodiments, during this incubation, the temperature is maintained at a temperature ranging from about 40° C. to about 55° C. In certain embodiments, during this incubation, the temperature is maintained at a temperature ranging from about 40° C. to about 50° C. In certain embodiments, during this incubation, the temperature is maintained at a temperature ranging from about 40° C. to about 45° C. In certain embodiments, during this incubation, the temperature is maintained at a temperature ranging from about 45° C. to about 60° C. In certain embodiments, during this incubation, the temperature is maintained at a temperature ranging from about 45° C. to about 55° C. In certain embodiments, during this incubation, the temperature is maintained at a temperature ranging from about 45° C. to about 50° C. In certain embodiments, during this incubation, the temperature is maintained at a temperature ranging from about 50° C. to about 60° C. In certain embodiments, during this incubation, the temperature is maintained at a temperature ranging from about 50° C. to about 55° C. Preferably, skimming the milk/whey is performed at a temperature ranging from 30° C. to 60° C. or from 30° C. to 55° C. or from 30° C. to 50° C. In certain embodiments, during this incubation, the temperature is maintained at the same temperature as the temperature during skimming. In certain embodiments, the temperature is maintained at room temperature.

Precipitated, aggregated, or coagulated caseins may be removed in certain embodiments by straining, centrifugation, or filtration. Removal of caseins may essentially be performed as is custom in the dairy industry. In certain embodiments, precipitated, aggregated, or coagulated caseins are removed by centrifugation. By means of example and without limitation, the (skimmed) milk or whey comprising precipitated, coagulated, or aggregated caseins may be centrifuged between about 3000 and 15000 g, such as between about 5000 and 13000 g, such as about 7000 g or 10000 g. In certain embodiments, the (skimmed) milk or whey comprising precipitated, coagulated, or aggregated caseins may be centrifuged for a period between 5 and 30 minutes, such as between 10 and 20 minutes, such as 15 minutes. In certain embodiments, precipitated, aggregated, or coagulated caseins are removed by filtration. Any type of filtration means may be used, including vacuum filtration, cross flow filtration, tangential flow filtration, granular bed filtration, pressure filtration, gravity filtration, microfiltration, ultrafiltration, etc. Preferred filtration includes pressure filtration. It will be understood that filtration membranes or media have a pore size adapted to separate the precipitated, aggregated, or coagulated caseins from the filtrate, i.e. the (skimmed) whey. By means of example, and without limitation, the pore size of the filtration membrane or medium may range between about 0.1 to about 5 µm, such as between about 0.2 to about 4 µm, between about 0.3 to about 3 µm, between about 0.3 to about 2 µm, between about 0.3 to about 1 µm, between about 0.2 to about 0.9 µm, between about 0.3 to about 0.8 µm, between about 0.3 to about 0.7 µm, between about 0.3 to about 0.6 µm, between about 0.4 to about 0.5 µm. The filter membrane or medium may have a pore size of about 0.45 µm. in certain embodiments, two separate filtration steps are included, such as for instance a first filtration step with a filter having a larger pore size (e.g. 1-3 µm), and a second filtration step with a filter having a smaller pore size (e.g. 0.1-1 µm).

In certain embodiments, the temperature at which caseins are removed during straining, filtration, or centrifugation may be the same as the temperature during prior acid incubation (i.e. elevated temperature, as described elsewhere). Alternatively, the temperature at which caseins are removed during straining, filtration, or centrifugation may be reduced, such as to room temperature, such as for instance ranging between 10 and 30° C., such as between 15 and 25° C.

As used herein, the term "skimmed" or "skimming" has its ordinary meaning in the art. By means of further guidance, and without limitation, skimming milk essentially relates to removal of fats from milk or whey. Hence, skimmed milk is defatted milk. Similarly, skimmed whey is defatted whey. In certain embodiments, skimmed milk or whey can be obtained by centrifugation or filtration, such as microfiltration, as a result of which fat separated from the rest of the milk constituents. Skimmed milk or whey may be obtained in separators or decreamers, as is known in the art. Skimming may essentially be performed as is custom in the dairy industry. By means of example, and without limitation, milk or whey may be centrifuged between 3000 and 10000 g, such as between 5000 and 9000 g, such as about 7000 g. In certain embodiments, the milk or whey may be centrifuged for a period between 5 and 20 minutes, such as between 10 and 20 minutes, such as 10 minutes. In certain embodiments of the present invention, milk is skimmed prior to caseins removal. In certain embodiments, milk is skimmed subsequent to caseins removal. In certain embodiments, the methods of the invention do not involve skimming the milk or whey, i.e. non-skimmed or non-defatted milk or whey is used in the methods of the invention. It will be understood that preferably substantially all fat is removed in the skimmed milk or whey. In certain embodiments, less than 10 wt % fat remains in the skimmed milk or whey (based on the total mass of the milk or whey after skimming or based on the total initial mass of fat). Preferably less than 5 wt % fat remains in the skimmed milk or whey. More preferably, less than 3 wt % fat remains in the skimmed milk or whey. Most preferably, less than 1 wt % fat remains, preferably less than 0.8 wt %, such as less than 0.6 wt % in the skimmed milk or whey. It will be understood that certain other components from the milk may equally be removed during or after skimming. For instance, a certain percentage of milk proteins or sugars, or alternatively certain fat soluble constituents may be removed during or after skimming. In certain embodiments, skimming equates defatting or decreaming or substantially defatting or decreaming. Preferably the pH of the milk prior to or during skimming is not altered compared to unprocessed caprine milk. In certain embodiments, the pH of the milk prior to and/or during skimming ranges from 6.0 to 7.0, such as from 6.3 to 6.7 or 6.4 to 6.8.

In certain embodiments, skimming the milk/whey is performed at an elevated temperature. In certain embodiments, skimming the milk/whey is performed at a temperature ranging from about 20° C. to about 65° C. In certain embodiments, skimming the milk/whey is performed at a temperature ranging from about 20° C. to about 60° C. In certain embodiments, skimming the milk/whey is performed at a temperature ranging from about 20° C. to about 55° C. In certain embodiments, skimming the milk/whey is performed at a temperature ranging from about 20° C. to about 50° C. In certain embodiments, skimming the milk/whey is performed at a temperature ranging from about 20° C. to about 45° C. In certain embodiments, skimming the milk/whey is performed at a temperature ranging from about 20° C. to about 40° C. In certain embodiments, skimming the milk/whey is performed at a temperature ranging from about 20° C. to about 35° C. In certain embodiments, skimming the milk/whey is performed at a temperature ranging from about 20° C. to about 30° C. In certain embodiments, skimming the milk/whey is performed at a temperature ranging from about 25° C. to about 65° C. In certain embodiments, skimming the milk/whey is performed at a temperature ranging from about 25° C. to about 60° C. In certain embodiments, skimming the milk/whey is performed at a temperature ranging from about 25° C. to about 55° C. In certain embodiments, skimming the milk/whey is performed at a temperature ranging from about 25° C. to about 50° C. In certain embodiments, skimming the milk/whey is performed at a temperature ranging from about 25° C. to about 45° C. In certain embodiments, skimming the milk/whey is performed at a temperature ranging from about 25° C. to about 40° C. In certain embodiments, skimming the milk/whey is performed at a temperature ranging from about 25° C. to about 35° C. In certain embodiments, skimming the milk/whey is performed at a temperature ranging from about 25° C. to about 30° C. In certain embodiments, skimming the milk/whey is performed at a temperature ranging from about 30° C. to about 65° C. In certain embodiments, skimming the milk/whey is performed at a temperature ranging from about 30° C. to about 60° C. In certain embodiments, skimming the milk/whey is performed at a temperature ranging from about 30° C. to about 55° C. In certain embodiments, skimming the milk/whey is performed at a temperature ranging from about 30° C. to about 50° C. In certain embodiments, skimming the milk/whey is performed at a temperature ranging from about 30° C. to about 45° C. In certain embodiments, skimming the milk/whey is performed at a temperature ranging from about 30° C. to about 40° C. In certain embodiments, skimming the milk/whey is performed at a temperature ranging from about 30° C. to about 35° C. In certain embodiments, skimming the milk/whey is performed at a temperature ranging from about 35° C. to about 65° C. In certain embodiments, skimming the milk/whey is performed at a temperature ranging from about 35° C. to about 60° C. In certain embodiments, skimming the milk/whey is performed at a temperature ranging from about 35° C. to about 55° C. In certain embodiments, skimming the milk/whey is performed at a temperature ranging from about 35° C. to about 50° C. In certain embodiments, skimming the milk/whey is performed at a temperature ranging from about 35° C. to about 45° C. In certain embodiments, skimming the milk/whey is performed at a temperature ranging from about 35° C. to about 40° C. In certain embodiments, skimming the milk/whey is performed at a temperature ranging from about 40° C. to about 65° C. In certain embodiments, skimming the milk/whey is performed at a temperature ranging from about 40° C. to about 60° C. In certain embodiments, skimming the milk/whey is performed at a temperature ranging from about 40° C. to about 55° C. In certain embodiments, skimming the milk/whey is performed at a temperature ranging from about 40° C. to about 50° C. In certain embodiments, skimming the milk/whey is performed at a temperature ranging from about 40° C. to about 45° C. In certain embodiments, skimming the milk/whey is performed at a temperature ranging from about 45° C. to about 65° C. In certain embodiments, skimming the milk/whey is performed at a temperature ranging from about 45° C. to about 60° C. In certain embodiments, skimming the milk/whey is performed at a temperature ranging from about 45° C. to about 55° C. In certain embodiments, skimming the milk/whey is performed at a temperature ranging from about 45° C. to about 50° C. In certain embodiments, skimming the milk/whey is performed at a temperature ranging from about 50° C. to about 65° C. In certain embodiments, skimming the milk/whey is performed at a temperature ranging from about 50° C. to about 60° C. In certain embodiments, skimming the milk/whey is performed at a temperature ranging from about 50° C. to about 55° C. Preferably, skimming the milk/whey is performed at a temperature ranging from 20° C. to 65° C. or from 30° C. to 60° C. or from 30° C. to 55° C. or from 30° C. to 50° C.

In certain embodiments, the milk is cooled after centrifugation and before fat removal to help solidify fats and hence help to remove the fat layer.

In certain embodiments, caprine milk or whey is stored prior to skimming or removal of caseins. Storage may include storage for about between several hours to about several days or weeks. In certain embodiments, storage is performed at reduced temperatures, e.g. temperatures below room temperature, such as temperatures ranging from about −40° C. to about 15° C., such as temperatures ranging from about −30° C. to about −10° C. or temperatures ranging from about 1° C. to about 10° C. For instance, caprine milk or whey may be frozen (e.g. −40° C. to −10° C.) up to 6 months, such as up to 5, 4, 3, 2, 1 or less months. For instance, caprine milk or whey may be refrigerated (e.g. 1° C. to 10° C.) up to 2 weeks, such as up to 1 or less weeks. Prior to skimming or caseins removal, the temperature of the milk/whey may be adjusted to the appropriate temperature as discussed herein elsewhere.

As used herein, "caprine" relates to a member of the bovidae subfamily caprinae. By means of example, the subfamily caprinae includes the tribe Ovibovini, including the genus Budocras, including Takin (*Budorcas taxicolor*), and the genus *Ovibos*, including Muskox (*Ovibos moschatus*); the tribe Caprini, including the genus *Ammotragus*, including Barbary sheep (*Ammotragus lervia*), the genus *Arabitragus*, including Arabian tahr (*Arabitragus jayakari*), the genus *Capra*, including West Caucasian tur (*Capra caucasica*), East Caucasian tur (*Capra caucasica cylindricornis*), Markhor (*Capra falconeri*), Wild goat (*Capra aegagrus*), Domestic goat (*Capra aegagrus hircus*), Alpine ibex (*Capra ibex*), Nubian ibex (*Capra nubiana*), Spanish ibex (*Capra pyrenaica*), Siberian ibex (*Capra sibirica*), Walia ibex (*Capra walie*), the genus *Hemitragus*, including Himalayan tahr (*Hemitragus jemlahicus*), the genus *Ovis*, including Argali (*Ovis ammon*), Domestic sheep (*Ovis aries*), American bighorn sheep (*Ovis Canadensis*), Dall or thinhorn sheep (*Ovis dalli*), European mouflon (*Ovis musimon*), Snow sheep (*Ovis nivicola*), Wild sheep (*Ovis orientalis*), Mouflon (*Ovis orientalis orientalis*), Urial (*Ovis orientalis vignei*), the genus *Nilgiritragus*, including Nilgiri tahr, (*Nilgiritragus hylocrius*), the genus *Pseudois*, including Bharal or Himalayan blue sheep (*Pseudois nayaur*), Dwarf blue sheep (*Pseudois schaeferi*); the tribe Naemorhedini, including the genus *Capricornis*, including Japanese serow (*Capricornis crispus*), Sumatran serow (*Capricornis sumatraensis*), Taiwan serow (*Capricornis swinhoei*), Chinese serow (*Capricornis milneedwardsii*), Red serow (*Capricornis rubidus*), Himalayan serow (*Capricornis thar*), the genus *Nemorhaedus*, including Red goral (*Nemorhaedus baileyi*), Chinese goral (*Nemorhaedus griseus*), Grey goral (*Nemorhaedus goral*), Long-tailed goral (*Naemorhedus caudatus*), the genus *Oreamnos*, including Mountain goat (*Oreamnos americanus*), the genus *Rupicapra*, including Pyrenean chamois (*Rupicapra pyrenaica*), Chamois (*Rupicapra rupicapra*). In certain embodiments, the (skimmed) caprine milk or whey originates from any of the above tribes, genera, or species. In a preferred embodiment, the (skimmed) caprine milk or whey originates from the tribe Caprini. In a more preferred embodiment, the (skimmed) caprine milk or whey originates from the genus *Capra* or *Ovis*, preferably *Capra*, more preferably *Capra aegarus* (*hircus*) or *Ovis aries*, preferably *Capra aegarus hircus*. Accordingly, in a preferred embodiment, the (skimmed) caprine milk or whey is (skimmed) hircine milk or whey.

As used herein, the term "antibody" has its ordinary meaning in the art. By means of further guidance, and without limitation, an antibody is generally comprised in an immunoglobulin. The antibody as described herein can be a full size antibody or a functional fragment thereof such as Fab, a fusion protein or a multimeric protein. Hence, encompassed by the term antibody as used herein are both full length antibodies, as well as antibody fragments, in particular functional antibody fragments. A functional antibody fragment may be an antibody fragment which is capable of binding an antigen, in particular the antigen against which the antibody was raised. According to the invention, the antibody or antibody fragment must be capable of binding to protein A, or alternatively the antibody or antibody fragment may be fused to an entity which is capable of binding to protein A. The term antibody, as used here, includes, but is not limited to conventional antibodies, chimeric antibodies, dAb, bispecific antibody, trispecific antibody, multispecific antibody, bivalent antibody, trivalent antibody, multivalent antibody, VHH, nanobody, Fab, Fab', F(ab')2 scFv, Fv, dAb, Fd, diabody, triabody, single chain antibody, single domain antibody, single antibody variable domain. In the present context, the term antibody is used to describe an immunoglobulin whether natural or partly or wholly engineered. As antibodies can be modified in a number of ways, the term "antibody" should be construed as covering any specific binding molecule or substance having a binding domain with the required binding specificity for the other member of the pair of molecules, i.e. the target molecule, as defined supra. Thus, this term covers antibody fragments, derivatives, functional equivalents and homologues of antibodies, as well as single chain antibodies, bifunctional antibodies, bivalent antibodies, VHH, nanobodies, Fab, Fab', F(ab')2, scFv, Fv, dAb, Fd, diabodies, triabodies and camelid antibodies, including any polypeptide comprising an immunoglobulin binding domain, whether natural or wholly or partially engineered. Chimeric molecules comprising an immunoglobulin binding domain, or equivalent, fused to another polypeptide are therefore included. The term also covers any polypeptide or protein having a binding domain which is, or is homologous to, an antibody binding domain, e.g. antibody mimics. Examples of antibodies are the immunoglobulin isotypes or classes and their (isotypic) subclasses, including IgG (IgG1, IgG2, IgG2(a), IgG2(b), IgG3, IgG4), IgA, IgD, IgM and IgE. The person in the art will thus appreciate that the present invention also relates to antibody fragments, comprising an antigen binding domain such as VHH, nanobodies Fab, scFv, Fv, dAb, Fd, diabodies and triabodies.

As used herein, the term "heterologous antibody" refers to an antibody which does not naturally occur or which is not naturally expressed in a caprine species. Accordingly, a heterologous antibody is not endogenous to a caprine species. A heterologous antibody may be a recombinant or transgenic antibody, i.e. a recombinantly or transgenically expressed antibody. A heterologous antibody may be a chimeric antibody. As such, a heterologous antibody may comprise caprine sequences (e.g. a chimeric antibody comprising caprine and non-caprine antibody fragments), as long as it is not entirely of caprine origin. Also a fusion protein between a caprine antibody or fragment thereof and a non-caprine (protein A binding) moiety falls within the definition of a heterologous antibody as described herein. The heterologous antibody may be codon optimized for expression in a caprine species. The heterologous antibody may be engineered for optimal functionality in a particular species and/or a particular therapeutic setting (e.g. humanized, murinized, etc antibodies). The antibody may be an isotype/(sub)class-switched antibody. According to the invention, the heterologous antibody is at least partially capable of binding to protein A.

In certain embodiments, the (skimmed) caprine milk or whey comprises endogenous or native antibodies, i.e. caprine antibodies naturally occurring and secreted in caprine milk. In is to be understood that such endogenous caprine antibodies are present in addition to the heterologous antibodies.

In certain embodiments, the heterologous antibody is a monoclonal antibody. In certain embodiments one or more different (monoclonal) heterologous antibody may be present in the (skimmed) caprine milk or whey. Accordingly, the (skimmed) caprine milk or whey may comprise a mixture of different (monoclonal) antibodies. Methods for transgenically or recombinantly expressing (monoclonal) antibodies, in particular in mammals, are known in the art (see for instance Moura et al. (2001), Braz Arch Biol Technol, 54(5):927-938; Maksimenko et al. (2013) Acta Naturae, 5(1):33-46; Pollock et al. (1999), J Immunol Methods 231: 147-157; WO 1995/017085). Essentially, for expression of a heterologous protein, such as an antibody, and secretion in milk, a transgenic animal is generated by introduction of a polynucleotide sequence encoding the heterologous protein under control of a milk-specific promoter, such as the WAP, α-casein, or β-casein promoter.

The heterologous antibody may originate from or may comprise one or more fragments of one or more antibody originating from any species, provided the antibody (fragment) is capable of binding to protein A or is fused to a moiety capable of binding to protein A. It will be understood that the skilled person can adequately chose the particular antibody (isotype/(sub)class) from a particular species which properly binds to protein A. The relative binding capabilities/affinity of the respective antibodies are known in the art or can routinely be assessed (such as for instance with surface plasmon resonance). It will be understood that the stronger the antibody is bound by protein A, the larger the ultimate yield will be. While antibodies showing strong binding to protein A are preferred, the methods of the present invention are not limited to such antibodies. Also weaker binding antibodies may be used, albeit with potential loss in final yield. As described herein elsewhere, class switching or generation of chimeric antibodies, or otherwise engineering of the antibodies may result in stronger binding antibodies.

In certain embodiments, the heterologous antibody (fragment) is a mammalian antibody (fragment). In certain embodiments, the heterologous antibody (fragment) is selected from murine, bovine, porcine, canine, feline, or equine antibodies (or fragments). In certain embodiments, the heterologous antibody (fragment) is a human antibody (or fragment). As indicated elsewhere, the antibody may be a chimeric antibody (e.g. comprising fragments from different species or isotypes/(sub)classes) or may be engineered for adequate functionality for the intended therapeutic purpose in the intended species (including for instance caninized, felinized, etc. antibodies).

The isotype/(sub)class of the heterologous antibodies is of no particular relevance and may depend on the desired functionality (e.g. therapeutic indication, target tissues or antigens, etc.). It is to be understood however, that the antibody has to be capable of being bound by protein A, or alternatively that the antibody is fused with a moiety capable of being bound by protein A. In certain embodiments, the antibody is an IgG. In certain embodiments, the antibody is a mixture of different IgG subclasses or may be the total of IgG subclasses. In certain embodiments, the antibody is an IgG1. In certain embodiments, the antibody is an IgG2(a and/or b). In certain embodiments, the antibody is an IgG3. In certain embodiments, the antibody is an IgG4. In certain embodiments, the antibody is a chimeric antibody, class-switched antibody, or otherwise engineered antibody comprising an Fc domain capable of being bound by protein A.

In a preferred embodiment, the heterologous antibody has a higher affinity for protein A than the (endogenous) caprine antibodies, such as the (endogenous) caprine antibodies present in milk, in particular (endogenous) caprine IgG, such as preferably IgG1 and/or IgG2. A heterologous antibody has a higher affinity for protein A than the caprine antibodies if a higher fraction of the heterologous antibody is bound to protein A than the fraction of bound caprine antibody (in particular under identical conditions, such as identical buffer and/or identical pH, such as the pH of the loading or equilibration buffers described herein elsewhere). Affinity can for instance be estimated or determined by loading a protein A matrix with a given amount of antibody (in a particular loading or equilibration buffer and preferably under conditions where the protein A matrix is not saturated with antibody) and detecting the amount or fraction of unbound antibody (such as in flow through or wash buffer). Alternatively, affinity can for instance be estimated or determined by loading a protein A matrix with a given amount of antibody (in a particular loading or equilibration buffer and preferably under conditions where the protein A matrix is not saturated with antibody) and detecting the amount or fraction of bound antibody after elution, such as with a elution buffer as described herein elsewhere (preferably after washing the matrix with wash buffer). In certain embodiments, a higher affinity of heterologous antibodies is represented by a fraction of bound heterologous antibodies which is at least 5% higher (wt % or mole %) than the fraction of bound caprine antibodies (such as caprine IgG, such as preferably caprine IgG1 and/or IgG2), preferably at least 10% higher, more preferably at least 15% higher, even more preferably at least 20% higher. It will be understood that other techniques for determining antibody affinity are equally suitable, such as for instance surface plasmon resonance. In certain embodiments, affinity may be determined by determination of the KD, as is known in the art. Antibodies having a higher affinity for protein A will have a lower KD. In certain embodiments, the KD of the heterologous antibody and protein A is at least 2 times lower than the KD of the caprine antibody (i.e. at most half of KD of the caprine antibody) the and protein A, preferably at least 5 times lower (i.e. at most 20% of KD of the caprine antibody), more preferably at least 10 times lower (i.e. at most 10% of KD of the caprine antibody). It will be understood that the heterologous antibody having a higher affinity for protein A as described herein may be engineered, as described herein elsewhere (such as class switching or generation of chimeric antibodies, or otherwise engineering of the antibodies which results in stronger binding antibodies).

In certain embodiments, the heterologous antibody is a murine IgG2a, IgG2b, or IgG3 antibody (or an engineered antibody comprising a murine IgG2a, IgG2b, or IgG3 heavy chain, Fc, or CH2/CH3 fragment). In certain embodiments, the heterologous antibody is a murine IgM antibody (or an engineered antibody comprising a murine IgM heavy chain, Fc, or CH2/CH3 fragment).

In certain embodiments, the heterologous antibody is a bovine IgG antibody (or an engineered antibody comprising a bovine IgG heavy chain, Fc, or CH2/CH3 fragment). In certain embodiments, the heterologous antibody is a bovine IgG1 or IgG2 antibody (or an engineered antibody comprising a bovine IgG1 or IgG2 heavy chain, Fc, or CH2/CH3 fragment).

In certain embodiments, the heterologous antibody is a canine IgG antibody (or an engineered antibody comprising a canine IgG heavy chain, Fc, or CH2/CH3 fragment). In certain embodiments, the heterologous antibody is a canine IgG1 or IgG2 antibody (or an engineered antibody comprising a canine IgG1 or IgG2 heavy chain, Fc, or CH2/CH3 fragment).

In certain embodiments, the heterologous antibody is an equine (including donkey or horse) IgG antibody (or an engineered antibody comprising an equine IgG heavy chain, Fc, or CH2/CH3 fragment). In certain embodiments, the heterologous antibody is an equine IgG1 or IgG2 antibody (or an engineered antibody comprising an equine IgG1 or IgG2 heavy chain, Fc, or CH2/CH3 fragment).

In certain embodiments, the heterologous antibody is a monkey (such as rhesus) IgG antibody (or an engineered antibody comprising a monkey IgG heavy chain, Fc, or CH2/CH3 fragment). In certain embodiments, the heterologous antibody is a monkey IgG1 or IgG2 antibody (or an engineered antibody comprising a monkey IgG1 or IgG2 heavy chain, Fc, or CH2/CH3 fragment).

In certain embodiments, the heterologous antibody is a porcine IgG antibody (or an engineered antibody comprising a porcine IgG heavy chain, Fc, or CH2/CH3 fragment). In certain embodiments, the heterologous antibody is a porcine IgG1 or IgG2 antibody (or an engineered antibody comprising a porcine IgG1 or IgG2 heavy chain, Fc, or CH2/CH3 fragment).

In certain embodiments, the heterologous antibody is a rabbit IgG antibody (or an engineered antibody comprising a rabbit IgG heavy chain, Fc, or CH2/CH3 fragment). In certain embodiments, the heterologous antibody is a rabbit IgG1 or IgG2 antibody (or an engineered antibody comprising a rabbit IgG1 or IgG2 heavy chain, Fc, or CH2/CH3 fragment).

In certain embodiments, the heterologous antibody is a rat IgG2c antibody (or an engineered antibody comprising a rat IgG2c heavy chain, Fc, or CH2/CH3 fragment).

In certain embodiments, the heterologous antibody is a feline IgG antibody (or an engineered antibody comprising a feline IgG heavy chain, Fc, or CH2/CH3 fragment). In certain embodiments, the heterologous antibody is a feline IgG1 or IgG2 antibody (or an engineered antibody comprising a feline IgG1 or IgG2 heavy chain, Fc, or CH2/CH3 fragment).

In certain embodiments, the heterologous antibody is a human IgG1, IgG2, or IgG4 antibody (or an engineered antibody comprising a human IgG1, IgG2, or IgG4 heavy chain, Fc, or CH2/CH3 fragment). In certain embodiments, the heterologous antibody is a human IgA antibody (or an engineered antibody comprising a human IgA heavy chain, Fc, or CH2/CH3 fragment). In certain embodiments, the heterologous antibody is a human IgM antibody (or an engineered antibody comprising a human IgM heavy chain, Fc, or CH2/CH3 fragment).

In certain embodiments, the heterologous antibody is a therapeutic antibody. In certain embodiments, the antibody is a therapeutic antibody for veterinary use. It will be understood that the antibody per se need not be therapeutic, but may be coupled or conjugated to a therapeutic agent (e.g. a radioligand, a toxin, a (pro)drug, etc.) or a carrier (e.g. liposome) comprising such agent. The heterologous antibody may be for use in immunotherapy, including activation immunotherapy (e.g. treatment of cancer, immune recovery, vaccination, etc.) or suppression immunotherapy (e.g. treatment of allergies, inducing immune tolerance, delivery of immunosuppressive drugs, etc).

According to the methods of the invention as described herein, the (skimmed) whey is contacted or incubated with a protein A containing matrix or resin, such as protein A coupled sepharose beads. In certain embodiments, the (skimmed) whey is subjected to chromatography for purifying antibodies. In certain embodiments, the methods of the present invention involve affinity chromatography. In certain embodiments, the methods involve column chromatography, such as column affinity chromatography. In certain embodiments, the methods involve packed bed or expanded bed (column) chromatography (preferably packed bed), such as packed/expanded bed (column) affinity chromatography. In certain embodiments, the methods of the invention involve continuous or batch chromatography, such as continuous/batch (packed/expanded bed column affinity) chromatography. In certain embodiments, the methods of the invention involve continuous/batch packed/expanded bed (column) chromatography. Continuous chromatography is known in the art, and includes for instance PCC (Periodic Counter Current), MCC (Multicolumn Continuous Chromatography), or SMB (simulated Moving Bed). Typically, these continuous chromatography methods involve the use of multiple columns (2, 3, 4, 8 or more), which are alternatively loaded, washed, eluted, regenerated. Column chromatography essentially involves providing a column which is packed with a stationary phase (i.e. a bed), in the present case the protein A containing matrix or resin. Columns (and in particular bed) may have any suitable size, height, or dimensions, depending on the scale of the purification system (for instance columns with a 10 cm bed height). The column comprising the stationary phase is typically loaded with a mobile phase, in this case the (skimmed) whey. According to the present invention, antibodies are retained on the stationary phase, and can be eluted. In certain embodiments, chromatography is or includes HPLC (high performance liquid chromatography). In HPLC, the mobile phase is forced under pressure through the stationary phase. Alternatively, the mobile phase may percolate through the stationary phase by gravity or by applying a vacuum. As indicated earlier, the antibodies are retained on the stationary phase while the whey flows through and exits the stationary phase as antibody-depleted whey. Accordingly, the chromatography effectively separates the antibodies from the whey. The (antibody-depleted) whey is separated from the protein A containing matrix or resin as a flowthrough.

The time of contacting the whey with the protein A containing matrix or resin may be variable, and may for instance be dependent on the dimensions of the column or column bed, as well as the speed at which the whey flows through the column or bed (which may for instance vary depending on whether chromatography is based on gravity or on application of pressure). Alternatively, in case no column chromatography is performed, the protein A containing matrix or resin may be incubated with the whey for a fixed period of time, after which the whey is separated from the protein A containing matrix or column (e.g. by centrifugation or filtration).

As used herein, "protein A" refers to a 42 kDa surface protein originally found in the cell wall of the bacteria *Staphylococcus aureus*. It is encoded by the spa gene. Protein A has the ability to bind immunoglobulins. It is composed of five homologous Ig-binding domains that fold into a three-helix bundle. Each domain is able to bind proteins from many mammalian species, most notably IgGs. It binds the heavy chain within the Fc region of most immunoglobulins and also within the Fab region in the case of the human VH3 family. Protein A may be produced and purified in industrial fermentation for use in immunology, biological research and industrial applications. Natural (or native) protein A can be cultured in *Staphylococcus aureus* and contains the five homologous antibody binding regions described above and a C-terminal region for cell wall attachment. Alternatively, protein A may be produced recombinantly, such as in *Escherichia coli* or *Brevibacillus*. Recombinant versions of protein A also contain the five homologous antibody binding domains but may vary in other parts of the structure in order to facilitate coupling to porous substrates. Engineered versions of protein A are also available, among which rProtein A, B4, C-CYS. Engineered versions may be multimers (typically tetramers, pentamers or hexamers) of a single domain which has been modified to improve usability in industrial applications. All of these forms of protein A are suitable for use according to the present invention.

As used herein, a protein A containing matrix or resin comprises a substrate to which protein A is immobilized or coupled (covalently or non-covalently, preferably covalently). The substrate on which protein as is coupled or immobilized typically is a solid or semi-solid support. Suitable substrates for instance include sepharose or other types or crosslinked (optionally beaded) forms or polysaccharide polymers, such as agarose. Other types of resins or matrices may equally be suitable, such as for instance glass beads. The support may be porous or non-porous. By means of example, and without limitation, suitable protein A containing matrices or resins include Praeso AP or APc (both from Purolite), MabSelectSure (GE Healthcare), or AffiGel (Bio-Rad), all of which may be advantageously used in the methods according to the invention. In a preferred embodiment, Praeso AP or APc is used.

In certain embodiments, the (skimmed) whey is diluted prior to contacting with the protein A containing matrix or resin, such a 0.5, 0.6, 0.7, 0.8, 0.9, 1.0, 1.1, 1.2, 1.3, 1.4, 1.5, 1.6, 1.7, 1.8, 1.9, 2.0 or more times diluted. The ratio of the diluent to whey may be 0.1:1, 0.2:1, 0.3:1, 0.4:1, 0.5:1, 0.6:1, 0.7:1, 0.8:1, 0.9:1, 1:1, 1.1:1, 1.2:1, 1.3:1, 1.4:1, 1.5:1, 1.6:1, 1.7:1, 1.8:1, 1.9:1, 2:1, 2.1:1, 2.2:1, 2.3:1, 2.4:1, 2.5:1, 2.6:1, 2.7:1, 2.8:1, 2.9:1, 3:1, 3.1:1, 3.2:1, 3.3:1, 3.4:1, 3.5:1, 3.6:1, 3.7:1, 3.8:1, 3.9:1, 4:1, 4.1:1, 4.2:1, 4.3:1, 4.4:1, 4.5:1, 4.6:1, 4.7:1, 4.8:1, 4.9:1, 5:1. In certain embodiments, the ratio of the diluent to whey may be between 0.5:1 and 1.5:1, such as 1:1. A suitable buffer, optionally at a suitable pH may be used as described herein elsewhere (for instance buffers and/or pH as used for equilibrating the milk/whey and/or protein A containing matrix or resin). In certain embodiments, the pH of the whey is adjusted to between pH 5 to pH 8, such as pH 6.0, optionally with with NaOH 1M before purification. Optionally, a buffer can be added to the sample, such as between 5 and 50 v/v % buffer, such as about 10 v/v % buffer. The buffer may for instance be equilibration buffer or concentrated equilibration buffer, as described herein elsewhere, or may for instance be a NaCl containing buffer.

In certain embodiments, the protein A containing matrix or resin and/or the (skimmed) whey is equilibrated at a pH ranging from about 5 to about 8 prior to contacting the (skimmed) whey with the protein A containing matrix or resin. As used herein, "equilibrated" refers to adjustment of the pH (if needed) to the projected range or value. It will be understood that adjustment of the pH of the protein A containing matrix or resin may comprise contacting the protein A containing (solid) matrix or resin with a suitable buffer having the indicated pH range or value. It will be understood that adjustment of the pH of the whey may comprise adding to the whey a suitable base (such as NaOH) or buffer, having a pH range or value such that the indicated final pH range or value is reached. In certain embodiments, the pH of the (skimmed) milk is adjusted after caseins precipitation, but before removal of the caseins (i.e. before straining, centrifugation, or filtration). It will be understood that preferably the time between such pH adjustment and caseins removal is preferably short, so as to exclude casein(s) resolubilization. In certain embodiments, the pH of the (skimmed) whey/milk and/or protein A containing matrix or resin is equilibrated/adjusted to a pH ranging from about 4.5 to 8.0, such as about 4.7 to about 8.0, such as about 5.0 to about 8.0, preferably about 6.0 to about 7.0, such as from about 5.0 to about 8.0, 7.9, 7.8, 7.7, 7.6, 7.4, 7.3, 7.2, 7.1, 7.0, 6.9, 6.8, 6.7, 6.6, 6.5, 6.4, 6.3, 6.2, 6.1, 6.0, 5.9, 5.8, 5.7, 5.6, 5.5, 5.4, 5.3, 5.2, or 5.1, about 5.1 to about 8.0, 7.9, 7.8, 7.7, 7.6, 7.4, 7.3, 7.2, 7.1, 7.0, 6.9, 6.8, 6.7, 6.6, 6.5, 6.4, 6.3, 6.2, 6.1, 6.0, 5.9, 5.8, 5.7, 5.6, 5.5, 5.4, 5.3, or 5.2, about 5.2 to about 8.0, 7.9, 7.8, 7.7, 7.6, 7.4, 7.3, 7.2, 7.1, 7.0, 6.9, 6.8, 6.7, 6.6, 6.5, 6.4, 6.3, 6.2, 6.1, 6.0, 5.9, 5.8, 5.7, 5.6, 5.5, 5.4, or 5.3, about 5.3 to about 8.0, 7.9, 7.8, 7.7, 7.6, 7.4, 7.3, 7.2, 7.1, 7.0, 6.9, 6.8, 6.7, 6.6, 6.5, 6.4, 6.3, 6.2, 6.1, 6.0, 5.9, 5.8, 5.7, 5.6, 5.5, or 5.4, about 5.4 to about 8.0, 7.9, 7.8, 7.7, 7.6, 7.4, 7.3, 7.2, 7.1, 7.0, 6.9, 6.8, 6.7, 6.6, 6.5, 6.4, 6.3, 6.2, 6.1, 6.0, 5.9, 5.8, 5.7, 5.6, or 5.5, about 5.5 to about 8.0, 7.9, 7.8, 7.7, 7.6, 7.4, 7.3, 7.2, 7.1, 7.0, 6.9, 6.8, 6.7, 6.6, 6.5, 6.4, 6.3, 6.2, 6.1, 6.0, 5.9, 5.8, 5.7, or 5.6, about 5.6 to about 8.0, 7.9, 7.8, 7.7, 7.6, 7.4, 7.3, 7.2, 7.1, 7.0, 6.9, 6.8, 6.7, 6.6, 6.5, 6.4, 6.3, 6.2, 6.1, 6.0, 5.9, 5.8, or 5.7, about 5.7 to about 8.0, 7.9, 7.8, 7.7, 7.6, 7.4, 7.3, 7.2, 7.1, 7.0, 6.9, 6.8, 6.7, 6.6, 6.5, 6.4, 6.3, 6.2, 6.1, 6.0, 5.9, or 5.8, about 5.8 to about 8.0, 7.9, 7.8, 7.7, 7.6, 7.4, 7.3, 7.2, 7.1, 7.0, 6.9, 6.8, 6.7, 6.6, 6.5, 6.4, 6.3, 6.2, 6.1, 6.0, or 5.9, about 5.9 to about 8.0, 7.9, 7.8, 7.7, 7.6, 7.4, 7.3, 7.2, 7.1, 7.0, 6.9, 6.8, 6.7, 6.6, 6.5, 6.4, 6.3, 6.2, 6.1, or 6.0, about 6.0 to about 8.0, 7.9, 7.8, 7.7, 7.6, 7.4, 7.3, 7.2, 7.1, 7.0, 6.9, 6.8, 6.7, 6.6, 6.5, 6.4, 6.3, 6.2, or 6.1, about 6.1 to about 8.0, 7.9, 7.8, 7.7, 7.6, 7.4, 7.3, 7.2, 7.1, 7.0, 6.9, 6.8, 6.7, 6.6, 6.5, 6.4, 6.3, or 6.2, about 6.2 to about 8.0, 7.9, 7.8, 7.7, 7.6, 7.4, 7.3, 7.2, 7.1, 7.0, 6.9, 6.8, 6.7, 6.6, 6.5, 6.4, or 6.3, about 6.3 to about 8.0, 7.9, 7.8, 7.7, 7.6, 7.4, 7.3, 7.2, 7.1, 7.0, 6.9, 6.8, 6.7, 6.6, 6.5, or 6.4, about 6.4 to about 8.0, 7.9, 7.8, 7.7, 7.6, 7.4, 7.3, 7.2, 7.1, 7.0, 6.9, 6.8, 6.7, 6.6, or 6.5, about 6.5 to about 8.0, 7.9, 7.8, 7.7, 7.6, 7.4, 7.3, 7.2, 7.1, 7.0, 6.9, 6.8, 6.7, or 6.6, about 6.6 to about 8.0, 7.9, 7.8, 7.7, 7.6, 7.4, 7.3, 7.2, 7.1, 7.0, 6.9, 6.8, or 6.7, about 6.7 to about 8.0, 7.9, 7.8, 7.7, 7.6, 7.4, 7.3, 7.2, 7.1, 7.0, 6.9, or 6.8, about 6.8 to about 8.0, 7.9, 7.8, 7.7, 7.6, 7.4, 7.3, 7.2, 7.1, 7.0, or 6.9, about 6.9 to about 8.0, 7.9, 7.8, 7.7, 7.6, 7.4, 7.3, 7.2, 7.1, or 7.0, about 7.0 to about 8.0, 7.9, 7.8, 7.7, 7.6, 7.4, 7.3, 7.2, or 7.1, about 7.1 to about 8.0, 7.9, 7.8, 7.7, 7.6, 7.4, 7.3, or 7.2, about 7.2 to about 8.0, 7.9, 7.8, 7.7, 7.6, 7.4, or 7.3, about 7.3 to about 8.0, 7.9, 7.8, 7.7, 7.6, or 7.4, about 7.4 to about 8.0, 7.9, 7.8, 7.6, or 7.5, about 7.5 to about 8.0, 7.9, 7.8, 7.7, or 7.6, about 7.6 to about 8.0, 7.9, 7.8, or 7.7, about 7.7 to about 8.0, 7.9, or 7.8, about 7.8 to about 8.0, or 7.9, about 7.9 to about 8.0. In certain embodiments, the pH of the (skimmed) whey/milk and/or protein A containing matrix or resin is equilibrated/adjusted to a pH ranging from about 4.7 to about 7.5, such as about 4.8 to about 7.5, such as about 4.9 to about 7.5, such as about 5.0 to about 7.5, such as about 5.5 to about 7.5. In certain embodiments, the pH of the (skimmed) whey/milk and/or protein A containing matrix or resin is equilibrated/adjusted to a pH ranging from about 6.0 to about 7.0. In certain embodiments, the pH of the (skimmed) whey/milk and/or protein A containing matrix or resin is equilibrated/adjusted to a pH ranging from about 6.0 to about 6.5. In certain embodiments, the pH of the (skimmed) whey/milk and/or protein A containing matrix or resin is equilibrated/adjusted to a pH ranging from about 6.5 to about 7.0. In certain embodiments, the pH of the (skimmed) whey/milk and/or protein A containing matrix or resin is equilibrated/adjusted to a pH ranging from about 5.5 to about 7.0. In certain embodiments, the pH of the (skimmed) whey/milk and/or protein A containing matrix or resin is equilibrated/adjusted to a pH ranging from about 5.0 to about 7.0. In certain embodiments, the pH of the (skimmed) whey/milk and/or protein A containing matrix or resin is equilibrated/adjusted to a pH ranging from about 4.7 to about 7.0. In certain embodiments, the pH of the (skimmed) whey/milk and/or protein A containing matrix or resin is equilibrated/adjusted to a pH ranging from about 4.5 to about 7.0.

In certain embodiments, the buffer for equilibrating the protein A containing matrix or resin, and/or the milk/whey (or for diluting the milk/whey) may be without limitation an acetate buffer, citrate buffer, amino acid supplemented buffers, phosphate buffers, such as PBS, TBS, etc. In certain preferred embodiments, the buffer is an acetate buffer. In certain embodiments, the buffers comprises between 10 and 100 mM buffering agent(s), such as about 20 mM. In certain embodiments, the buffer is supplemented with salt(s), such as NaCl. In certain embodiments, the salt concentration is between about 0 and 100 mM. In certain embodiments, the buffer comprises about 50 mM NaCl and about 50 mM sodium acetate and has a pH of about 6.0.

In certain embodiments, the equilibration buffer is selected from:

Phosphate buffer saline (PBS): from 20 to 100 mM phosphate, from 50 to 500 mM NaCl, pH from 5.8 to 8. Preferably, 50 mM phosphate, 250 mM NaCl, pH 6

Acetate with or without NaCl. From 20 to 100 mM acetate, from 0 to 500 mM NaCl, pH from 4.7 to 6. Preferably, 50 mM acetate, 50 mM NaCl, pH 6

MES with or without NaCl. From 20 to 100 mM MES, from 0 to 500 mM NaCl, pH from 5.5 to 6.7. Preferably, 50 mM MES, 50 mM NaCl, pH 6

BIS-tris with or without NaCl. From 20 to 100 mM BIS-tris, from 0 to 500 mM NaCl, pH from 5.8 to 7.2. Preferably, 50 mM BIS-tris, 50 mM NaCl, pH 6

Citrate with or without NaCl. From 20 to 100 mM citrate, from 0 to 500 mM NaCl, pH from 5.8 to 7.2. Preferably, 50 mM BIS-tris, 50 mM NaCl, pH 6

Malate with or without NaCl. From 20 to 100 mM BIS-tris, from 0 to 500 mM NaCl, pH from 4.0 to 6.0. Preferably, 50 mM malate, 50 mM NaCl, pH 6

Carbonate with or without NaCl. From 20 to 100 mM carbonate, from 0 to 500 mM NaCl, pH from 6.0 to 8.0. Preferably, 50 mM carbonate, 50 mM NaCl, pH 6

Cacodylate with or without NaCl. From 20 to 100 mM cacodylate, from 0 to 500 mM NaCl, pH from 5.0 to 7.4. Preferably, 50 mM cacodylate, 50 mM NaCl, pH 6

Pyridine with or without NaCl. From 20 to 100 mM pyridine, from 0 to 500 mM NaCl, pH from 4.9 to 5.9. Preferably, 50 mM pyridine, 50 mM NaCl, pH 5.5

Succinate with or without NaCl. From 20 to 100 mM succinate, from 0 to 500 mM NaCl, pH from 5.5 to 6.5 or 4.7 to 5.2. Preferably, 50 mM succinate, 50 mM NaCl, pH 6

Maleate with or without NaCl. From 20 to 100 mM maleate, from 0 to 500 mM NaCl, pH from 5.5 to 7.2. Preferably, 50 mM succinate, 50 mM NaCl, pH 6

In certain embodiments, after the (skimmed) whey is separated from the protein A containing matrix or resin (e.g. by gravity flow), the protein A containing matrix is washed (i.e. prior to elution of the heterologous antibody). In certain embodiments, the protein A containing matrix is washed at least once, such as 1, 2, 3 or more times, or is washed with at least 1, such as 1, 2, 3, or more, such as at least 5 or at least 10 bed (such as column) volumes (wherein the bed volume is the volume of the (packed) protein A containing matrix or resin), such as 2 to 5 bed volumes, or 3 to 5 or 4 to 5 bed volumes. In certain embodiments, the protein A containing matrix is washed with at least one, such as 1, 2, or 3 bed volumes for batch purification. In certain embodiments, the protein A containing matrix is washed with at least 5, such as 5 to 15 bed volumes for column purification. In certain embodiments, the protein A containing matrix or resin is washed with the same buffer as the equilibration buffer, optionally equilibration buffer having an increased salt (such as NaCl) concentration (such as for instance increased at least doubled salt concentration, such as at least 5-fold increased salt concentration, such as 10-fold increased salt concentration, such as from about 50 mM NaCl to about 500 mM NaCl). In certain embodiments, the protein A containing matrix or resin is washed at least once with a buffer (e.g. acetate buffer) having a pH ranging from about 4.5 to about 8.0. In certain embodiments, the protein A containing matrix or resin is washed at least once with a buffer having a pH ranging from about 4.5 to about 7.0. In certain embodiments, the protein A containing matrix or resin is washed at least once with a buffer having a pH ranging from about 4.5 to about 6.0. In certain preferred embodiments, the protein A containing matrix or resin is washed at least once with a buffer having a pH ranging from about 4.5 to about 5.0, such as about 4.6 to 5.0 or 4.7 to 4.9. In a preferred embodiment, the protein A containing matrix or resin is washed at least once with a buffer having a pH of about 4.8 or having a pH of 4.8. In certain embodiments, the protein A containing matrix or resin is washed at least once with a buffer (e.g. acetate buffer) having a pH ranging from about 4.0 to about 8.0. In certain embodiments, the protein A containing matrix or resin is washed at least once with a buffer having a pH ranging from about 4.0 to about 7.0. In certain embodiments, the protein A containing matrix or resin is washed at least once with a buffer having a pH ranging from about 4.0 to about 6.0. In certain preferred embodiments, the protein A containing matrix or resin is washed at least once with a buffer having a pH ranging from about 4.0 to about 5.0, such as about 4.3 to 5.0 or 4.5 to 5.0. In a preferred embodiment, the protein A containing matrix or resin is washed at least once with a buffer having a pH of about 4.8 or having a pH of 4.8. In a preferred embodiment, the protein A containing matrix or resin is washed at least once with a buffer having a pH of about 4.7 or having a pH of 4.7. It will be understood that in these embodiments if multiple washes are performed, at least one wash (or bed volume), preferably at least two washes (or bed volumes) may be performed at the indicated pH range or value in order to elute endogenous caprine antibodies. Surprisingly, the present inventors have determined that the above pH ranges of the washing buffer improve yield and/or purity of the heterologous antibody. In particular, at the indicated pH ranges, residually bound endogenous caprine antibodies elute from the protein A containing matrix or resin, while the heterologous antibodies remain bound to the protein A containing matrix or resin. In this context, in certain embodiments, the heterologous antibody has a different isoelectric point than the endogenous caprine antibodies, such as a higher or lower isoelectric point than the endogenous caprine antibodies. To this extent, the heterologous antibody may be engineered to this effect (e.g. class switching, chimeric antibodies, or otherwise recombinant engineering to affect isoelectric point of the antibody). In certain embodiments, the isoelectric point of the heterologous antibody is between about 0.5 to 3.0 units different preferably between about 1.0 to about 3.0 units different than the isoelectric point of endogenous caprine antibodies, such as about 1 to 2 units, preferably at least 0.5 unit, such as at least 1 unit. In certain embodiments, the isoelectric point of the heterologous antibody ranges from about 6.0 to about 8.0, preferably about 6.0 to about 7.5, more preferably about 6.0 to about 7.0 or about 6.0 to about 6.5. In certain embodiments, the isoelectric point of the heterologous antibody is lower than 7.5, preferably lower than 7.0, such as lower than 6.9, 6.8, 6.7, 6.5, 6.4, 6.3, 6.2, 6.1, 6.0.

In certain preferred embodiments, the pH of the washing (preferably a wash buffer which elutes the endogenous caprine antibodies) and/or equilibration buffer is higher than the pH of the elution buffer (for eluting the heterologous antibodies). For instance, if the pH of the washing buffer, such as the washing buffer for eluting endogenous caprine antibodies is 4.8, then the elution buffer for the heterologous antibodies is less than 4.8. In certain embodiments, at least one wash buffer (preferably a wash buffer which elutes the endogenous caprine antibodies) has a pH which is at least 1 unit lower, and preferably at most 2 units lower than the pH of the equilibration buffer. In certain embodiments, the elution buffer (for eluting the heterologous antibodies) has a pH which is at least 1 unit, preferably at most 2 units lower than the pH of the wash buffer (in particular the wash buffer having the lowest pH, i.e. the wash buffer for eluting endogenous caprine antibodies. In certain embodiments, the elution buffer (for eluting the heterologous antibodies) has a pH which is at least 0.1 unit, preferably at most 2 units lower than the pH of the wash buffer (in particular the wash buffer having the lowest pH, i.e. the wash buffer for eluting endogenous caprine antibodies. In certain embodiments, the elution buffer (for eluting the heterologous antibodies) has a pH which is at least 0.2 unit, preferably at most 2 units lower than the pH of the wash buffer (in particular the wash buffer having the lowest pH, i.e. the wash buffer for eluting endogenous caprine antibodies. In certain embodiments, the elution buffer (for eluting the heterologous antibodies) has a pH which is at least 0.3 unit, preferably at most 2 units lower than the pH of the wash buffer (in particular the wash buffer having the lowest pH, i.e. the wash buffer for eluting endogenous caprine antibodies. In certain embodiments, the elution buffer (for eluting the heterologous antibodies) has a pH which is at least 0.4 unit, preferably at most 2 units lower than the pH of the wash buffer (in particular the wash buffer having the lowest pH, i.e. the wash buffer for eluting endogenous caprine antibodies. In certain embodiments, the elution buffer (for eluting the heterologous antibodies) has a pH which is at least 0.5 unit, preferably at most 2 units lower than the pH of the wash buffer (in particular the wash buffer having the lowest pH, i.e. the wash buffer for eluting endogenous caprine antibodies.

In certain embodiments, the heterologous antibody is eluted (i.e. dissociated) from the protein A containing matrix or resin. In certain embodiments, heterologous antibodies are eluted with up to 5 bed volumes, such as 5 bed volumes of elution buffer. In certain embodiments, heterologous antibodies are eluted with up to 4 bed volumes, such as 4 bed volumes of elution buffer. In certain embodiments, heterologous antibodies are eluted with up to 3 bed volumes, such as 3 bed volumes of elution buffer. In certain embodiments, the heterologous antibodies are eluted from the protein A containing matrix or resin is with the same buffer as the equilibration buffer but having a pH allowing elution of the heterologous antibody. In certain embodiments the heterologous antibodies are eluted from the protein A containing matrix or resin is with the same buffer as the equilibration buffer but having a different salt concentration allowing elution of the heterologous antibody. Typically an increased salt concentration is used. It will be understood that, in particular for column chromatography, eluate may be collected in different fractions. Antibody concentration may be determined in each fraction in order to identify the fractions having the highest concentration and/or purity. Such fractions may be pooled to ensure the highest heterologous antibody yield and concentration. In certain embodiments, each fraction is about one bed volume.

In certain embodiments, the elution buffer comprises Elution buffer could be: glycine, phosphate, citrate, glycylglycine, malate, formate, citrate, maleate, etc.

In certain embodiments, the heterologous antibody is eluted in a buffer having a pH ranging from about 2 to about 5, or from about 3 to about 5, or from about 2.0 or 3.0 to about 5.0, preferably from about 2.0 or 3.0 to 4.8 or 2.0 or 3.0 to 4.7, more preferably 2.0 or 3.0 to 4.5, 2.0 or 3.0 to 4.3, or 2.0 or 3.0 to 4.0, preferably from about 2.0 or 3.0 to 4.6 or 2.0 or 3.0 to 4.5. In certain embodiments, the heterologous antibody is eluted in a buffer having a pH ranging from about 3.0 to about 5.0, such as about 3.0 to about 5.0, 4.9, 4.8, 4.7, 4.6, 4.5, 4.4, 4.3, 4.2, 4.1, 4.0, 3.9, 3.8, 3.7, 3.6, 3.5, 3.4, 3.3, 3.2, or 3.1, about 3.1 to about 5.0, 4.9, 4.8, 4.7, 4.6, 4.5, 4.4, 4.3, 4.2, 4.1, 4.0, 3.9, 3.8, 3.7, 3.6, 3.5, 3.4, 3.3, or 3.2, about 3.2 to about 5.0, 4.9, 4.8, 4.7, 4.6, 4.5, 4.4, 4.3, 4.2, 4.1, 4.0, 3.9, 3.8, 3.7, 3.6, 3.5, 3.4, or 3.3, about 3.3 to about 5.0, 4.9, 4.8, 4.7, 4.6, 4.5, 4.4, 4.3, 4.2, 4.1, 4.0, 3.9, 3.8, 3.7, 3.6, 3.5, or 3.4, about 3.4 to about 5.0, 4.9, 4.8, 4.7, 4.6, 4.5, 4.4, 4.3, 4.2, 4.1, 4.0, 3.9, 3.8, 3.7, 3.6, or 3.5, about 3.5 to about 5.0, 4.9, 4.8, 4.7, 4.6, 4.5, 4.4, 4.3, 4.2, 4.1, 4.0, 3.9, 3.8, 3.7, or 3.6, about 3.6 to about 5.0, 4.9, 4.8, 4.7, 4.6, 4.5, 4.4, 4.3, 4.2, 4.1, 4.0, 3.9, 3.8, or 3.7, about 3.7 to about 5.0, 4.9, 4.8, 4.7, 4.6, 4.5, 4.4, 4.3, 4.2, 4.1, 4.0, 3.9, or 3.8, about 3.8 to about 5.0, 4.9, 4.8, 4.7, 4.6, 4.5, 4.4, 4.3, 4.2, 4.1, 4.0, or 3.9, about 3.9 to about 5.0, 4.9, 4.8, 4.7, 4.6, 4.5, 4.4, 4.3, 4.2, 4.1, or 4.0, about 4.0 to about 5.0, 4.9, 4.8, 4.7, 4.6, 4.5, 4.4, 4.3, 4.2, or 4.1, about 4.1 to about 5.0, 4.9, 4.8, 4.7, 4.6, 4.5, 4.4, 4.3, or 4.2, about 4.2 to about 5.0, 4.9, 4.8, 4.7, 4.6, 4.5, 4.4, or 4.3, about 4.3 to about 5.0, 4.9, 4.8, 4.7, 4.6, 4.5, or 4.4, about 4.4 to about 5.0, 4.9, 4.8, 4.7, 4.6, or 4.5, about 4.5 to about 5.0, 4.9, 4.8, 4.7, or 4.6, about 4.6 to about 5.0, 4.9, 4.8, or 4.7, about 4.7 to about 5.0, 4.9, or 4.8, about 4.8 to about 5.0, or 4.9, about 4.9 to about 5.0. In certain preferred embodiments the heterologous antibody eluted in a buffer having a pH ranging from about 3.0 to about 4.5 or about 3.0 to about 4.0, such as 3.5 or about 3.5. In certain preferred embodiments the heterologous antibody is eluted in a buffer having a pH ranging from about 2.0 to about 4.5 or about 2.0 to about 4.0, or about 2.0 to about 4.3.

It will be understood that eluted heterologous antibodies may be further processed downstream, such as including dilution or concentration, neutralization, dialysis, etc. Depending on the therapeutic indication, the antibodies may be further suitably formulated.

In certain embodiments, equilibration is performed at pH 5.5 to pH 7.0, such as preferably pH 6, at least one wash step is performed at pH 4.5 to pH 5.0, such as preferably pH 4.8 (for endogenous goat antibody elution/removal), and elution is performed at pH 2 to pH 4, such as preferably pH 3.5 (for heterologous antibody elution). In certain embodiments, equilibration and/or at least one wash step (preferably all) is performed at pH 4.5 to pH 5.0, such as preferably pH 4.8 (for endogenous goat antibody elution/removal), and elution is performed at pH 2.0 to pH 4.0, such as preferably pH 3.5 (for heterologous antibody elution). In certain embodiments, equilibration and/or at least one (preferably all) wash step is performed at pH 4.0 to pH 5.0, such as preferably pH 4.8 (for endogenous goat antibody elution/removal), and elution is performed at pH 2.0 to pH 4.0, such as preferably pH 3.5 (for heterologous antibody elution). In certain embodiments, equilibration and/or at least one wash step (preferably all) is performed at pH 4.5 to pH 5.0, such as preferably pH 4.8 (for endogenous goat antibody elution/removal), and elution is performed at pH 2.0 to pH 4.5, such as preferably pH 3.5 (for heterologous antibody elution). In all these embodiments, the pH for equilibration and/or washing preferably is higher than the pH for heterologous antibody elution, as described herein elsewhere, such as for instance at least 0.1 units higher. In certain embodiments an additional elution step is included, preferably at pH 3.0. In certain embodiments the buffer in one or more of these steps, preferably all, is an acetate buffer (with or without salt, preferably NaCl). In certain embodiments, the sample is diluted, such as preferably in equilibration buffer. In certain embodiments, eluates are neutralized, such as to about pH 9, such as in a 1M Tris buffer.

In certain embodiments, the equilibration buffer and/or at least one wash buffer comprises sodium acetate 50 mM with 50 mM NaCl at pH 6, such as pH 6.0. In certain embodiments, at least one was buffer comprises sodium acetate 50 mM with 50 mM NaCl at pH 4.8. In certain embodiments, the elution buffer comprises sodium acetate 50 mM NaCl pH 4.8 or 3.5 or 3.0

In certain embodiments, the equilibration buffer comprises 50 mM sodium acetate, 500 mM NaCl, pH 6, 10 column volumes. In certain embodiments, the goat IgG is removed/eluted with a buffer comprising 50 mM sodium acetate, 100 mM NaCl, pH 4.7. In certain embodiments, the heterologous antibody is eluted with a buffer comprising 100 mM glycine, pH 3.

The aspects and embodiments of the invention are further supported by the following non-limiting examples.

EXAMPLES

Abbreviations

| | |
|---|---|
| BCA | Bicinchoninic Acid Assay |
| BLI | Biolayer Interferometry |
| CE | Capillarity Electrophoresis |
| ELISA | Enzyme-Linked Immunosorbent Assay |
| HCP | Host Cell Protein |
| MW | Molecular Weight |
| rpm | Revolutions Per Minute |
| SDS-PAGE | SDS-Polyacrylamide Gel Electrophoresis |
| WB | Western Blot |

Example 1: Sample Preparation

1. Goat Milk

Whole fresh goat milk was heated at 50° C. then centrifuged at 3000 g for 10 min. The flask was cooled in order to solidify the fat. The cream at the top of the flask was removed. Skimmed milk caseins were precipitated at 37° C. by addition of HCl 1M until pH 4.3. Precipitated caseins were removed by centrifugation at 3000 g for 15 min at 20° C.

Total protein concentration was measured by bicinchoninic acid assay (BCA). Proteins were visualized by SDS-polyacrylamide gel electrophoresis (SDS-PAGE). The volume of milk obtained after each step was determined by weighing. The goat antibody concentration was measured by ELISA. Recovery yield (%) was calculated using the following equation:

$$\frac{Cf \times Vf}{Ci \times Vi} \times 100$$

(with Cf=concentration of molecule of interest in the final product which may correspond to skimmed milk, whey or loading sample (g/l), Vf=volume of the final product which may correspond to skimmed milk, whey or loading sample (l), Ci=concentration of molecule of interest in the initial product which correspond to whole milk treated (g/l), Vi=volume of initial product which correspond to whole milk treated (l)).

For 100 ml of whole milk, more than 90 ml of skimmed milk was harvested and more than 80 ml of whey was harvested. After the skimming and caseins precipitation steps, more than 75% of total proteins were removed (Table 1). The comparison between ours results with the available data on proteins milk, confirms the significant loss of proteins after caseins precipitation (Selvaggi et al. (2014) Mol. Biol. Rep. 41:1035-1048). SDS-PAGE analysis for milk sample is reported in Figure.

TABLE 1

Antibodies and proteins recovery for milk samples.
Concentrations of antibodies are measured by ELISA.
Total proteins concentrations are measured by BCA.
Recoveries are calculated as explained in the text.

| Sample | Heterologous antibody recovery (%) | Heterologous antibody purity (%) | Goat IgG recovery (%) | Protein recovery (%) |
|---|---|---|---|---|
| Whole milk | 100 | <10% | 100 | 100 |
| Skimmed milk | >90 | <10% | >90 | ~63 |
| Whey | >80 | >20% | >80 | ~18 |
| Washes of caseins pellet | >5 | >20% | >5 | ~3 |
| Mixture of caseins pellet washes and whey | >85 | >20% | >85 | ~21 |

2. Goat Milk Containing Heterologous Antibody

Whole fresh goat milk containing canine monoclonal heterologous antibody (2 mg/ml) was heated at 50° C. then centrifuged at 3000 g for 10 min. The flask was cooled in order to solidify the fat. The cream at the top of the flask was removed. Skimmed milk caseins were precipitated at 37° C. by addition of HCl 1M until pH 4.3. Precipitated caseins were removed by centrifugation at 3000 g for 15 min at 20° C. The antibodies were mainly found in the supernatant, called whey.

Monoclonal heterologous antibody concentration was measured by enzyme-linked immunosorbent assay (ELISA). Biolayer interferometry (BLI) assay confirmed results obtained by ELISA. Total protein concentration was measured by bicinchoninic acid assay (BCA). Proteins were visualized by SDS-polyacrylamide gel electrophoresis (SDS-PAGE). The goat antibody concentration was measured by ELISA. The volume of milk obtained after each step was determined by weighing. Recovery is defined as the amount of molecule of interest that can be retrieved after processing. Usually expressed as a percentage of starting material or yield. Recovery yield (%) was calculated using the following equation:

$$\frac{Cf \times Vf}{Ci \times Vi} \times 100$$

(with Cf=concentration of molecule of interest in the final product which may correspond to skimmed milk, whey or loading sample (g/l), Vf=volume of the final product which may correspond to skimmed milk, whey or loading sample (l), Ci=concentration of molecule of interest in the initial product which correspond to whole milk treated (g/l), Vi=volume of initial product which correspond to whole milk treated (l)).

Goat milk containing heterologous antibody behaved like goat milk without heterologous antibody. Indeed, the skimming and caseins precipitation were performed in the identical conditions to those in example 1.1 and the results were identical to those in example 1.1: i) the same volumes of skimmed milk and whey were recovered, ii) the same quantities of total proteins were removed and iii) the same quantities of goat IgG were recovered.

For 1 l of whole milk containing 2 mg/ml heterologous antibody, more than 80% of heterologous antibody was harvested in whey. The goat IgG recovery yield was similar. Heterologous antibody and goat IgG recovery yields after each step are reported in Table 1.

a) Caseins Pellet Washes

Whole fresh goat milk containing canine monoclonal heterologous antibody (2 mg/ml) was heated at 50° C. then centrifuged at 3000 g for 10 min. The flask was cooled in order to solidify the fat. The cream at the top of the flask was removed. Skimmed milk caseins were precipitated at 37° C. by addition of HCl 1M until pH 4.3. Precipitated caseins were removed by centrifugation at 3000 g for 15 min at 20° C. Pellet was washed 3 times using 5% initial milk volume of 50 mM sodium acetate, 50 mM NaCl at pH 4.3 in order to harvest residual heterologous antibody present in caseins pellet. Washes and whey were mixed, adjusted to pH 6 with NaOH 1M and filtered 2 times through 3 μm and 0.22 μm respectively before the loading on the matrix. The mixture of whey and washes is named "loading sample" in the following examples.

Figure 2A:
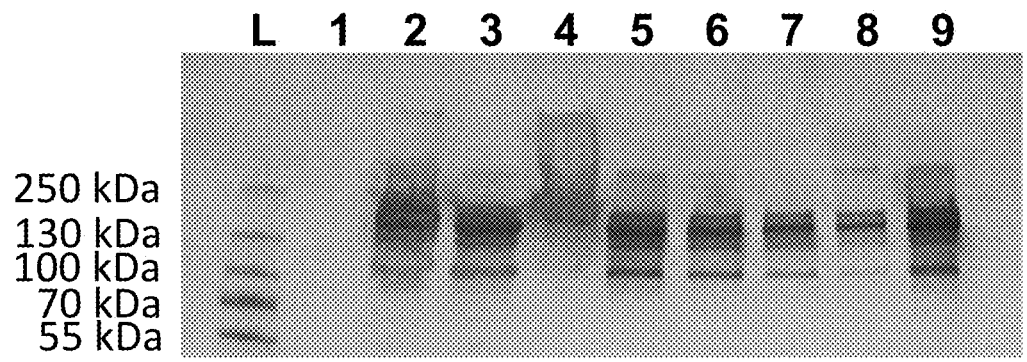
FIGS. 2A and 2B: Western blot anti-dog antibodies (FIG. 2A) and SDS-PAGE analysis (FIG. 2B) for milk samples. 20 µL of sample diluted 4 times were loaded on the gel. Sample description is presented in Table 2.
Figure 2B:
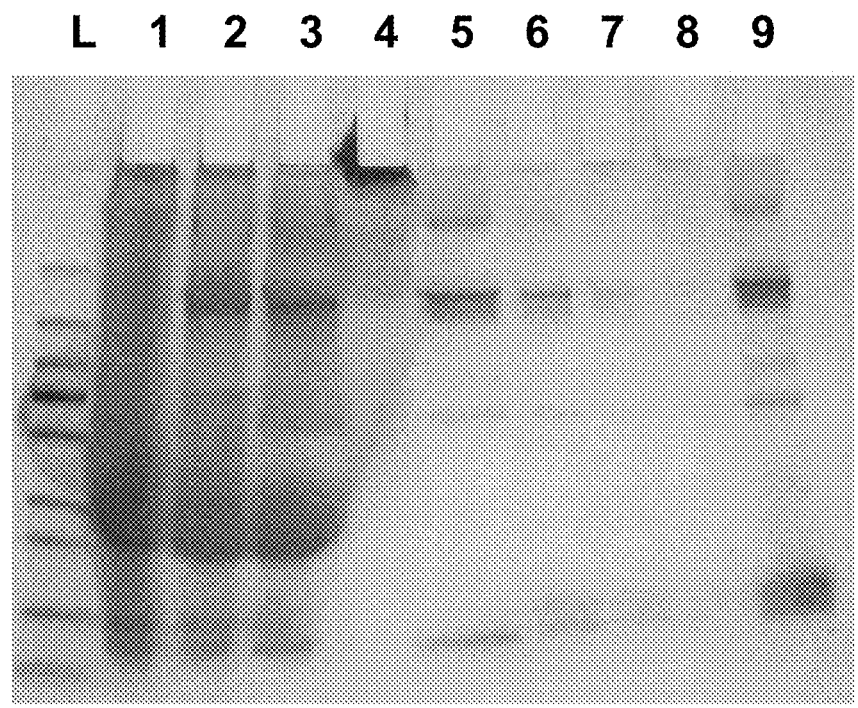

Monoclonal heterologous antibody concentration was measured by enzyme-linked immunosorbent assay (ELISA). Biolayer interferometry (BLI) assay confirmed results obtained by ELISA. Total protein concentration was measured by bicinchoninic acid assay (BCA). Proteins were visualized by SDS-polyacrylamide gel electrophoresis (SDS-PAGE) (FIG. 2B). Monoclonal heterologous antibody were visualized by western Blot (FIG. 2A). The goat antibody concentration was measured by ELISA. The volume of milk obtained after each step was determined by weighing. Recovery yield (%) was calculated using the following equation:

$$\frac{Cf \times Vf}{Ci \times Vi} \times 100$$

(with Cf=concentration of molecule of interest in the final product which may correspond to skimmed milk, whey or loading sample (g/l), Vf=volume of the final product which may correspond to skimmed milk, whey or loading sample (l), Ci=concentration of molecule of interest in the initial product which correspond to whole milk treated (g/l), Vi=volume of initial product which correspond to whole milk treated (l)).

TABLE 2

Sample description of FIG. 2

| Well n° | Sample | Dilution |
|---|---|---|
| 1 | Whole milk Ctrl | 1/4 |
| 2 | Whole milk heterologous antibody 1 g/l | 1/4 |
| 3 | Skim milk heterologous antibody 1 g/l | 1/4 |
| 4 | Cream heterologous antibody 1 g/l | 1/4 |
| 5 | Whey heterologous antibody 1 g/l | 1/4 |
| 6 | Precipitate wash 1 | 1/4 |
| 7 | Precipitate wash 2 | 1/4 |
| 8 | Precipitate wash 3 | 1/4 |
| 9 | Filtered whey heterologous antibody 1 g/l | 1/4 |

Goat milk containing heterologous antibody behaved like goat milk without heterologous antibody. Indeed, the skimming and caseins precipitation were performed in the identical conditions to those in example 1.1 and the results were identical to those in example 1.1: i) the same volumes of skimmed milk and whey were recovered, ii) the same quantities of total proteins were removed and iii) the same quantities of goat IgG were recovered.

For 1 l of whole milk containing 2 mg/ml heterologous antibody, more than 80% of heterologous antibody was harvested in whey. More than 5% of heterologous antibodies were recovered by washing the caseins pellet. So, in total, more than 85% of antibodies were recovered in mixture of whey and washes. The goat IgG recovery yield was similar. Heterologous antibody and goat IgG recovery yields after each step are reported in Table 1.

Example 2: Skimming

1. Creamer Separator

Examples 1.1 and 1.2 were repeated, but the skimming of whole milk was carried out with a creamer separator at 10.500±1000 rpm (output of 100 l/h). The creamer separator directly removes the cream of whole heated milk without a cooling step.

The results are identical to those in example 1.1 et 1.2 respectively.

2. Heating Temperature

Example 1.2 was repeated, but the whole milk was heated at 75° C. for 10 sec before the skimming. The heterologous antibody recovery was drastically less than in example 1.2.

The skimmed milk exhibited a 100-fold decreased heterologous antibody concentration. Similar result obtained for goat antibody showed that antibodies were not stable at high temperature. Therefore, skimming should be performed under 75° C.

3. Heating Time

Example 1.2 was repeated, but the whole milk was heated at 50° C. for 60 min before the skimming. The results were identical to those in example 1.2. So, the recovery yield identical to example 1.2 shows that the antibodies do not denature at 50° C.

Example 3: Caseins Precipitation

1. Type of Acids

Example 1.2 was repeated, but the caseins precipitation was carried out with citric acid 1M.

The results were identical to those in example 1.2.

2. Concentration of the Acid

Example 1.2 was repeated, but the caseins precipitation was carried out using 0.1, 0.2, 0.5 or 1N HCl. The results were identical to those in example 1.2.

3. pH for Caseins Precipitation

Example 1.2 was repeated, but the caseins precipitation was carried out with HCl 1M until a pH adjusted from 6.7 to 2.6. Starting pH without HCl is 6.7. The pH tested were 6.4, 5.8, 5.3, 5.0, 4.6, 4.5, 4.4, 4.3, 4.2, 4.1, 4.0, 3.8, 3.2 and 2.6. The analytical assays were carried out as in Example 1.2.

Figure 3:
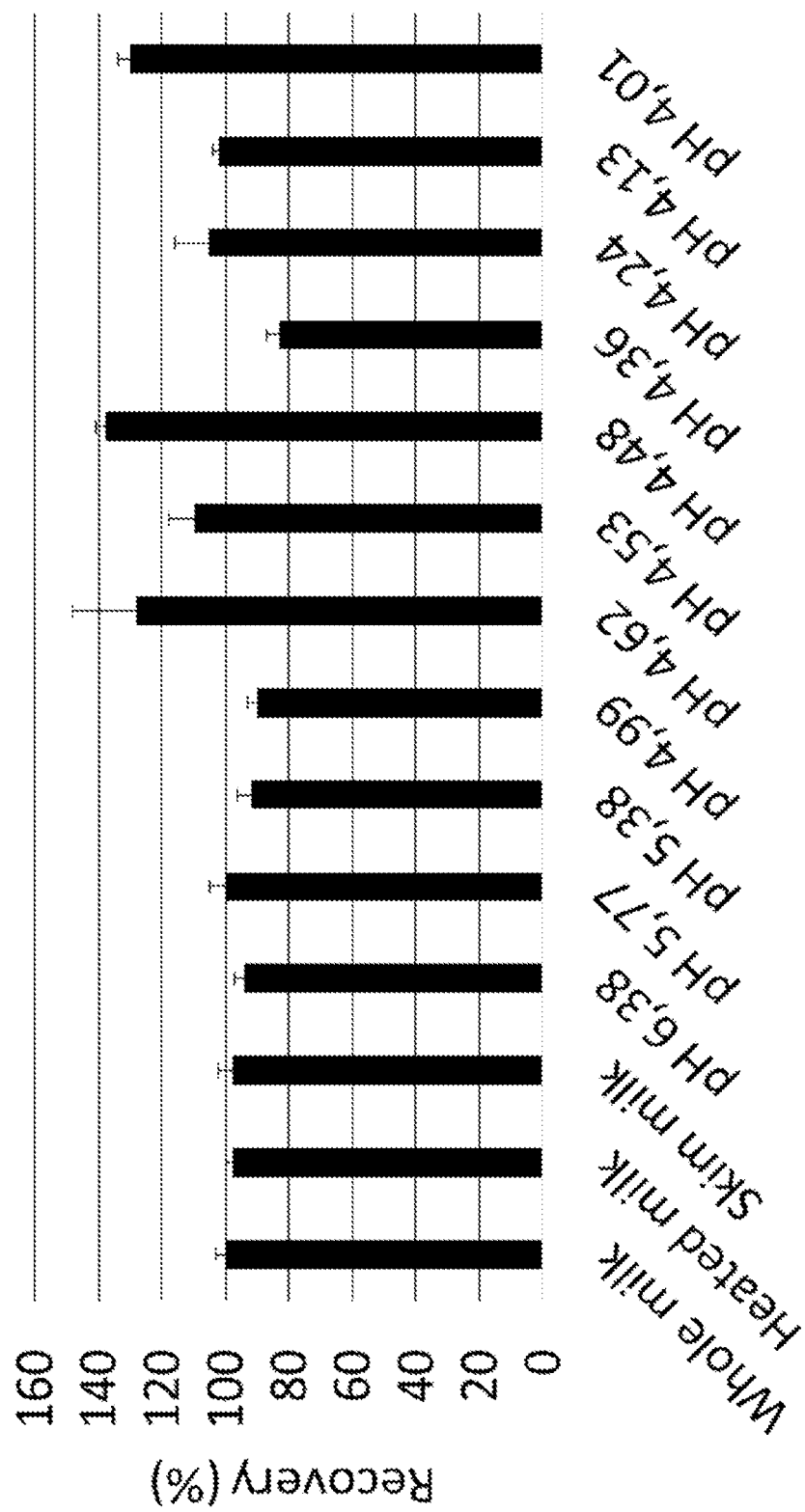
FIG. 3: pH effect on heterologous antibody in goat milk. HCl was added to skimmed milk in order to decrease the pH which precipitates proteins. Precipitated proteins were removed by centrifugation. Heterologous antibody in supernatant was measured by ELISA.
Figure 4:
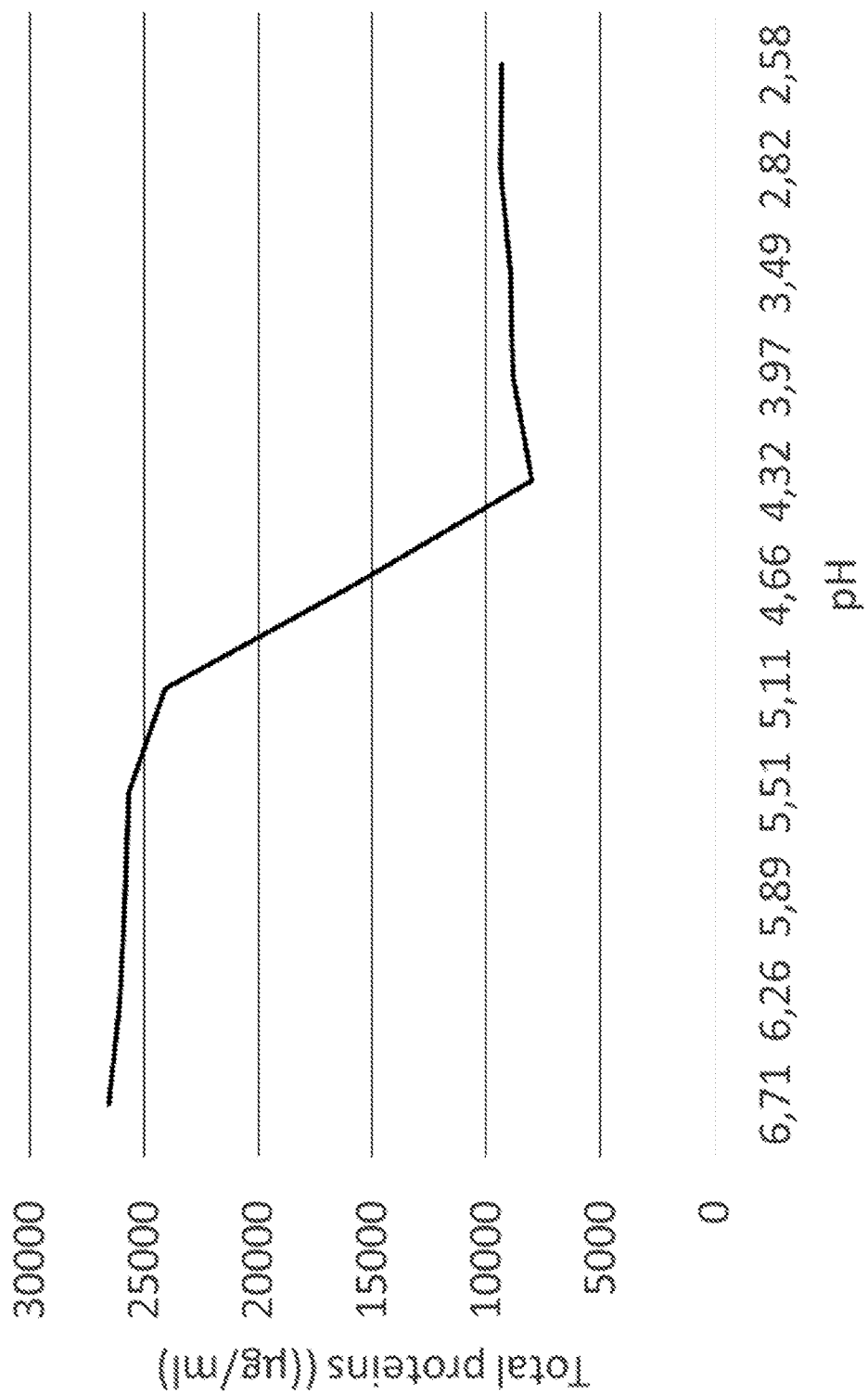
FIG. 4: pH effect on total protein content in goat milk. HCl was added to skimmed milk in order to decrease the pH which will precipitate proteins. Precipitated proteins were removed by centrifugation. Total protein in supernatant was measured by BCA.
Figure 5:
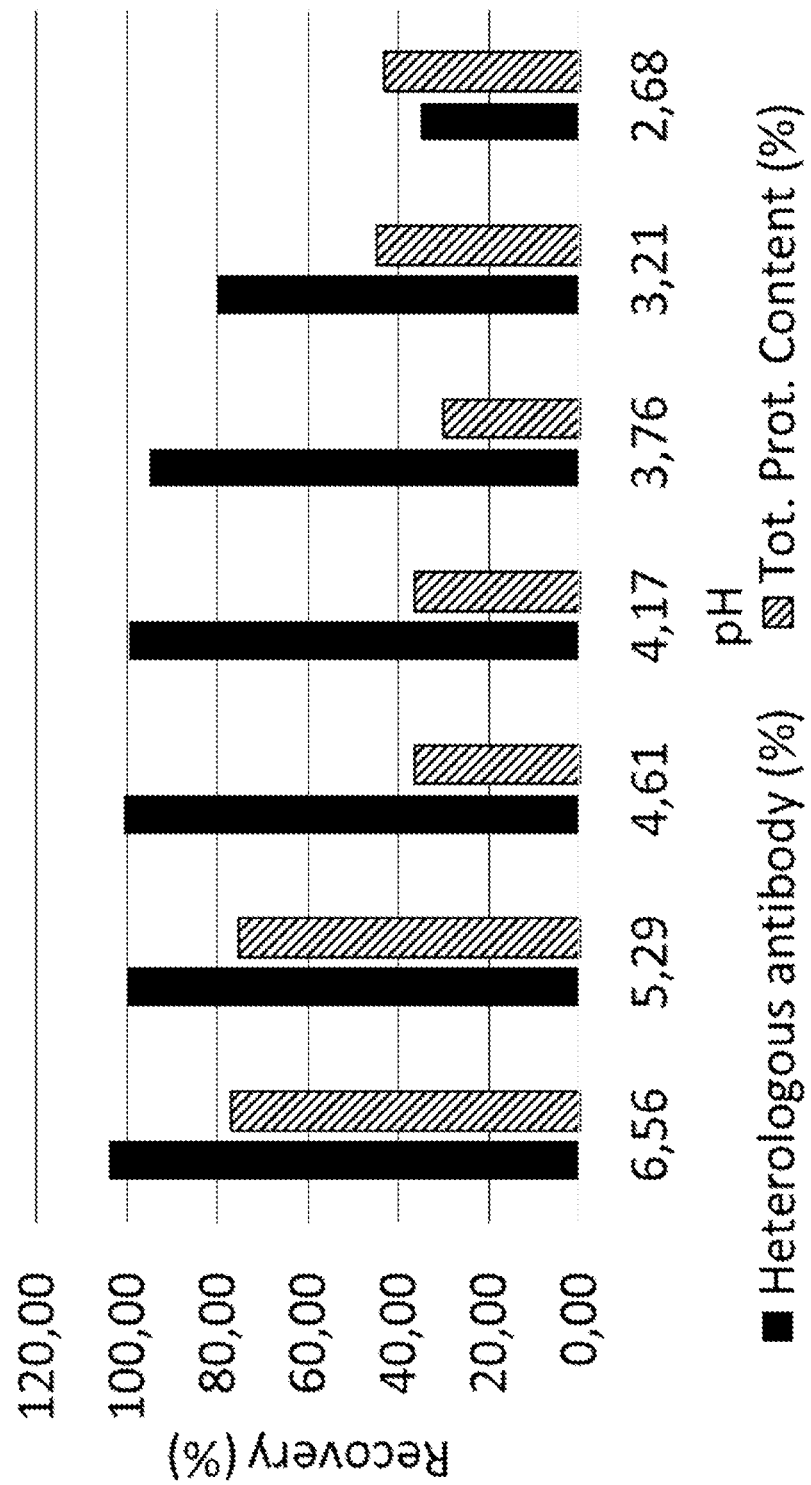
FIG. 5: pH effect on total protein content (right bars) and heterologous antibody (left bars) in goat milk. HCl was added to skimmed milk in order to decrease the pH which precipitates proteins. Precipitated proteins were removed by centrifugation. Total protein in supernatant was measured by BCA. Heterologous antibody in supernatant was measured by ELISA.

Caseins were totally removed from pH 4.3 to 2.6. The heterologous antibody recovery after precipitation was similar whatever the pH used (FIG. 3), up to about pH 4. Under about pH 4 a decrease in heterologous antibody recovery was observed (FIG. 5). The results were identical to those in example 1.2 for pH adjusted to a pH ranging from 4.3 to 2.6 (FIG. 4). Tables 3-5 correspond to FIGS. 3-5.

TABLE 3

| Sample | Target Recovery (%) | SD |
|---|---|---|
| Raw milk | 100 | 3 |
| Heated milk | 98 | 2 |
| Skim milk | 99 | 4 |
| pH 6.38 | 93 | 3 |
| pH 5.77 | 99 | 5 |
| pH 5.38 | 91 | 4 |
| pH 4.99 | 89 | 3 |
| pH 4.62 | 128 | 20 |
| pH 4.53 | 109 | 8 |
| pH 4.48 | 138 | 2 |
| pH 4.36 | 84 | 4 |
| pH 4.24 | 105 | 11 |
| pH 4.13 | 104 | 3 |
| pH 4.01 | 130 | 5 |

TABLE 4

| pH | Total protein content (µg/ml) |
|---|---|
| 6.71 | 26548 |
| 6.26 | 26035 |
| 5.89 | 25842 |
| 5.51 | 25658 |
| 5.11 | 24095 |
| 4.66 | 15746 |
| 4.32 | 8002 |
| 3.97 | 8820 |
| 3.49 | 8971 |
| 2.82 | 9362 |
| 2.58 | 9349 |

TABLE 5

| pH | Heterologous antibody (%) | Tot. Prot. Content (%) |
|---|---|---|
| 6.56 | 104 | 77 |
| 5.29 | 100 | 75 |
| 4.61 | 101 | 37 |
| 4.17 | 99 | 37 |
| 3.76 | 95 | 30 |
| 3.21 | 80 | 45 |
| 2.68 | 35 | 43 |

4. Caseins Precipitation Using Ammonium Sulfate a) Determination of the Ammonium Sulfate Concentration for Caseins Precipitation.

Whole fresh goat milk was skimmed as in the example 1.1. 10 ml of skimmed milk was buffered using 1.3 ml of 1.5 M TRIS-HCl at pH 7. Then, various amounts of ammonium sulphate were added to the skimmed milk (0, 20, 30, 45, 60, 75 and 95%). Mixture was mixed for 10 min at room temperature. Precipitate was removed by centrifugation for 10 min at 10000 g. Supernatant was analyzed by SDS-PAGE (FIG. 6).

Figure 6:
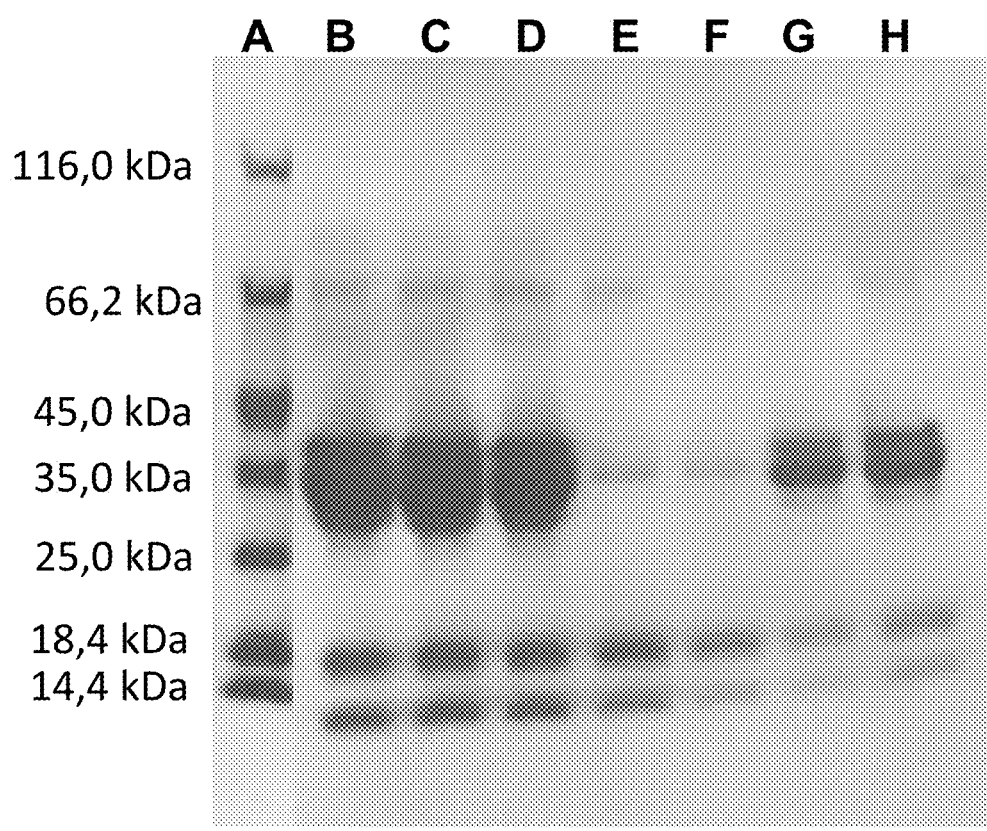
FIG. 6: SDS-PAGE analysis of the caseins precipitation by adding ammonium sulfate in the skimmed milk. 10 µL of supernatant diluted 20 times were loaded on the gel. Well A. Pierce Unstained Protein Molecular Weight Marker (Thermo Scientific, Rockford, USA). Well B. Skimmed Milk. Skimmed milk contains mainly Caseins (MW 19 to 25 kDa), α-lactalbumin (MW≈18 kDa) and β-lactoglobulin (MW≈14 Kda). Well C. Supernatant of skimmed milk containing 20% of ammonium sulfate. Well D. Supernatant of skimmed milk containing 30% of ammonium sulfate. Well E. Supernatant of skimmed milk containing 45% of ammonium sulfate. Well F. Supernatant of skimmed milk containing 60% of ammonium sulfate. Well G. Supernatant of skimmed milk containing 75% of ammonium sulfate. Well H. Supernatant of skimmed milk containing 95% of ammonium sulfate.

Caseins precipitated by adding 45 and 60% of ammonium sulfate (FIG. 6).

b) Determination of the Ammonium Sulfate Concentration for Caseins Precipitation without that of Antibody.

The above example was carried out, but whole fresh goat milk containing canine monoclonal heterologous antibody (0.5 g/l) was processed. The test was carried out by adding intermediate ammonium sulfate concentrations to those employed above (30, 35, 40, 45, 50, 55, 60, 65, 70 and 75%). Heterologous antibody concentration in supernatant was measured by ELISA.

Precipitates were observed for concentrations of ammonium sulphate between 45 and 70%. However, ELISA revealed that heterologous antibody also precipitated at these concentration of ammonium sulfate. Results show no conditions for precipitating the caseins without precipitating the antibodies of interest. The caseins precipitation using ammonium sulfate was excluded for the process due to the loss of heterologous antibody in the pellet of caseins.

Example 4: Chromatography Optimization Experiment

1. Resin Selection
a) Mixed-Mode Resin
CMM hyperCel™ Mixed-Mode Sorbent

Example 1.2 was repeated for the sample preparation except that the mixture of whey and washes was adjusted either to pH 4, 5 or 6. Purification of heterologous antibody was carried out using mixed-mode resin and adapted buffers. CMM hyperCel™ Mixed-mode sorbent (PALL) was contained in Acroprep Advance 96 well filter plates (PALL) to purify heterologous antibody by batch mode. Resin was washed two times with 2 resin volumes of equilibration buffer (50 mM sodium acetate at pH 4, 5 or 6). Buffer was removed by centrifugation at 500 g for 2 min. 2 bed volumes of sample was mixed for 60 min with the matrix. The flow through was removed by centrifugation at 500 g for 2 min. The resin was washed twice by incubation of 4 bed volumes using equilibration buffer with resin for 5 min followed by centrifugation at 500 g for 2 min. Retained proteins were successively eluted with 50 mM Tris-HCl at pH ranging from pH 7 to 9.5 (7, 7.5, 8, 8.5, 9 and finally 9.5) as follows: 4 bed volumes of buffer were incubated with resin for 10 min followed by centrifugation at 500 g for 2 min. Each elution was collected as a separate fraction. Each elution corresponding at 4 bed volumes was collected as a separate fraction.

Monoclonal heterologous antibody concentration was measured by enzyme-linked immunosorbent assay (ELISA) and results were confirmed by biolayer interferometry (BLI). Purity was estimated by capillarity electrophoresis (CE) and calculated using the following equation:

$$\frac{Ca}{Ct} \times 100$$

(with Ca=antibody concentration in the sample (g/l) and Ct=total protein concentration in the sample (g/l)). Heterologous antibody visualization was performed by western Blot (WB). The residual goat antibody in the final product was measured by ELISA. Recovery yield (%) was calculated using the following equation:

$$\frac{Cf \times Vf}{Ci \times Vi} \times 100$$

(with Cf=concentration of the molecule of interest in the final product (g/l), Vf=volume of the final product (l), Ci=concentration of the molecule of interest in the initial product which correspond to loading sample (g/l), Vi=volume of the initial product which correspond to loading sample (l)).

In our experimental conditions, the used matrix bound heterologous and goat antibodies with a maximum at pH 5. Heterologous Antibody were mainly eluted at pH 8. Purity and yield of heterologous antibody in this fraction were evaluated at 50% and 75% respectively. However, around 40% of goat IgG were also eluted at pH 8 and stayed in the final product. In our experimental conditions, goat and heterologous antibodies could not be separated.

Loading pH

During the first trial we tested the equilibration and the washes at pH 4, 5 and 6 but the better recoveries were observed at pH 5 so for the second trial we used border pH values: 5, 5.5-6-6.5. Example 4.1.a was repeated but equilibration and washes were carried out using 50 mM sodium acetate at pH 5, 5.5, 6 or 6.5.

The results were similar to those in above example. However, purity and yield of heterologous antibody were better when the equilibration was performed at pH 5. Indeed, at pH >5, a part of heterologous antibody was harvested in flow through certainly due to its pI at 6.5.

b) Cationic Resin
HyperCel™ Star CEX cation exchange sorbent

Example 4.1.a was repeated but purification of heterologous antibody was carried out using cationic resin and adapted buffers. Used resin was hyperCel™ Star CEX cation exchange sorbent (PALL). The equilibration and washes were carried out using 50 mM sodium acetate, 50 mM NaCl at pH 3.5, 4.5, and 5.5. Retained proteins were successively eluted with 50 mM Tris-HCl at the same pH as for equilibration but containing NaCl from 200 mM to 700 mM (200, 300, 400, 500, 600 and finally 700 mM). Volumes for each step were identical to those in above example. The analytical assays were carried out as in Example 4.1.a.

In our experimental condition, the used matrix bound the whole of heterologous antibody and a part of goat antibodies with a maximum at pH 5.5. Goat IgG were mainly eluted using 200 mM and 300 mM NaCl whereas heterologous antibody were eluted using NaCl concentration between 200 and 400 mM. The heterologous antibody purity was better for the elution fraction at 300 mM and was estimated at 76%. Nevertheless, less than 45% of heterologous antibody was recovered in this fraction. In consequence, parameters for a high yield and purity of heterologous antibody and a separation of the two kinds of antibodies were not determined for this resin.

Loading pH

The above Example was repeated but equilibration and washes were carried out using 50 mM sodium acetate at pH 5.5, 6 or 6.5. Purity and yield of heterologous antibody were worse than those in above example. Indeed, when equilibration pH was increased, matrix bound less heterologous antibody due to its pI at around 6.5.

c) Anionic Resin
HyperCel™ Star AX Ion Exchange Sorbent

Example 4.1.b was repeated but purification of heterologous antibody was carried out using anionic resin and adapted buffers. Used resin was hyperCel™ Star AX Ion exchange sorbent (PALL). Furthermore, sample was adjusted at pH 7.5 and diluted 2 times in equilibration buffer. The equilibration and washes were carried out using 50 mM Tris-HCl at pH 7.5. Retained proteins were successively eluted with 50 mM Tris-HCl at pH 7.5 containing NaCl from 300 mM to 1000 mM (300, 500 and 1000 mM). Volumes for each step were identical to those example 4.1.b. The analytical assays were carried out as in Example 4.1.b.

In our experimental conditions, the used matrix bound around 75% of loaded heterologous antibody. Heterologous antibody was mainly eluted using 300 mM NaCl. Yield was not enough satisfying for this matrix.

Loading pH

Example was repeated but equilibration and washes were carried out using pH 8 or 8.5.

The results were similar to those in above example. Increasing the loading pH didn't improve the binding of heterologous antibody on the matrix. Tests using a pH less than 7.5 were not carried out because pI of the heterologous antibody is about 6.5.

d) Affinity Resin

MabSelectSure (GE)—Protein-A

Example 4.1.a. was repeated but purification of heterologous antibody was carried out using Protein-A Mabselect-Sure (GE Healthcare). The equilibration and washes were carried out using 20 mM sodium phosphate at pH 6. Retained proteins were successively eluted with 100 mM sodium citrate at pH from pH 6 to 2 (6, 5, 4, 3, 2.5 and 2). Volumes for each step were identical to those in above example. The analytical assays were carried out as in Example 4.1.b.

More than 80% of goat antibodies loaded were harvested in the flow through and washes. Around 5 and 10% of goat antibodies loaded were harvested in the first and second elution respectively (elutions at pH 6 and 5). Conversely, less than 1% heterologous antibody loaded was harvested in the flow through and washes. 9 and 90% of heterologous antibody loaded was harvested in the second and third elution respectively (elution at pH 5 and 4). The purity of heterologous antibody in the third fraction was estimated at 55%.

Comparison of the four above resins showed that protein-A matrix is the better candidate for our heterologous antibody purification. Indeed, affinity chromatography has the following advantages: protein-A binds heterologous antibody and weakly goat IgG. Then goat IgG could be eluted at pH less acid than heterologous antibody. Thanks to chromatography using protein-A for the goat and heterologous antibody separation. Furthermore, milk proteins aren't bound to protein-A matrix so the purity of harvested heterologous antibody is high. Optimization of purification by affinity chromatography was developed in the following sections.

2. Parameter Selection a) Elution

Linear Gradient

Figure 7:
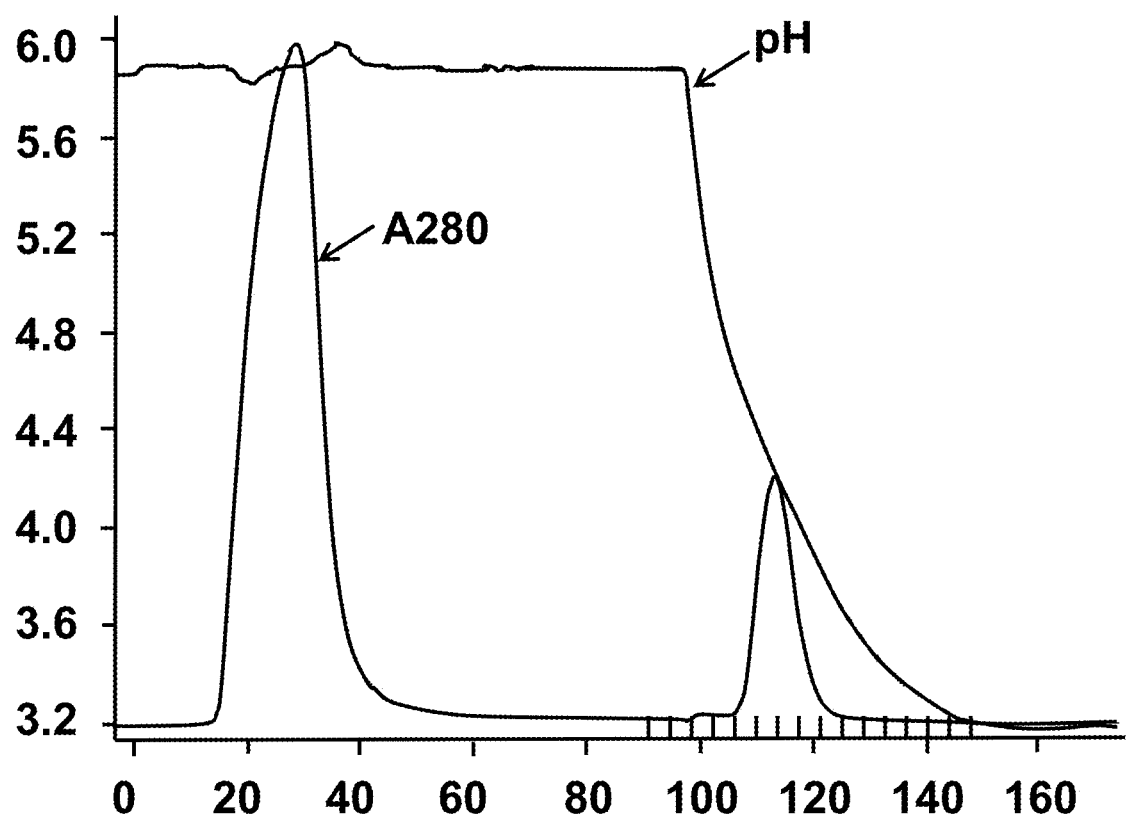
FIG. 7: Chromatogram of the purification by affinity chromatography. The absorbance at 280 nm at the outlet of the column and the pH are represented respectively by lines as indicated. The fractions and fraction numbers are indicated. The sample was loaded onto the column (Praesto, Purolite) and then the column was washed with the equilibration buffer at pH 6. Proteins which were not bound to the column were recovered in the flow through and wash fraction. A linear gradient of pH 6 to 3 was applied and the elution is recovered in 15 fractions.
Figure 8:
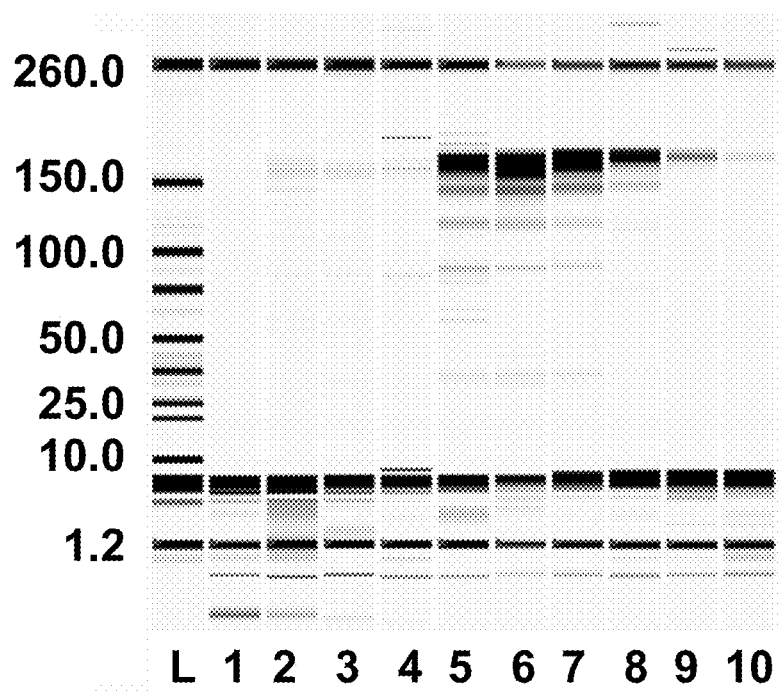
FIG. 8: EC analysis of the purification fractions. Fractions from 6 to 11 contained mainly heterologous antibody (MW z 150 kDa).
Figures 9A, 9B, 9C, 9D, 9E, 9F:
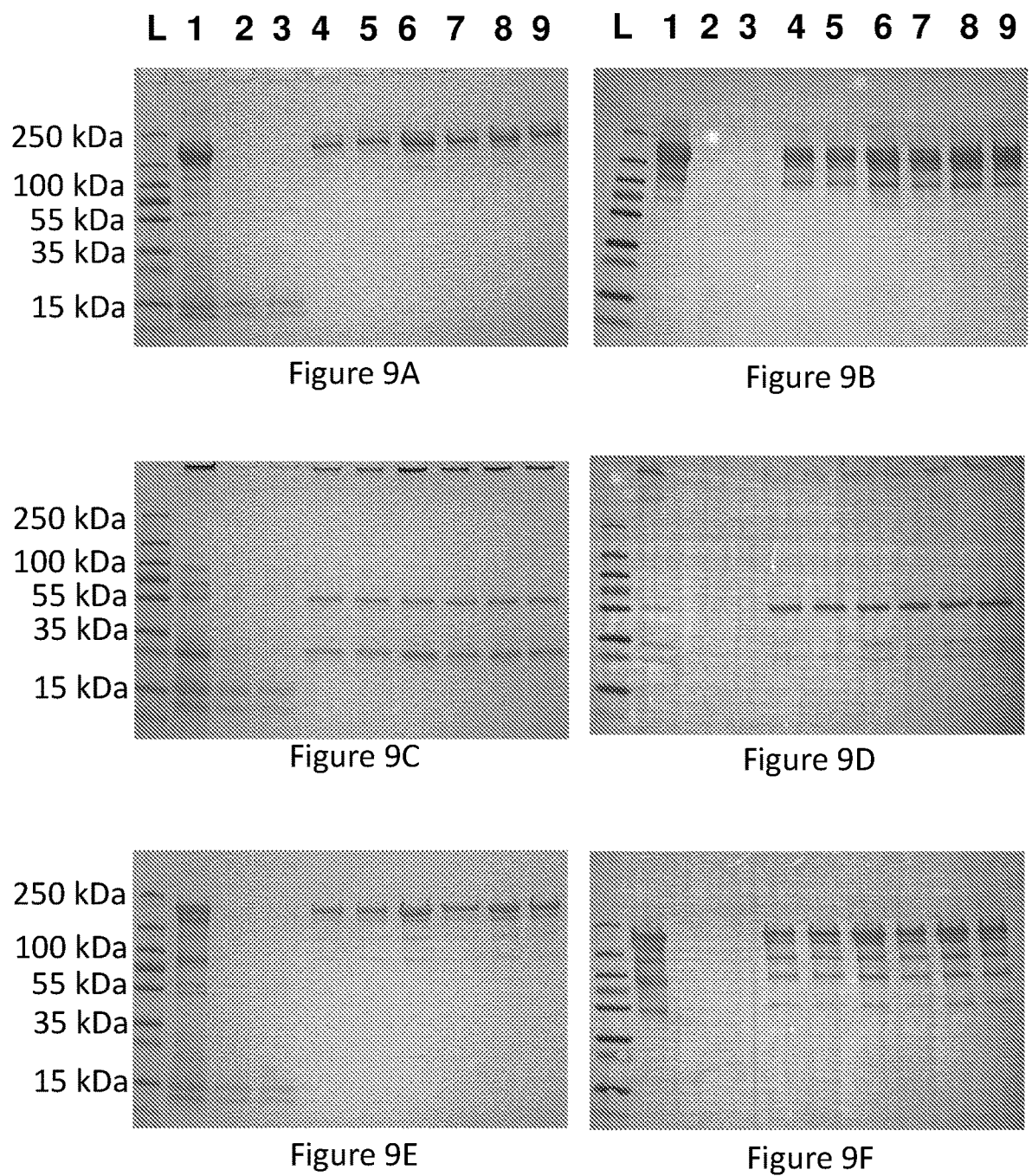
FIGS. 9A-9F: SDS-PAGE (left (FIGS. 9A, 9D, and 9E)) and WB analysis (right (FIGS. 9B, 9C, and 9F)) of the purification fractions. 20 µL of supernatant diluted 4 times was loaded on the gel that was realized in denaturing-reducing (top (FIGS. 9A and 9B)), denaturing (middle (FIGS. 9C and 9D)) and native (bottom (FIGS. 9E and 9F)) conditions. Well L. Page Ruler Plus Prestained Ladder (Thermo Fischer, Rockland, USA). Well 1. Whey in acetate buffer with heterologous antibody. Well 2. Purification flowthrough and wash steps (Praesto column, Purolite). Well 3. Purification flowthrough and wash steps (MabSelectSure column, GE Healthcare). Well 4. Elution pool (Praesto column, Purolite). Well 5. Elution pool (MabSelectSure column, GE Healthcare). Well 6. Elution fraction 7 (Praesto column, Purolite). Well 7. Elution fraction 8 (Praesto column, Purolite). Well 8. Elution fraction 6 (MabSelectSure column, GE Healthcare). Well 9. Elution fraction 7 (MabSelectSure column, GE Healthcare).

Example 1.2 was repeated for the sample preparation. Purification of heterologous antibody was carried out by affinity chromatography using 5 ml cartridge containing protein-A (MabselectSure, GE Healthcare). Run was performed at a flow rate of 6 ml/min as followed: 1 column volume (CV) of the sample diluted 2 times in equilibration buffer was loaded on cartridge equilibrated in 50 mM sodium acetate, 50 mM NaCl at pH 6.0. Cartridge was washed with 10 CV with equilibration buffer. Elution was performed with a linear gradient of 10 CV between equilibration buffer and 0.1 M citrate at pH 3. Heterologous antibody was collected by fraction corresponding to 1 CV and neutralized in 1M Tris-HCl at pH 9.0 to a pH stabilizing antibody. Chromatogram is reported in FIG. 7 and the analysis of fractions 2 to 11 by EC is reported at FIG. 8. Fractions having the heterologous antibody were pooled. Proteins and heterologous antibody of loading sample, flow through+wash and pooled fractions are analysed by SDS-PAGE and WB (FIG. 9)

Monoclonal heterologous antibody concentration was measured by enzyme-linked immunosorbent assay (ELISA) and results were confirmed by biolayer interferometry (BLI). Purity was estimated by capillarity electrophoresis (CE) and calculated using the following equation:

$$\frac{Ca}{Ct} \times 100$$

(with Ca=antibody concentration in the sample (g/l) and Ct=total protein concentration in the sample (g/l)). The residual goat antibody in the final product was measured by ELISA. Recovery yield (%) was calculated using the following equation:

$$\frac{Cf \times Vf}{Ci \times Vi} \times 100$$

(with Cf=concentration of the molecule of interest in the final product (g/l), Vf=volume of the final product (l), Ci=concentration of the molecule of interest in the initial product which correspond to loading sample (g/l), Vi=volume of the initial product which correspond to loading sample (l)).

More than 93% of goat antibodies loaded were harvested in the flow through and washes. Around 4% of goat antibodies loaded were harvested in the first part of elution at pH >4.8. Conversely, heterologous antibody having high affinity for protein-A resin was weakly lost in the flow through, washes and first part of elution. 75% of the monoclonal antibody was harvested in the second part of elution at pH <4.8 with a purity >90% (FIG. 8, fractions 6 to 10). These results show that goat IgG and heterologous antibody can be separated using different pH. This is why step pH gradient was tested at the following example.

This above example was repeated using Protein-A Praesto AP resin (Purolite). Results were identical to those in above example.

TABLE 6

Sample description of FIG. 9

| Sample # | Samples | Dilution |
| --- | --- | --- |
| 1 | Whey acetate + heterol. Ab 2 mg/ml | 1/4 |
| 2 | FT + wash: PA Purolite | 1/4 |
| 3 | FT + wash: PA GE MabSelect sure | 1/4 |
| 4 | Pool eluate PA Purolite | 1/4 |
| 5 | Pool eluate PA GE MabSelect sure | 1/4 |
| 6 | Fraction 7 PA Purolite | 1/4 |
| 7 | Fraction 8 PA Purolite | 1/4 |
| 8 | Fraction 6 PA Mabselect Sure | 1/4 |
| 9 | Fraction 7 PA Mabselect Sure | 1/4 |

Steps Gradient 4 steps gradient (pH 6.0, pH 4.8, pH 3.5 and pH 3.0)

Figure 10:
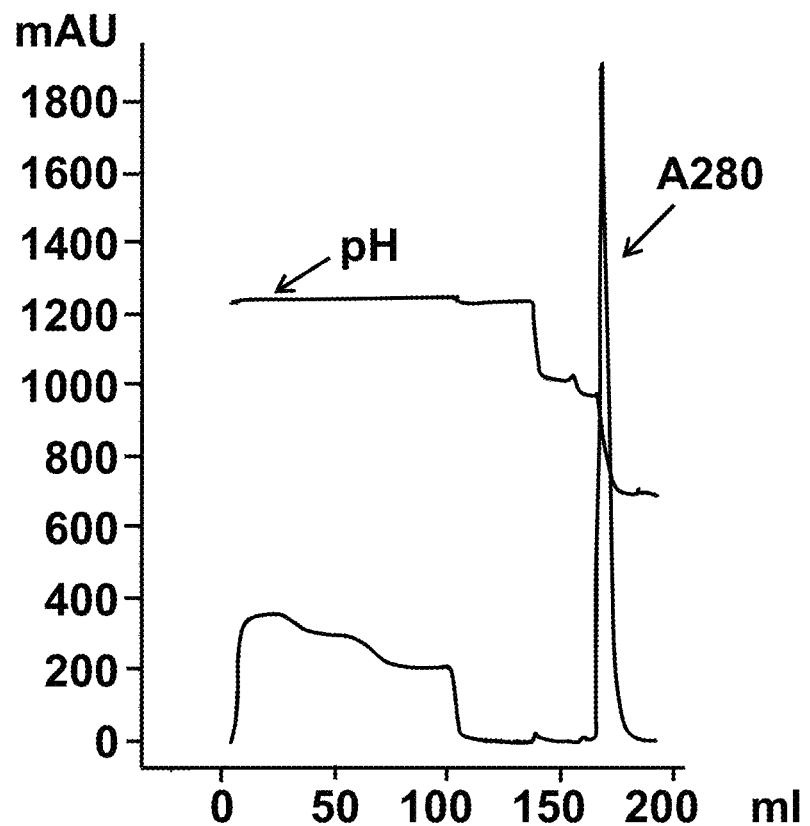
FIG. 10: Chromatogram of the purification by affinity chromatography. The absorbance at 280 nm at the outlet of the column and the pH are represented respectively by the lines as indicated. The sample is loaded onto the column and then the column is washed with the equilibration buffer at pH 6. Proteins which are not bind to the column are recovered in the flow through and wash fraction. Step gradients at pH 4.8, 3.5 and 3 are applied.

In order to better separate goat IgG and heterologous antibody, elution was performed using 4 steps of pH. The above example was repeated but run was performed as follows: 20 column volumes (CV) of the sample (constituted of 17 ml of whey with 2 mg/ml heterologous antibody and reached to pH 6 with 100 ml acetate 1M pH 7.5) was loaded on cartridge equilibrated in 50 mM sodium acetate, 50 mM NaCl at pH 6.0. Cartridge was washed with 10 CV with equilibration buffer. A first elution was performed using 5 CV of 50 mM sodium acetate, 50 mM NaCl at pH 4.8. The second elution was performed using 5 CV of 50 mM sodium acetate, 50 mM NaCl at pH 3.5. Finally, the third elution was performed using 5 CV of 50 mM sodium acetate, 50 mM NaCl at pH 3.0. Heterologous antibody were collected by fraction corresponding to 1 CV and neutralized in 1M Tris-HCl at pH 9.0 to a pH stabilizing antibody. Fractions having the heterologous antibody were pooled. Heterologous antibody were dialyzed against 50 mM acetate, 50 mM NaCl at pH 6 through 30 kDa membrane. Analytical assays were similar to those in above example. Chromatogram is reported in FIG. 10.

In our experimental conditions, more than 90% of goat antibodies loaded were harvested in the flow through and washes. Around 4% of goat antibodies loaded were harvested in the first elution at pH 4.8. Conversely, heterologous antibody having high affinity for protein-A resin was weakly lost in the flow through, wash and first elution (less than 5%). The monoclonal antibody was harvested in the second elution at pH 3.5.

Figure 11A:
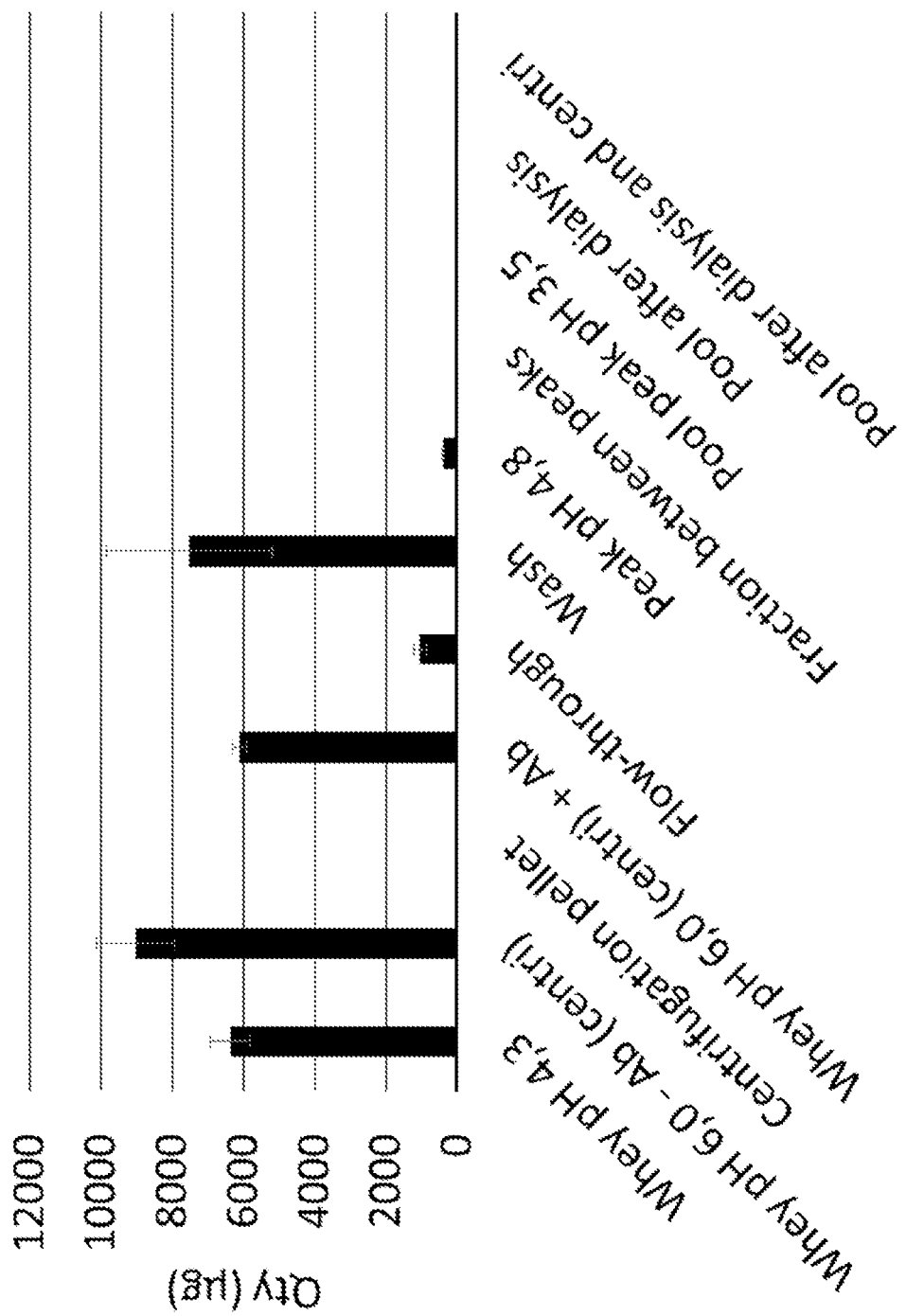
FIGS. 11A and 11B: ELISA results with processed samples on two types of PA resins. Goat IgG (FIG. 11A) and heterologous antibody (FIG. 11B) concentrations were determined in different samples obtained during their processing, i.e the whey at pH 4.3, pH 6.0 (with and without antibody) and samples obtained during purification on Praesto resin (flowthrough/washes, eluate pools and the major fraction, dialyzed sample)
Figure 11B:
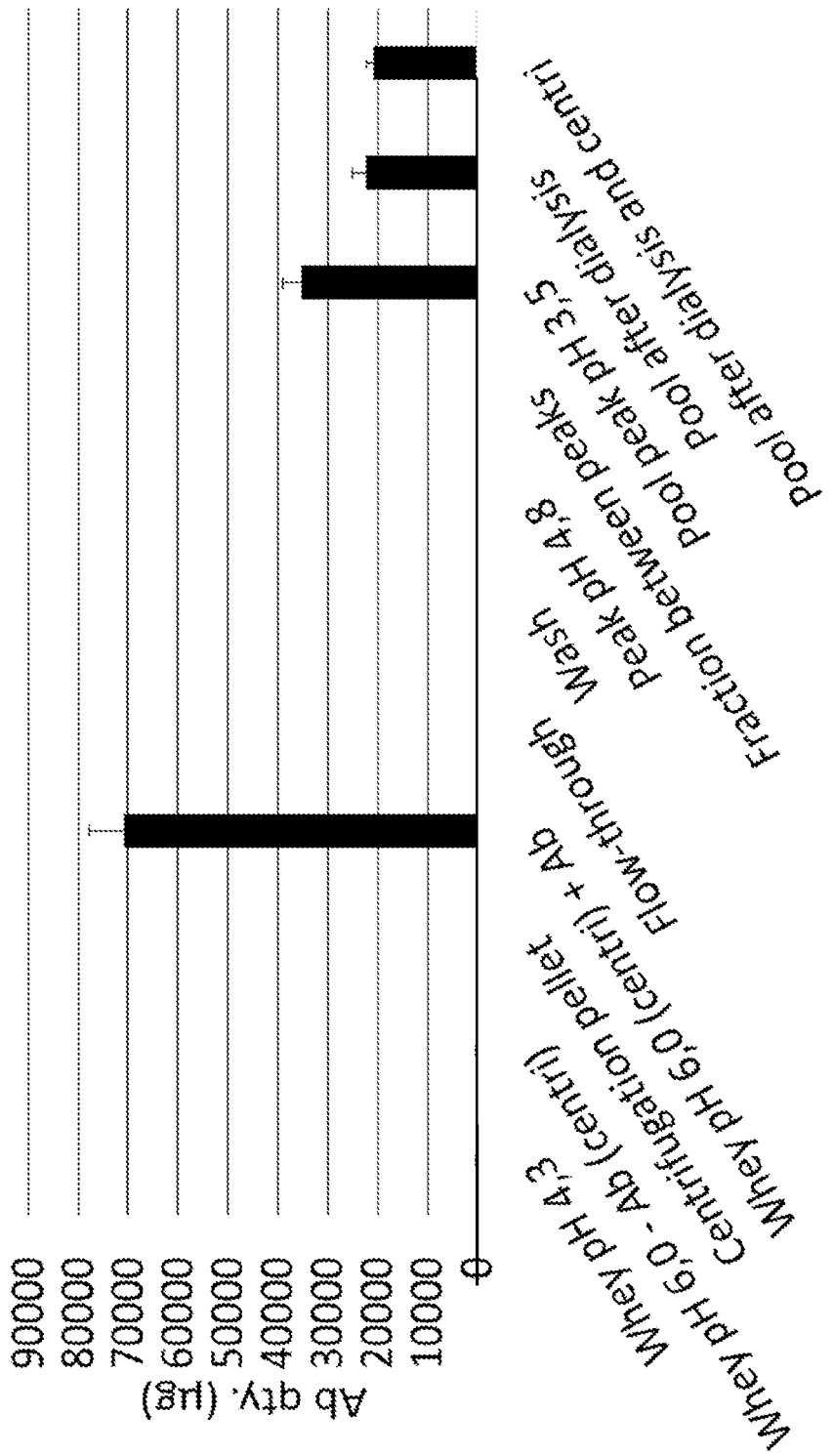

The effect of the process on goat IgG and heterologous antibody recovery is provided in FIG. 11.

From 17 ml of whey containing 2 mg canine monoclonal antibody, >87% of the monoclonal antibody was recovered with a purity of more than >84%. The residual goat antibody in the final product was estimated at less than 30 ug. The residual goat protein in the final product was estimated at less than 1 µg/mg. Yields for antibodies recovery are shown in Table 7.

TABLE 7

Antibodies recovery for purification fractions.

| Sample | Heterologous antibody recovery (%) | Goat antibody recovery (%) |
| --- | --- | --- |
| Loading sample | 100 | 100 |
| Flow through | <5 | >95 |
| wash | <1 | |
| First elution (pH 4.8) | <1 | <3 |
| Second elution (pH 3.5) | >87 | <1 |
| Third elution (pH 3.0) | <1 | <1 |

3 steps gradient (pH 6.0, pH 4.8 and pH 3.0)

The above example was repeated but run was performed as follows at a flow rate of 6 ml/min: 1 column volumes (CV) of the sample (constituted of whey adjusted at pH 6.0 using NaOH) was loaded on cartridge equilibrated in 50 mM sodium acetate, 50 mM NaCl at pH 6.0. Cartridge was washed with 10 CV with equilibration buffer. A first elution was performed using 5 CV of 50 mM sodium acetate, 50 mM NaCl at pH 4.8. The second elution was performed using 5 CV of 50 mM sodium acetate, 50 mM NaCl at pH 3.0. Heterologous antibody were collected by fraction corresponding to 1 CV and neutralized in 1M Tris-HCl at pH 9.0 to a pH stabilizing antibody. Fractions having the heterologous antibody were pooled. Heterologous antibody were dialyzed again 50 mM acetate, 50 mM NaCl at pH 6 through 30 kDa membrane. Analytical assays were identical to those in above example.

Goat antibodies are predominantly eluted at pH 4.8. The heterologous antibody is eluted at pH 3.0. The comparison of this results obtained with the results of the above example shows that the suppression of the elution at pH 3.5 does not have a significant impact on the yield and purity of the heterologous antibody. Elution at pH 3 will be preferred over elution at pH 3.5 in order to recover a maximum of heterologous antibody.

Wash using 500 mM NaCl and 3 steps gradient (pH 6.0, pH 4.7 and pH 3.0)

Example 1.2. was repeated for the sample preparation. Purification of heterologous antibody was carried out by affinity chromatography using 5 ml cartridge containing protein-A (praesto, purolite). Run was performed as followed: 1 column volume (CV) of the sample was loaded on cartridge equilibrated in 50 mM sodium acetate, 50 mM NaCl at pH 6.0 at a flow rate of 1 ml/min. Cartridge was washed with 10 CV with equilibration buffer at a flow rate of 4 ml/min. Then cartridge was washed with 5 CV with 50 mM sodium acetate, 500 mM NaCl at pH 6.0 at a flow rate of 4 ml/min.

A first elution was performed using 5 CV of 50 mM sodium acetate, 100 mM NaCl at pH 4.7 at a flow rate of 4 ml/min. The second elution was performed using 5 CV of 100 mM glycine at pH 3.0 at a flow rate of 4 ml/min. Heterologous antibody were collected by 2 ml fraction and neutralized using 200 µl of 1.5 M of Tris-HCl at pH 8.5 to a pH stabilizing antibody. Fractions having the heterologous antibody were pooled.

Monoclonal heterologous antibody concentration was measured by biolayer interferometry (BLI). Proteins were visualized by SDS-PAGE. The residual goat antibody in the final product was measured by ELISA. Recovery yield (%) was calculated using the following equation:

$$\frac{Cf \times Vf}{Ci \times Vi} \times 100$$

Figure 12:
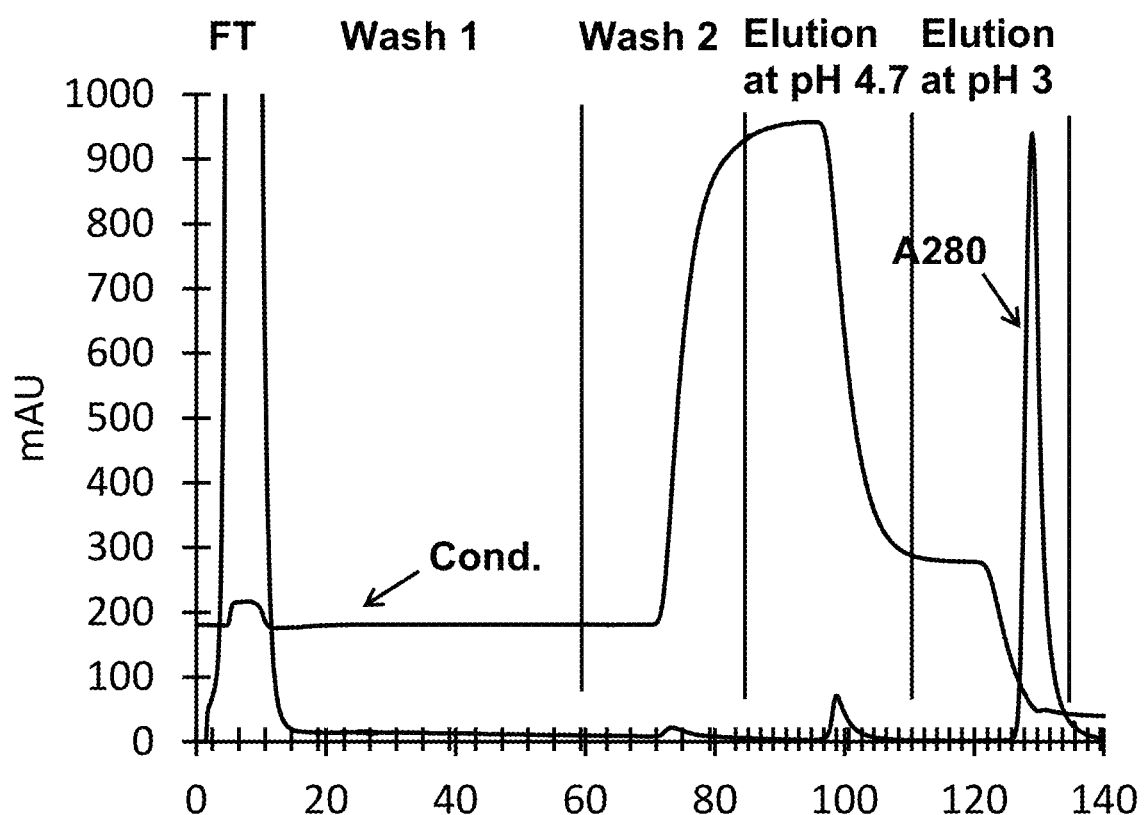
FIG. 12: Chromatogram of the purification by affinity chromatography. The absorbance at 280 nm at the outlet of the column and the conductivity are represented respectively by the lines as indicated. The fractions and fraction numbers are marked. The sample of goat whey was loaded onto the column and then the column was washed with the equilibration buffer at pH 6 then with the equilibration buffer containing 500 mM NaCl. Proteins which were not bound to the column were recovered in the flow through (FT) and washes fractions. Steps gradient at pH 4.7 and 3 was applied in order to elute goat antibodies and heterologous antibody respectively.
Figure 13:
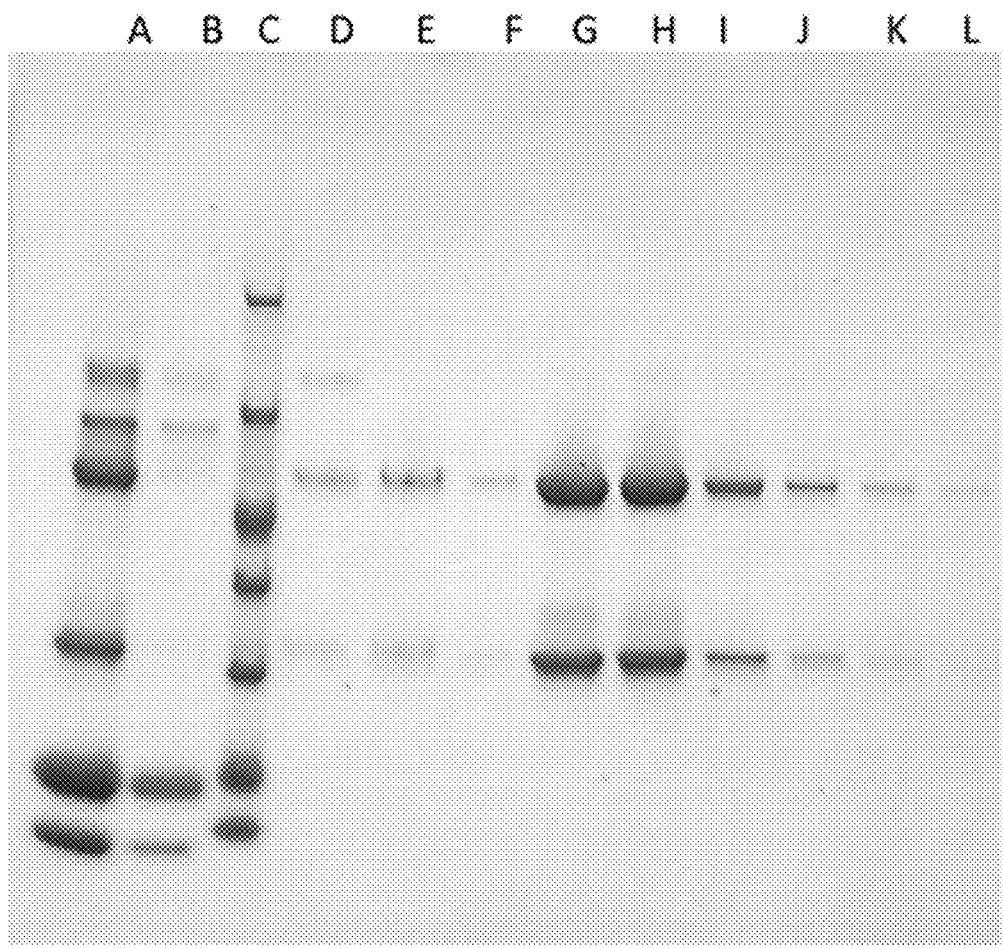
FIG. 13: SDS-PAGE analysis for purification fractions. well A. 2 µL of loading sample. goat whey contains mainly α-lactalbumin (MW≈18 kDa) and β-lactoglobulin (MW≈14 Kda), goat antibodies and heterologous antibody. Well B. 2 µL of the flow through (FT) containing mainly α-lactalbumin and β-lactoglobulin well C. 10 µL of Pierce Unstained Protein Molecular Weight Marker (Thermo Scientific, Rockford, USA). Well D. 10 µL of fraction n°19 containing goat antibodies, well E 10 µL of pooled fractions n°19 to 32 containing goat antibodies, well E 5 µL of fraction n°43 containing purified heterologous antibody, well F 5 µL of fraction n°44 containing purified heterologous antibody, well G 5 µL of fraction n°45 containing purified heterologous antibody, well H 5 µL of fraction n°46 containing purified heterologous antibody, well I 5 µL of fraction n°47 containing purified heterologous antibody, well J 5 µL of fraction n°48 containing purified heterologous antibody, well K 5 µL of fraction n°49 containing purified heterologous antibody, well L 5 µL of fraction n°50 containing purified heterologous antibody.

(with Cf=concentration of the molecule of interest in the final product (g/l), Vf=volume of the final product (l), Ci=concentration of the molecule of interest in the initial product which correspond to loading sample (g/l), Vi=volume of the initial product which correspond to loading sample (l)). Chromatogram of the purification is shown in FIG. 12 and the corresponding SDS-PAGE analysis is shown in FIG. 13.

In our experimental conditions, more than 83% of goat antibodies loaded were harvested in the flow through and washes. Washing using 500 mM NaCl makes it possible to release goat antibodies (fraction n°19). Around 15% of goat antibodies loaded were harvested in the first elution at pH 4.7. Conversely, heterologous antibody having high affinity for protein-A resin was weakly lost in the flow through, washes and first elution (less than 1%). The monoclonal antibody was harvested in the second elution at pH 3.

Comparison of 3 and 2 steps gradient (pH 4.7 and pH 3.0)

Example 1.2. was repeated for the sample preparation from 1.3 liter of milk containing 0.1 g/l heterologous antibody. Purification of heterologous antibody was carried out by affinity chromatography using 5 ml cartridge containing protein-A (praesto, purolite). Two different chromatography were performed: (A) loading sample and equilibration buffer at pH 6 and (B) loading sample and equilibration buffer at pH 4.7. Run was performed as follows: 10 column volumes (CV) of the sample were loaded on cartridge equilibrated in (A) 50 mM sodium acetate, 500 mM NaCl at pH 6.0 or (B) 50 mM sodium acetate, 500 mM NaCl at pH 4.7 (B) at a flow rate of 5 ml/min. Cartridge was washed with 10 CV with equilibration buffer at a flow rate of 5 ml/min. A first elution was performed for condition (A) only using 5 CV of 50 mM sodium acetate, 500 mM NaCl at pH 4.7 at a flow rate of 5 ml/min. The second elution was performed in both conditions using 5 CV of 100 mM glycine at pH 3.0 at a flow rate of 5 ml/min. Heterologous antibody were collected by 2.5 ml fractions and neutralized using 250 μl of 1.5 M of Tris-HCl at pH 8.5 to a pH stabilizing antibody. Fractions having the heterologous antibody were pooled.

Monoclonal heterologous antibody concentration was measured by ELISA. Proteins were visualized by SDS-PAGE. The residual goat antibody in the final product was measured by ELISA. Recovery yield (%) was calculated using the following equation:

$$\frac{Cf \times Vf}{Ci \times Vi} \times 100$$

Figure 14:
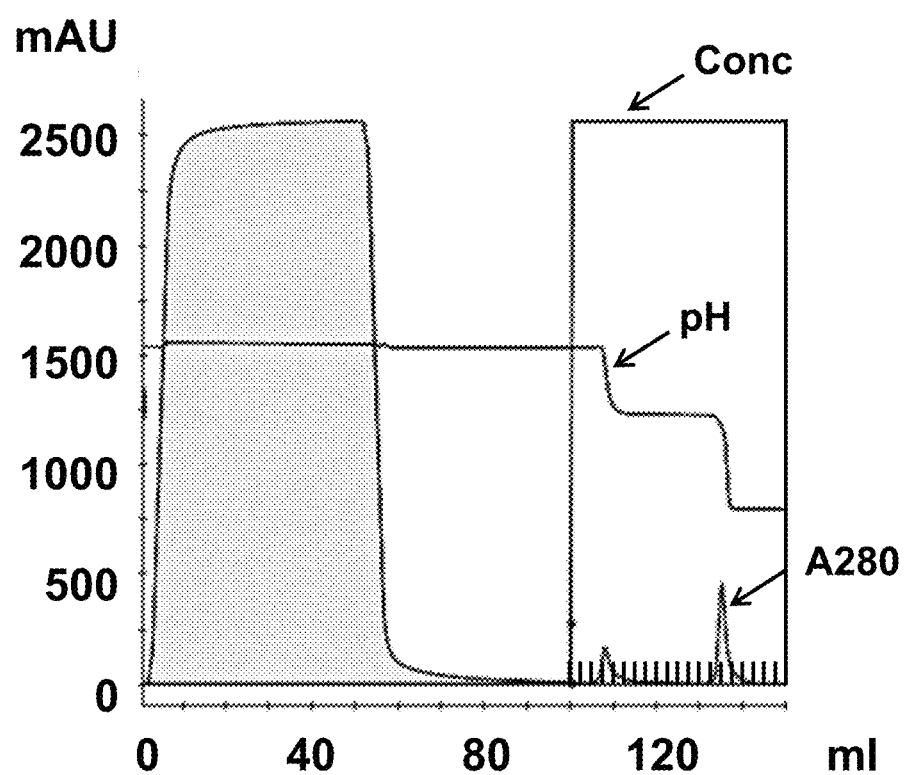
FIG. 14: Chromatogram of the purification by affinity chromatography. The absorbance at 280 nm at the outlet of the column and the conductivity are represented respectively by the lines as indicated. The elution buffers application also indicated. The fractions and fraction numbers are marked. The sample of goat whey was loaded onto the column and then the column was washed with the equilibration buffer at pH 6 then with the equilibration buffer containing 500 mM NaCl. Proteins which were not bound to the column are recovered in the flow through (FT) and washes fractions. Steps gradient at pH 4.7 and 3 was applied in order to elute goat antibodies and heterologous antibody respectively.
Figure 15A:
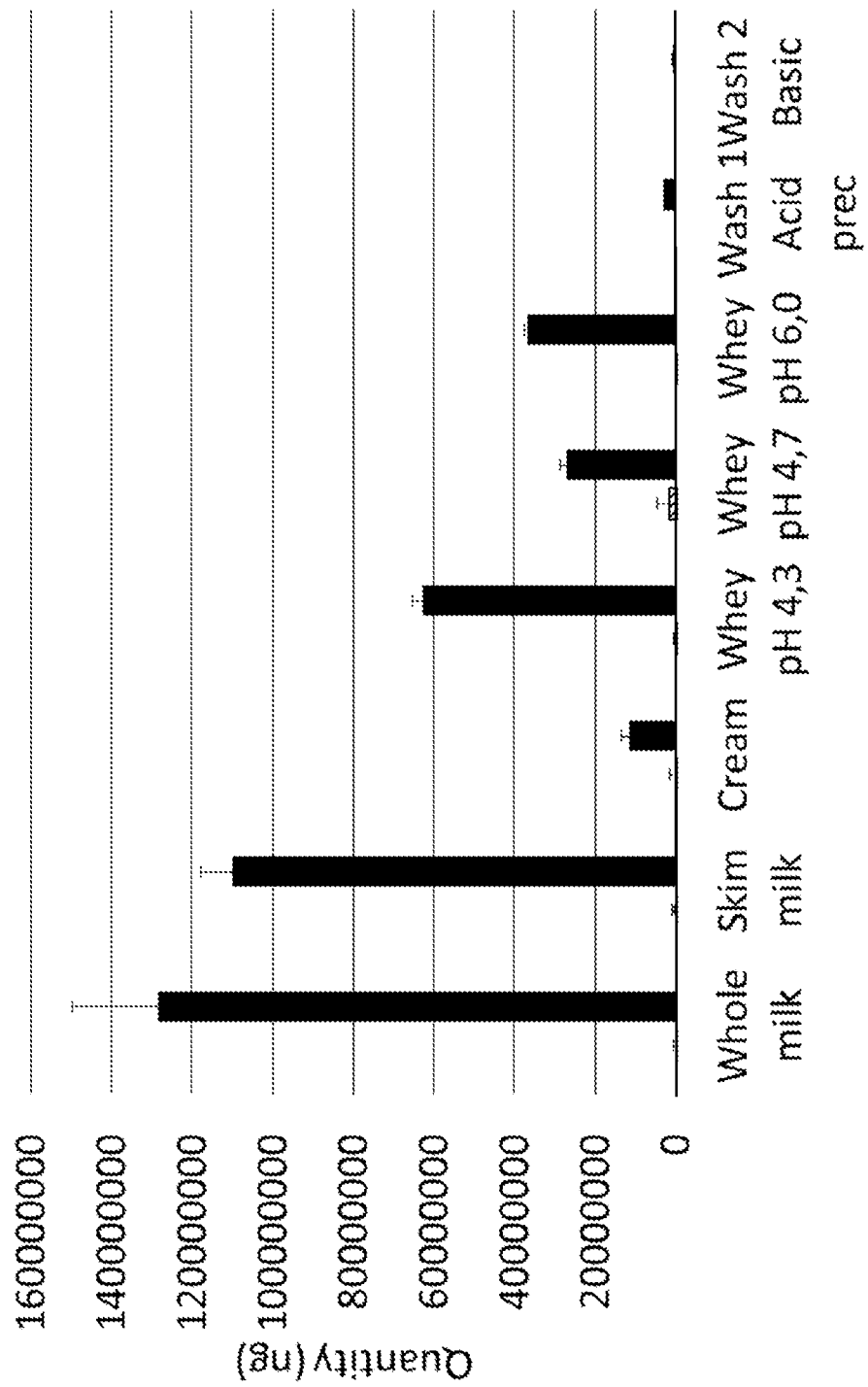
Figure 15B:
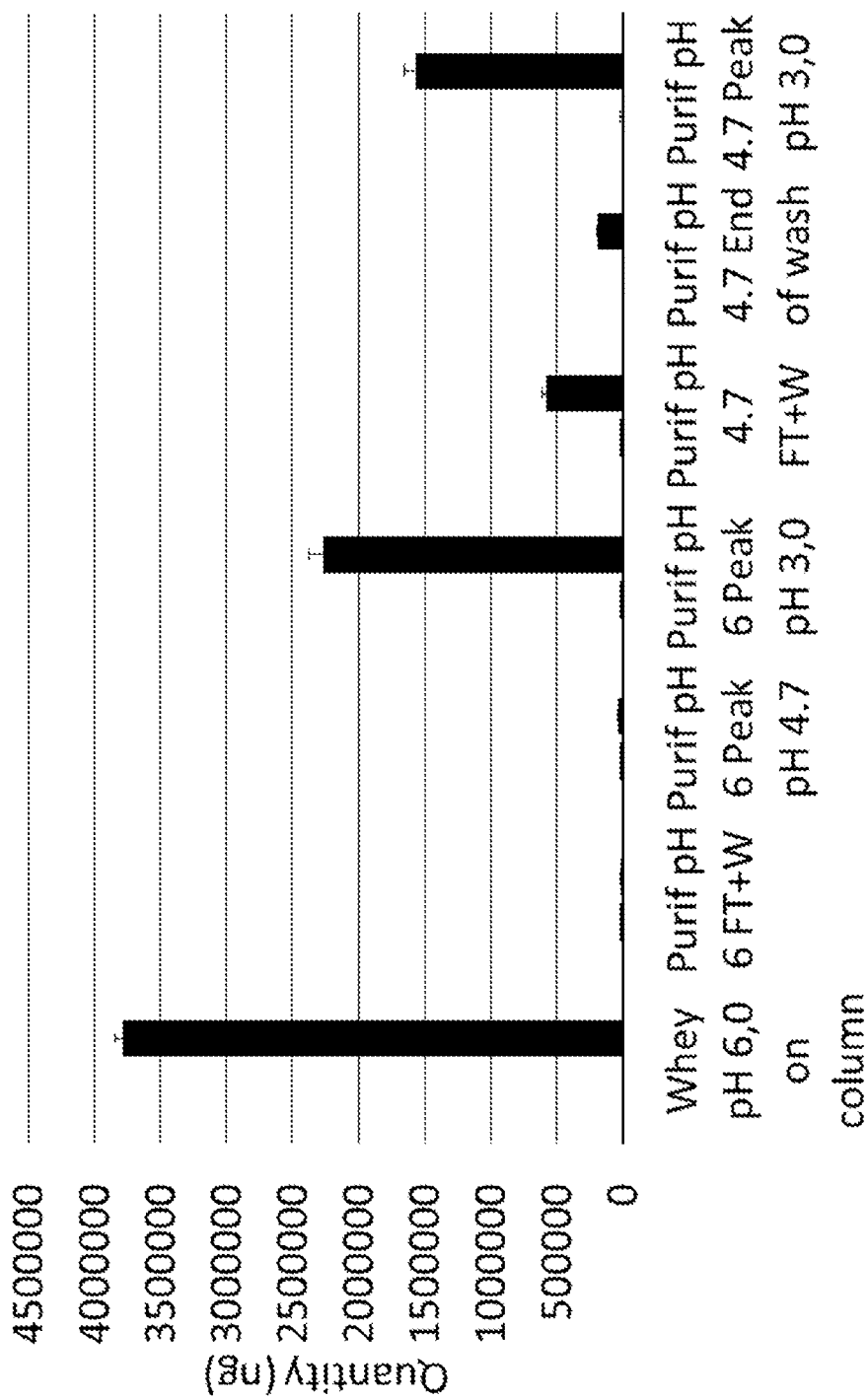
Figure 16A:
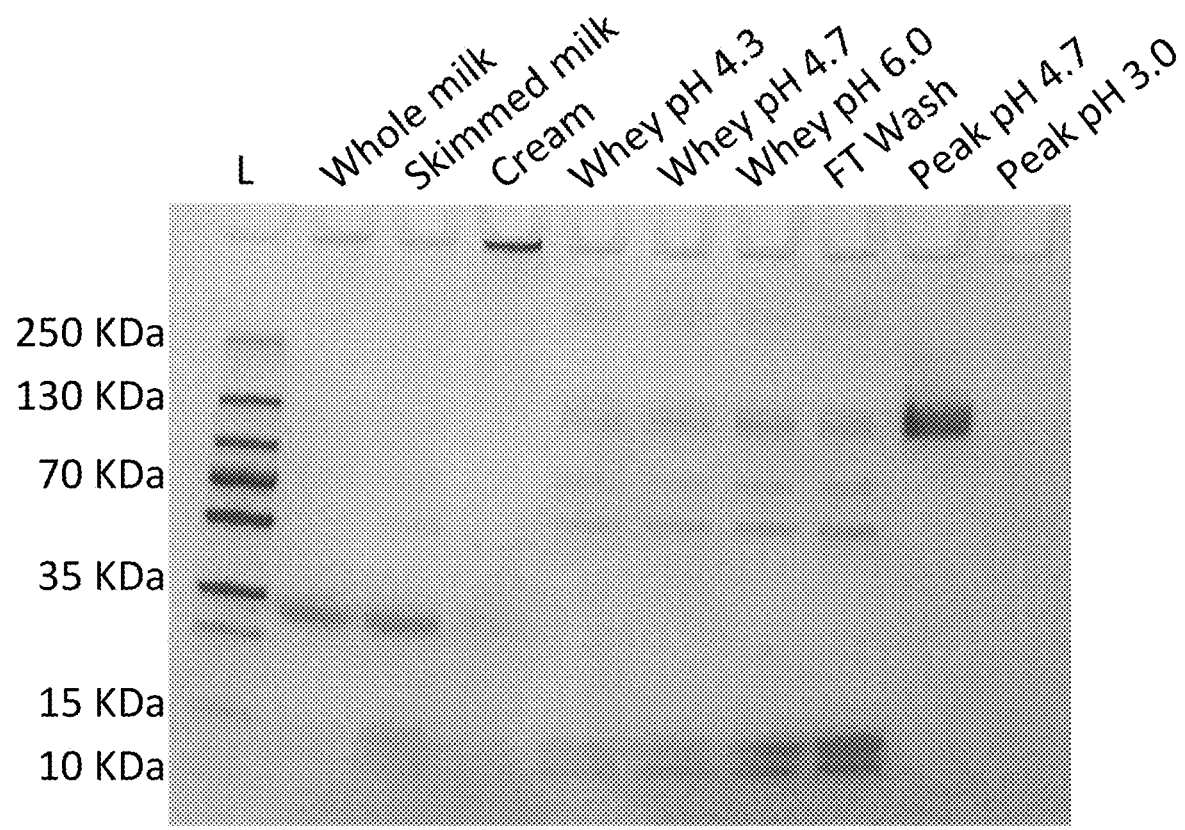
FIGS. 16A-16C: SDS-PAGE/WB results of the process samples. Native SDS-PAGE and Western Blot anti-heterologous antibody (FIGS. 16B and 16C) results are shown for process samples obtained from control (FIG. 16A) and milk with antibody (FIGS. 16B and 16C). Five (5) µg of proteins were loaded in each well.
Figure 16B:
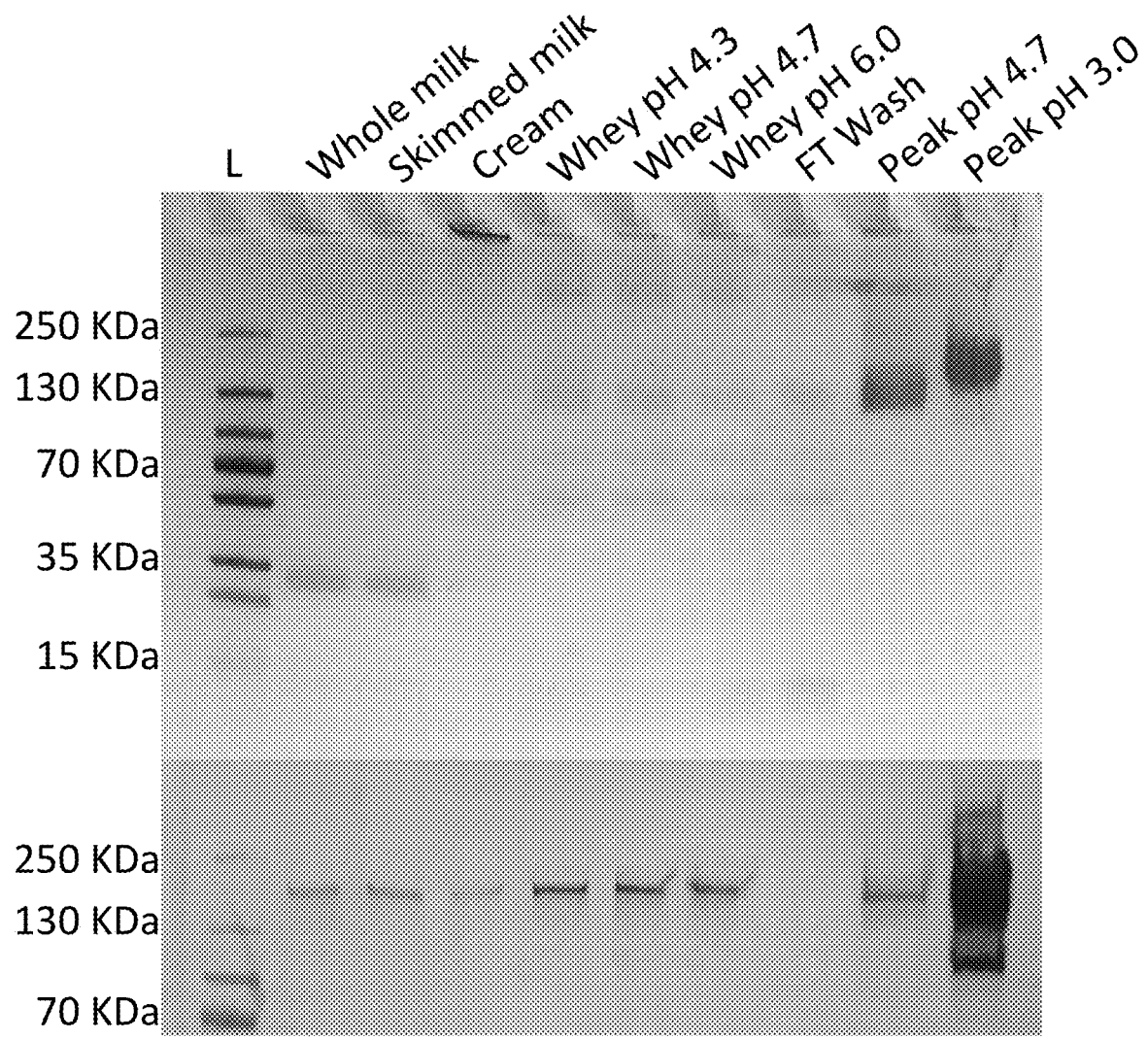
Figure 16C:
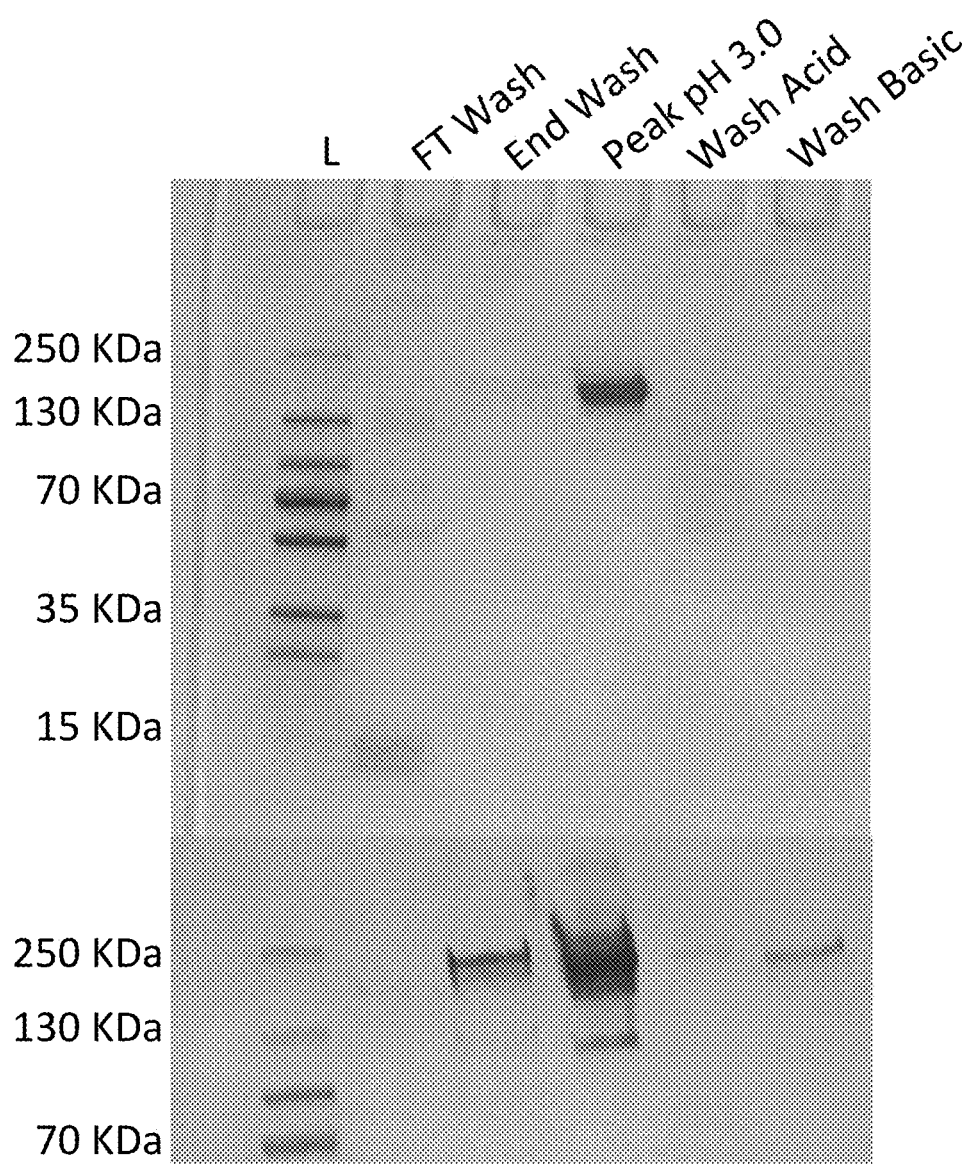

(with Cf=concentration of the molecule of interest in the final product (g/l), Vf=volume of the final product (l), Ci=concentration of the molecule of interest in the initial product which correspond to loading sample (g/l), Vi=volume of the initial product which correspond to loading sample (l)). Chromatogram of the purification is shown in FIG. 14, ELISA results are shown in FIG. 15 and the corresponding SDS-PAGE/WB analysis is shown in FIG. 16.

Figure 17:
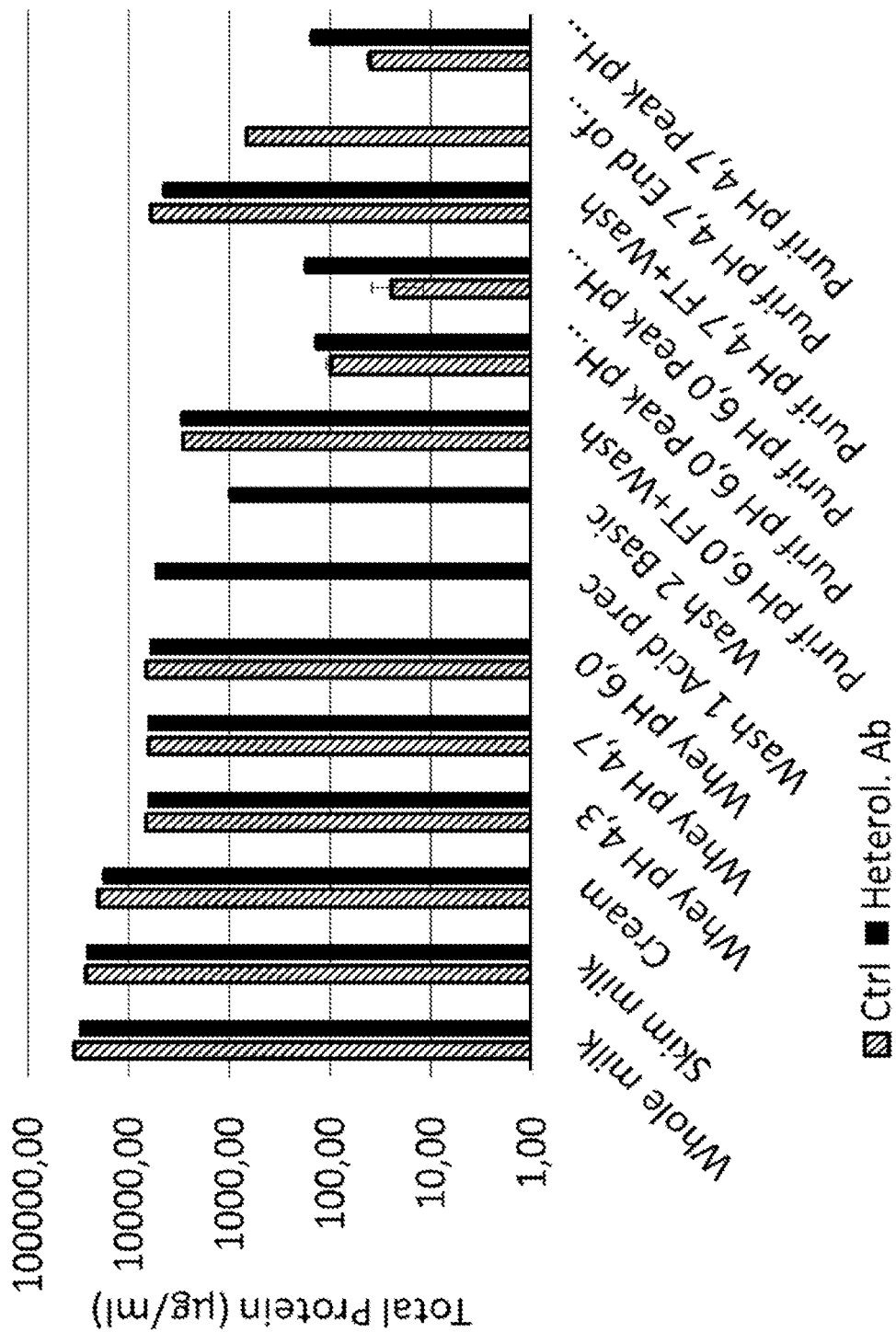
FIG. 17: Total protein content results of the process samples. A BCA assay was realized on all processed samples obtained from both control (left bar) and milk with antibody (right bar) samples. Samples corresponding to process are whole milk, skim milk, whey at pH 4.3, whey adjusted at pH 4.7 and pH 6.0 and corresponding purifications fractions—flowthrough and washes, peak pH 4.7 (or end of washes for purification at pH 4.7) and the peak at pH 3.0. Pellets washes after both acid precipitation and pH adjustment before purification were also tested.
Figure 18A:
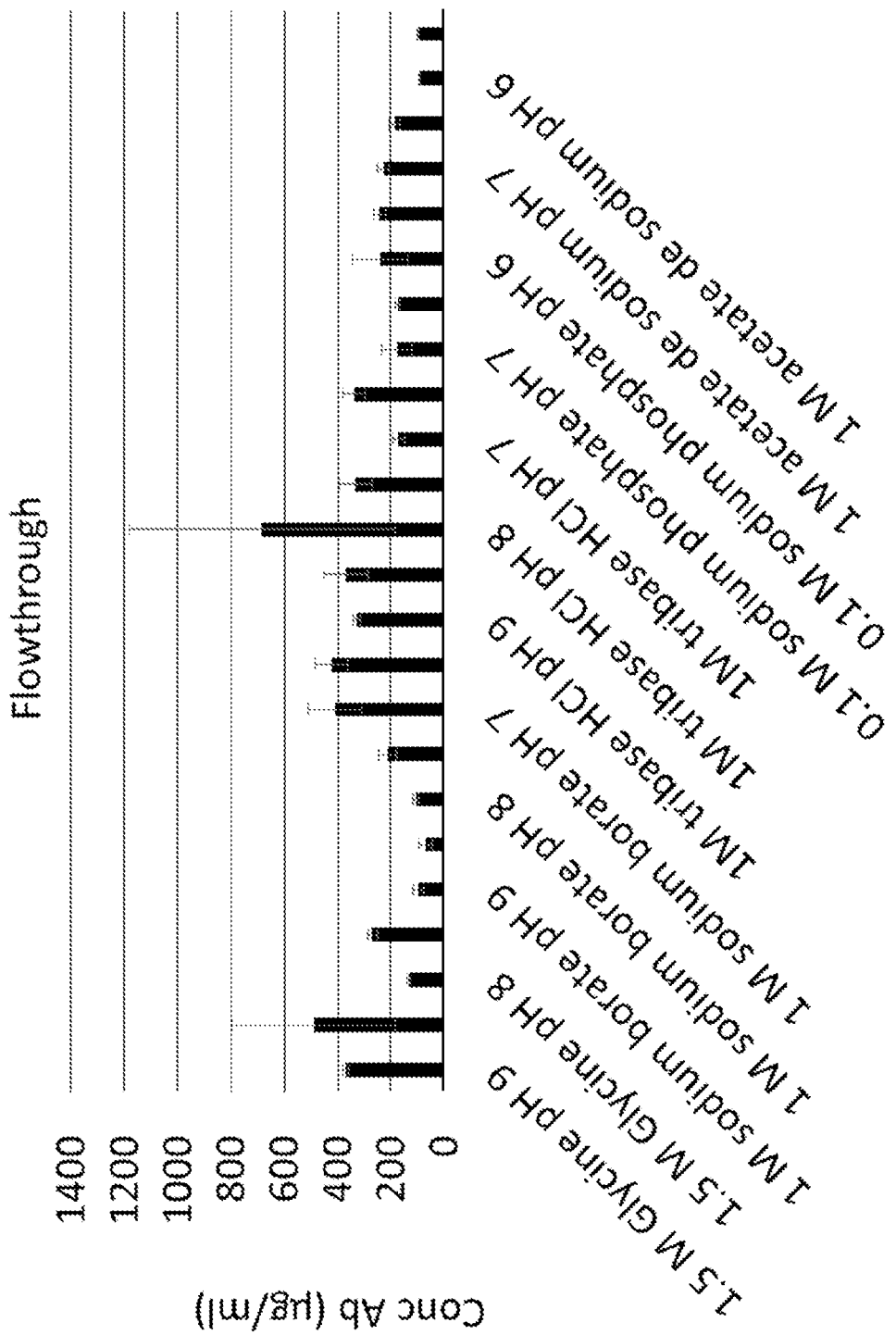
FIGS. 18A-18D: ELISA results—Purification optimization. Different equilibration buffers were tested to determine the optimum buffer. Heterologous antibody concentrations retrieved in flowthrough (FIG. 18A) and the 3 elutions (pH 4.8 (FIG. 18B), 3.5 (FIG. 18C), and 3.0 (FIG. 18D)) are presented in the graphs.
Figure 18B:
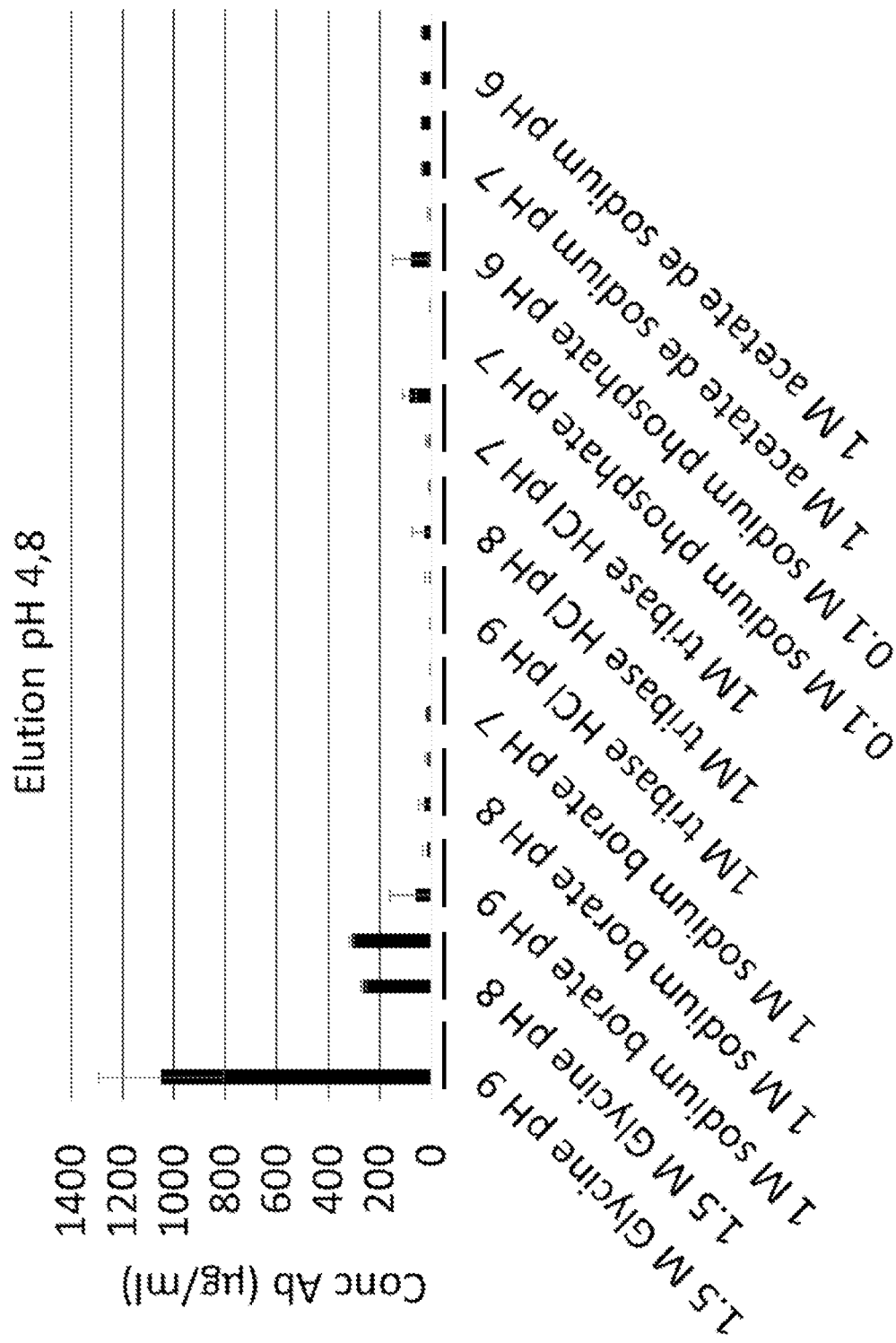
Figure 18C:
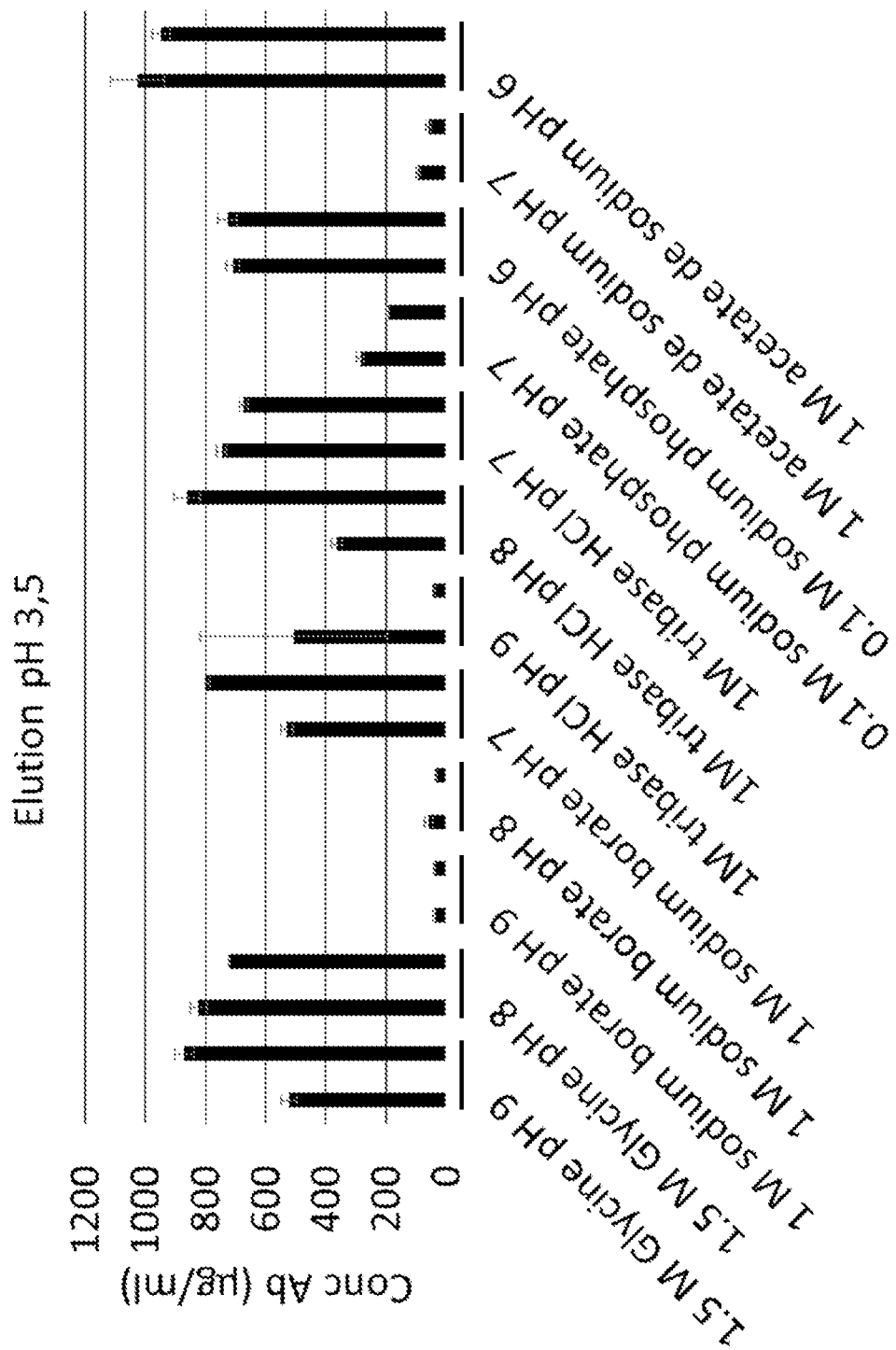
Figure 18D:
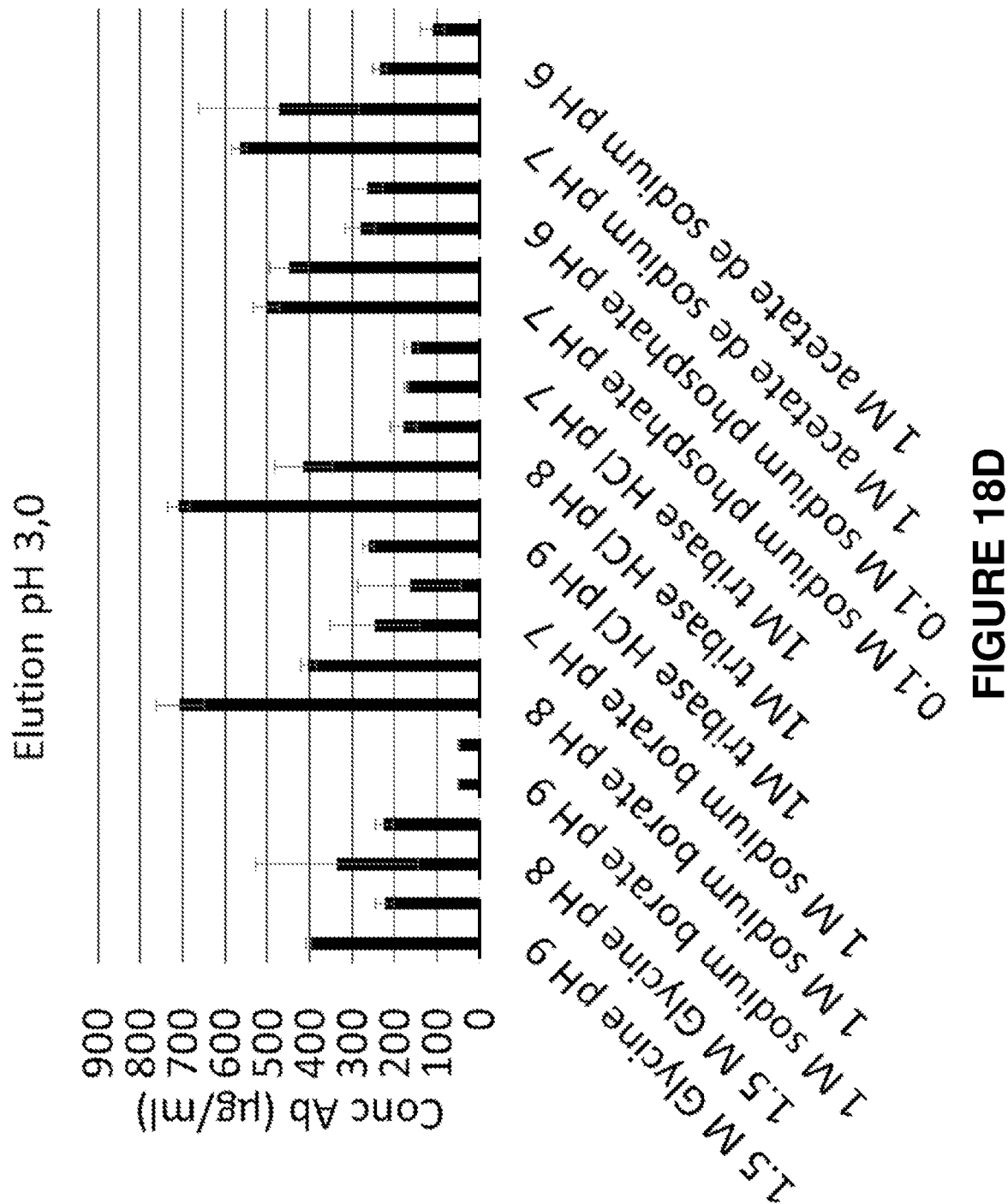

The effect of the process on the total protein content is shown in FIG. 17.

In our experimental conditions, less than 1% of goat antibodies loaded were harvested in the elution at pH 3.0. Conversely, heterologous antibody having high affinity for protein-A resin was weakly lost in the flow through, washes and first elution. The monoclonal antibody was harvested in the elution at pH 3. We observed that loading the sample at pH 4.7 induced a decrease of heterologous antibody recovery upon elution compared to loading the sample at pH 6.0, probably because of a better affinity at this pH. Purities of heterologous antibody harvested after loading at either pH 4.7 or pH 6.0 were similar.

b) Equilibration buffer 1.5 M Glycine at pH 8 and 9

Purification of heterologous antibody was carried out by batch mode (see Example 4.1.d). Protein-A resin is washed two times with 2 resin volumes of equilibration buffer (1.5 M glycine at pH 8 and 9). Buffer was removed by centrifugation at 500 g for 2 min. 2 bed volumes of sample diluted 2 times in equilibration buffer was mixed for 60 min with the matrix. The flow through was removed by centrifugation at 500 g for 2 min. The resin was washed two times by incubation of 4 bed volumes using equilibration buffer with resin for min followed by centrifugation at 500 g for 2 min. Retained proteins were successively eluted with 50 mM sodium acetate at pH 4.8, 3.5 and finally 3.0.

Monoclonal heterologous antibody concentration was measured by enzyme-linked immunosorbent assay (ELISA). Purity was estimated by capillarity electrophoresis (CE) and calculated using the following equation:

$$\frac{Ca}{Ct} \times 100$$

(with Ca=antibody concentration in the sample (g/l) and Ct=total protein concentration in the sample (g/l)). The residual goat antibody in the final product was measured by ELISA. Recovery yield (%) was calculated using the following equation:

$$\frac{Cf \times Vf}{Ci \times Vi} \times 100$$

(with Cf=concentration of the molecule of interest in the final product (g/l), Vf=volume of the final product (l), Ci=concentration of the molecule of interest in the initial product which correspond to loading sample (g/l), Vi=volume of the initial product which correspond to loading sample (l)).

From 200 μl of whey containing 400 μg canine monoclonal antibody, up to 74% of the monoclonal antibody was recovered (FIG. 18) with a purity up to 87%. The residual goat antibody in the final product was estimated between 0.1 and 10 μg.

1M Sodium Borate at pH 7, 8 and 9

The above example was repeated, but equilibration and elution buffers were replaced by 1 M sodium borate at pH 7, 8 or 9. The analytical assays were carried out as in above Example.

From 200 μl of whey containing 400 μg canine monoclonal antibody, up to 46% of the monoclonal antibody was recovered (FIG. 18) with a purity up to 88%. The residual goat antibody in the final product was estimated at less than 1 μg.

0.1 M Sodium Phosphate at pH 6 and 7

The above example was repeated, but equilibration and elution buffers were replaced by 0.1 M sodium phosphate at pH 6 or 7. The analytical assays were carried out as in above Example.

From 200 μl of whey containing 400 μg canine monoclonal antibody, >85% of the monoclonal antibody was recovered (FIG. 18) with a purity of more than >80%. The residual goat antibody in the final product was estimated at less than 13 rig.

1M Tris Base at pH 7, 8 and 9

The above example was repeated, but equilibration and elution buffers were replaced by 1M Tris Base at pH 7, 8 or 9. The analytical assays were carried out as in above Example.

From 200 μl of whey containing 400 μg canine monoclonal antibody, up to 86% of the monoclonal antibody was recovered (FIG. 18) with a purity of more than >90%. The residual goat antibody in the final product was estimated at less than 20 rig.

1M Sodium Acetate at pH 6 and 7

The above example was repeated, but equilibration and elution buffers were replaced by 1M Sodium acetate at pH 6 or 7. The analytical assays were carried out as in above Example. The residual goat protein concentration in the final product (HCP for host cell protein) is quantified by ELISA.

From 200 μl of whey containing 400 μg canine monoclonal antibody, >90% of the monoclonal antibody was recovered (FIG. 18) with a purity of more than >89%. The residual goat antibody in the final product was estimated at less than 1.5 rig. The residual goat protein in the final product was estimated at less than 1 ng/µg.

10 to 100 mM Sodium Acetate at pH 6

The above example was repeated, but equilibration and elution buffers were replaced by 10, 20, 50 and 100 mM Sodium acetate at pH 6. Sample was diluted 9:1 (v:v) in equilibration buffer before loading. The analytical assays were carried out as in above Example.

From 200 µl of whey containing 400 µg canine monoclonal antibody, >90% of the monoclonal antibody was recovered (FIG. 18) with a purity of more than >92%. The residual goat antibody in the final product was estimated at less than 1.5 µg. The residual goat protein in the final product was estimated at less than 1 ng/µg.

The best equilibration buffer condition that was selected for next assays was sodium acetate 50 mM at pH 6 because it displayed both the better purity and yields.

c) Elution Buffer

Purification of heterologous antibody was carried out by batch mode (see Example 4.1.d). Protein-A resin was washed two times with 2 resin volumes of equilibration buffer (0.1 M acetate at pH 6). Buffer was removed by centrifugation at 500 g for 2 min. 2 bed volumes of sample diluted 2 times in equilibration buffer were mixed for 60 min with the matrix. The flow through was removed by centrifugation at 500 g for 2 min. The resin was washed two times by incubation of 4 bed volumes using equilibration buffer (0.1 M acetate, 1M glycine or 0.1 M citrate at pH 4.7-4.8-4.9 and 5.0) with resin for in followed by centrifugation at 500 g for 2 min. Retained proteins were successively eluted with the same buffers at both pH 3.5 and 3.0. The analytical assays were carried out as in above Example.

Figure 19A:
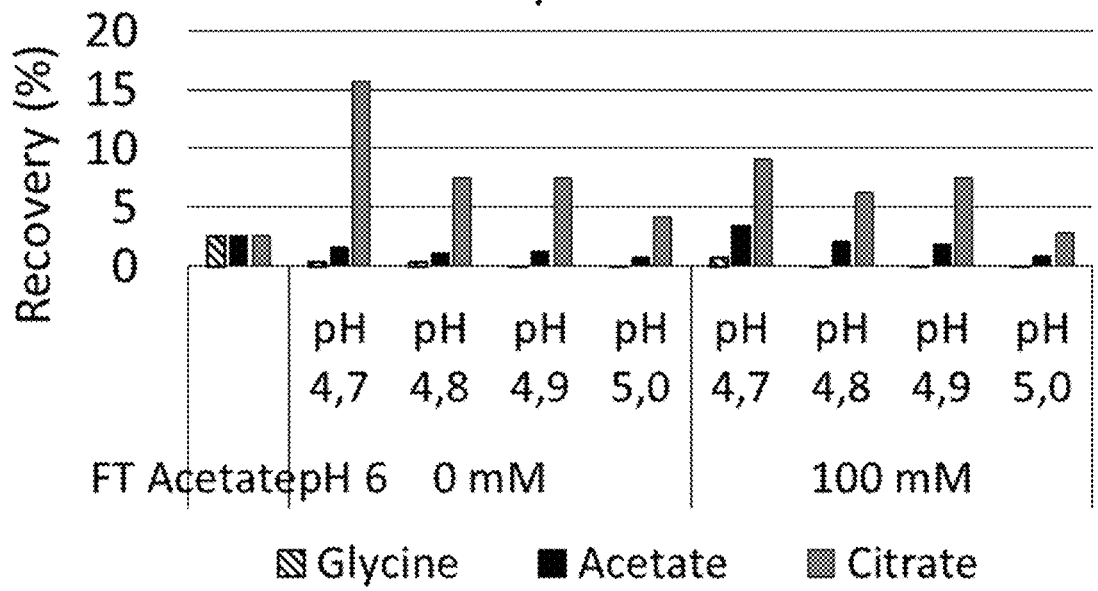
Figure 19B:
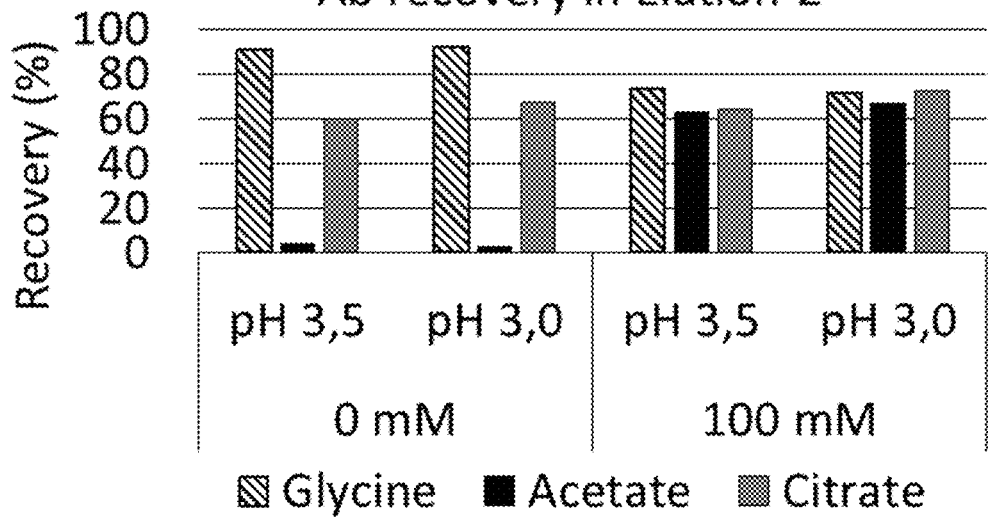
Figure 19C:
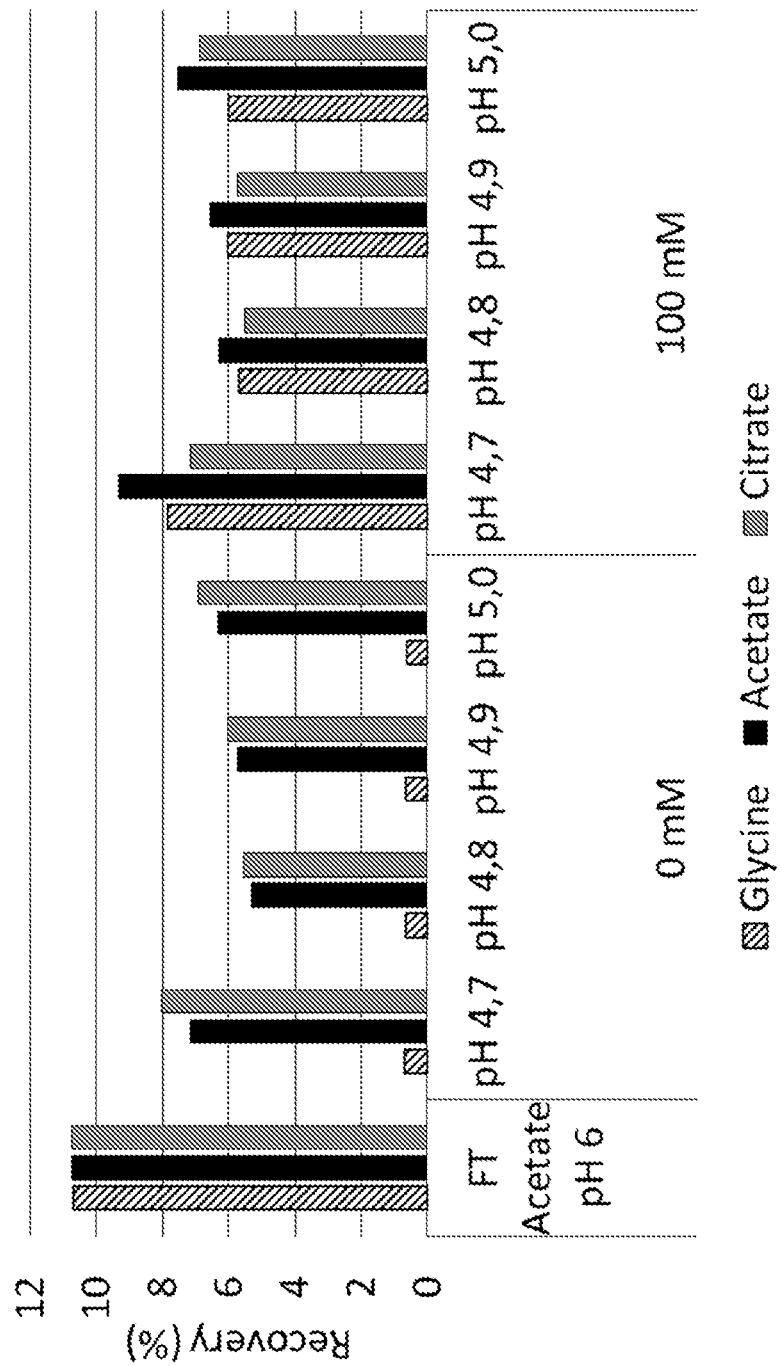

From 200 µl of whey containing 400 µg canine monoclonal antibody, up to 90% of the monoclonal antibody was recovered in the best condition: glycine buffer 100 mM NaCl for elution 1 at pH 4.7 (condition that provides the better goat IgG elimination both with good heterologous antibody retention) and glycine buffer at pH 3.0 for elution 2 (for the same reasons); see FIG. 19. The residual goat antibody in the final product was estimated <1000 ppm. To perform the first elution at pH 4.7 enabled to eliminate more goat IgG than at pH >4.7.

Example 5: Milk

1. Frozen Milk

Examples 1.1 and 1.2 were repeated, but whole goat milk was frozen at −20° C. for 1 month then treated. The results were identical to those in examples 1.

2. Refrigerated Milk

Examples 1.1 and 1.2 were repeated, but whole goat milk was stored at 4° C. for 2 days then treated. The results were identical to those in examples 1.

3. Sheep Milk Containing Heterologous Antibody

Example 1.2 was repeated for the sample preparation, but whole fresh sheep milk containing the heterologous antibody was treated. The results for the skimming and caseins precipitation were similar to those in Example 1.2

Purification of heterologous antibody was carried out by affinity chromatography using 5 ml cartridge containing protein-A (praesto, purolite). Run was performed as followed: 1 column volume (CV) of the sample was loaded on cartridge equilibrated in 50 mM sodium acetate, 50 mM NaCl at pH 6.0. Cartridge was washed with 10 CV with equilibration buffer. Then cartridge was washed with 5 CV with 50 mM sodium acetate, 500 mM NaCl at pH 6.0.

Figure 20:
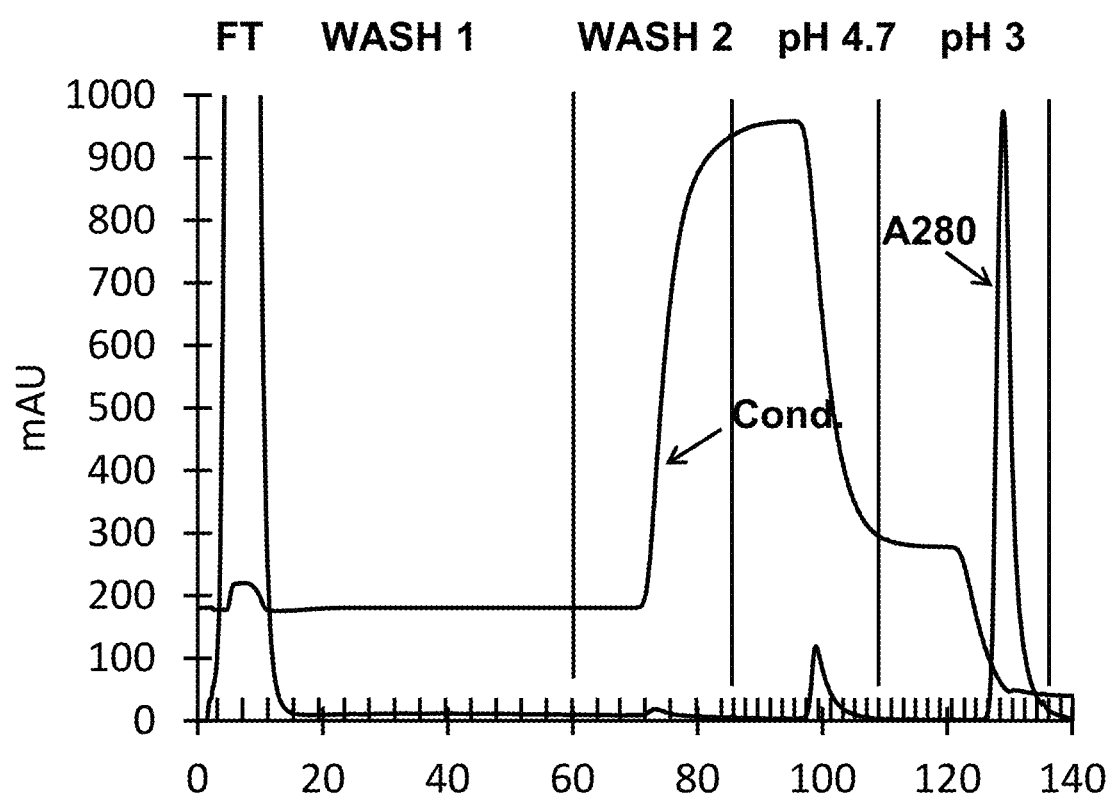
FIG. 20: Chromatogram of the purification by affinity chromatography. The absorbance at 280 nm at the outlet of the column and the conductivity are represented respectively by the lines as indicated. The sample of sheep whey is loaded onto the column and then the column is washed with the equilibration buffer at pH 6 then with the equilibration buffer containing 500 mM NaCl. Proteins which are not bind to the column are recovered in the flow through (FT) and washes fraction. Step gradient at pH 4.7 and 3 are applied.

A first elution was performed using 5 CV of 50 mM sodium acetate, 100 mM NaCl at pH 4.7. The second elution was performed using 5 CV of 100 mM glycine at pH 3.0. Heterologous antibody were collected by 2 ml fraction and neutralized using 200 µL of 1.5 M of Tris-HCl at pH 8.5 to a pH stabilizing antibody. Fractions having the heterologous antibody were pooled. Chromatogram of the purification is shown in FIG. 20.

Figure 21:
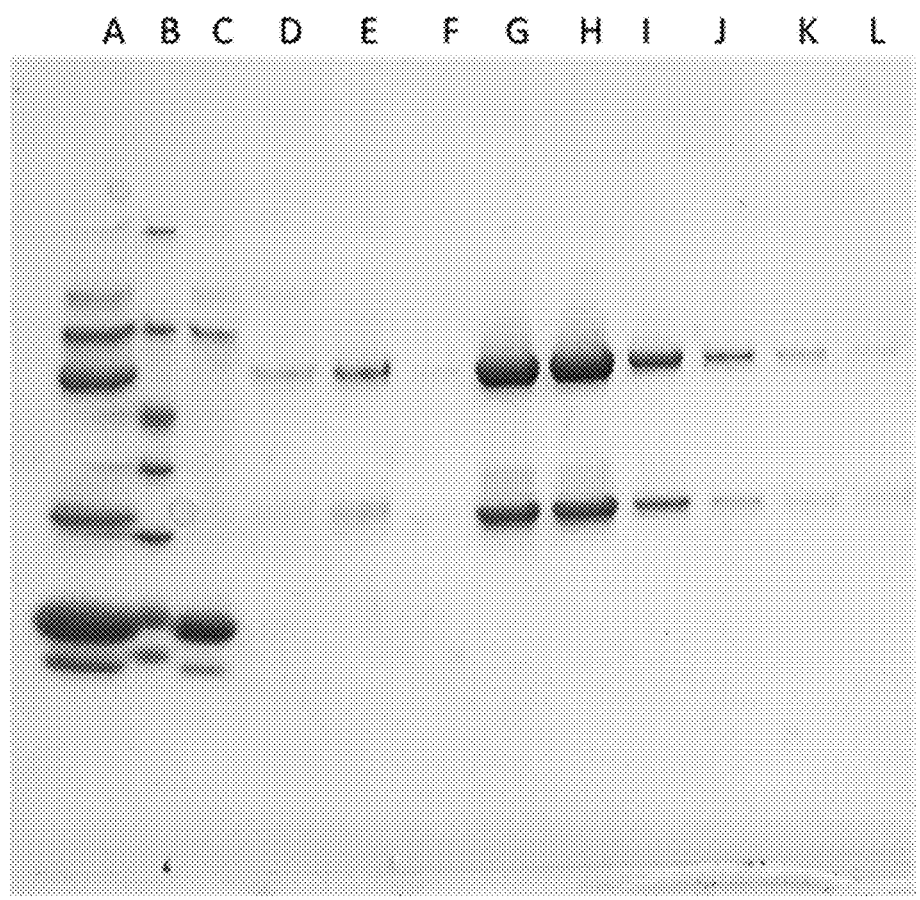
FIG. 21: SDS-PAGE analysis for purification fractions. well A. 2 µL of loading sample. Sheep whey contains mainly α-lactalbumin (MW≈18 kDa) and β-lactoglobulin (MW≈14 Kda), sheep antibodies and heterologous antibody. well B. 10 µL of Pierce Unstained Protein Molecular Weight Marker (Thermo Scientific, Rockford, USA). Well C. 2 µL of the flow through containing mainly α-lactalbumin and β-lactoglobulin well D. 10 µL of fraction n°19 containing sheep antibodies, well E 10 µL of pooled fractions no 19 to 32 containing sheep antibodies, well E 5 µL of fraction n°43 containing purified heterologous antibody, well F 5 µL of fraction n°44 containing purified heterologous antibody, well G 5 µL of fraction n°45 containing purified heterologous antibody, well H 5 L of fraction n°46 containing purified heterologous antibody, well I 5 µL of fraction n°47 containing purified heterologous antibody, well J 5 µL of fraction n°48 containing purified heterologous antibody, well K 5 µL of fraction n°49 containing purified heterologous antibody, well L 5 µL of fraction n°50 containing purified heterologous antibody.

Monoclonal heterologous antibody concentration was measured by biolayer interferometry (BLI). Proteins are visualized by SDS-PAGE (FIG. 21). The residual sheep antibody in the final product was measured by ELISA. Recovery yield (%) was calculated using the following equation:

$$\frac{Cf \times Vf}{Ci \times Vi} \times 100$$

(with Cf=concentration of the molecule of interest in the final product (g/l), Vf=volume of the final product (l), Ci=concentration of the molecule of interest in the initial product which correspond to loading sample (g/l), Vi=volume of the initial product which correspond to loading sample (l)).

Results for the chromatography were similar to those in example 4.2.ii named "wash using 500 mM NaCl and 3 steps gradient" which was carried out under the same conditions except that it was carried out with goat milk.

4. Heterologous Antibody Concentration

Figure 22:
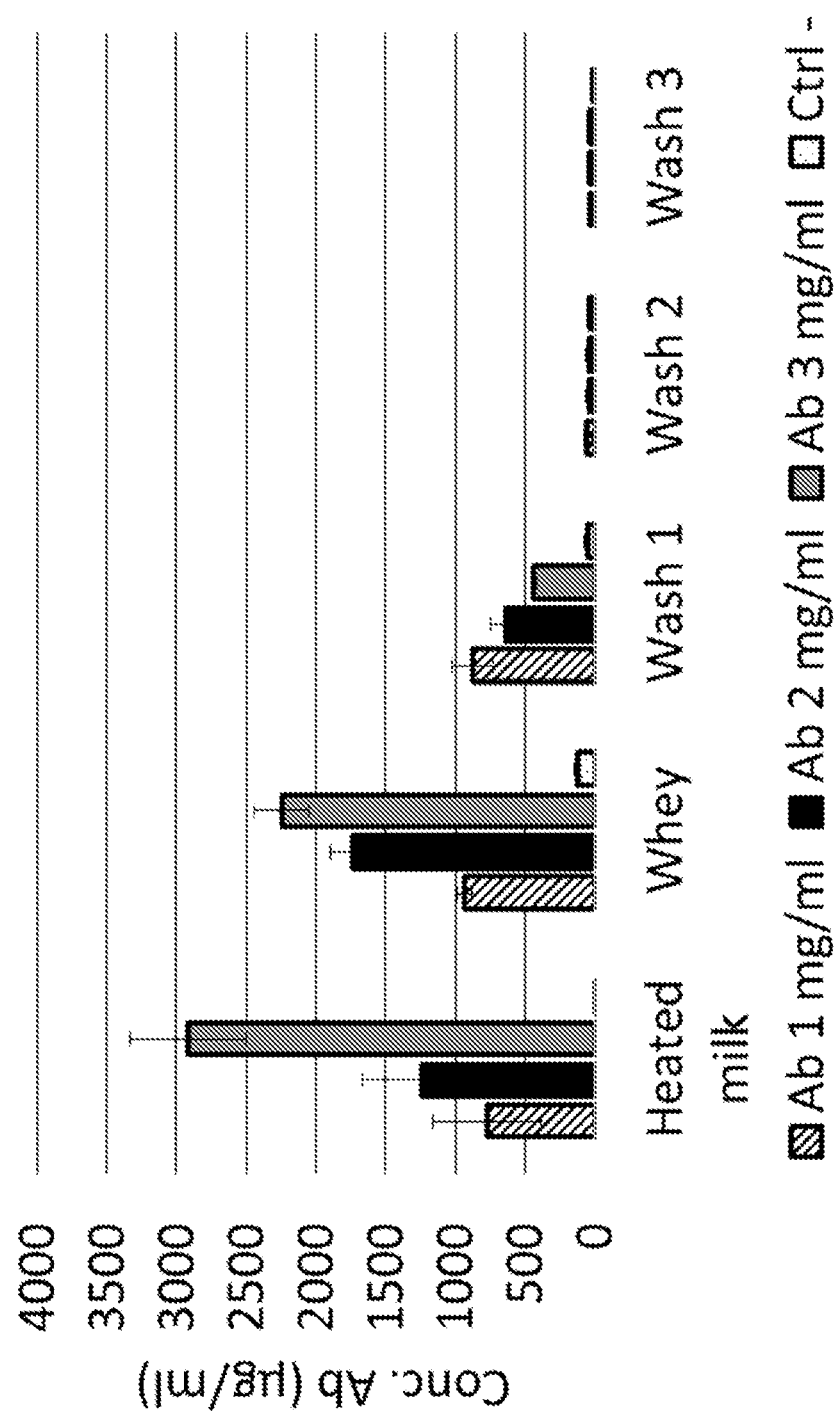
FIG. 22: ELISA results of the process samples. Heterologous antibody concentrations are shown for 4 conditions, i.e starting with milk with heterologous antibody at 0 (control, right bar), 1, 2 or 3 (respectively 1st to 3rd bar) g/l. Pellets obtained were washed with buffer to retrieve residual heterologous antibody.
Figure 23:
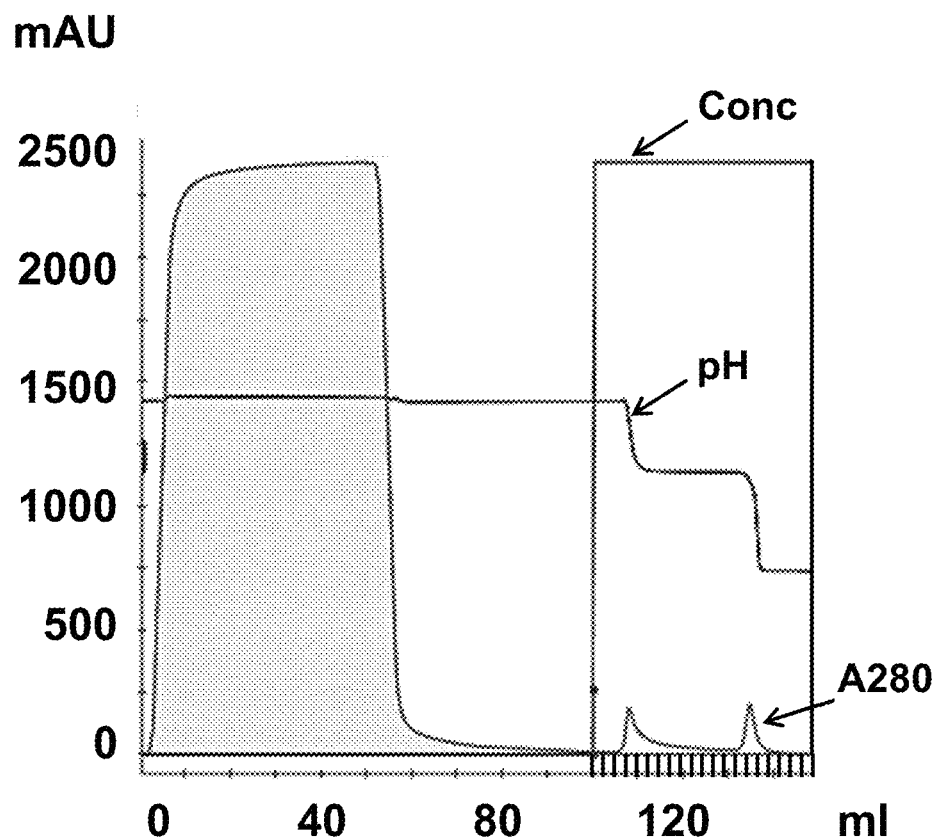
FIG. 23: Chromatogram of the purification by affinity chromatography. The absorbance at 280 nm at the outlet of the column and the conductivity are represented respectively by the lines as indicated. The elution buffers application are also indicated. The fractions and fraction numbers are marked. The sample of goat whey was loaded onto the column and then the column was washed with the equilibration buffer at pH 6 then with the equilibration buffer containing 500 mM NaCl. Proteins which were not bound to the column were recovered in the flow through (FT) and washes fractions. Steps gradient at pH 4.7 and 3 was applied in order to elute goat antibodies and murine antibody, respectively.
Figure 24A:
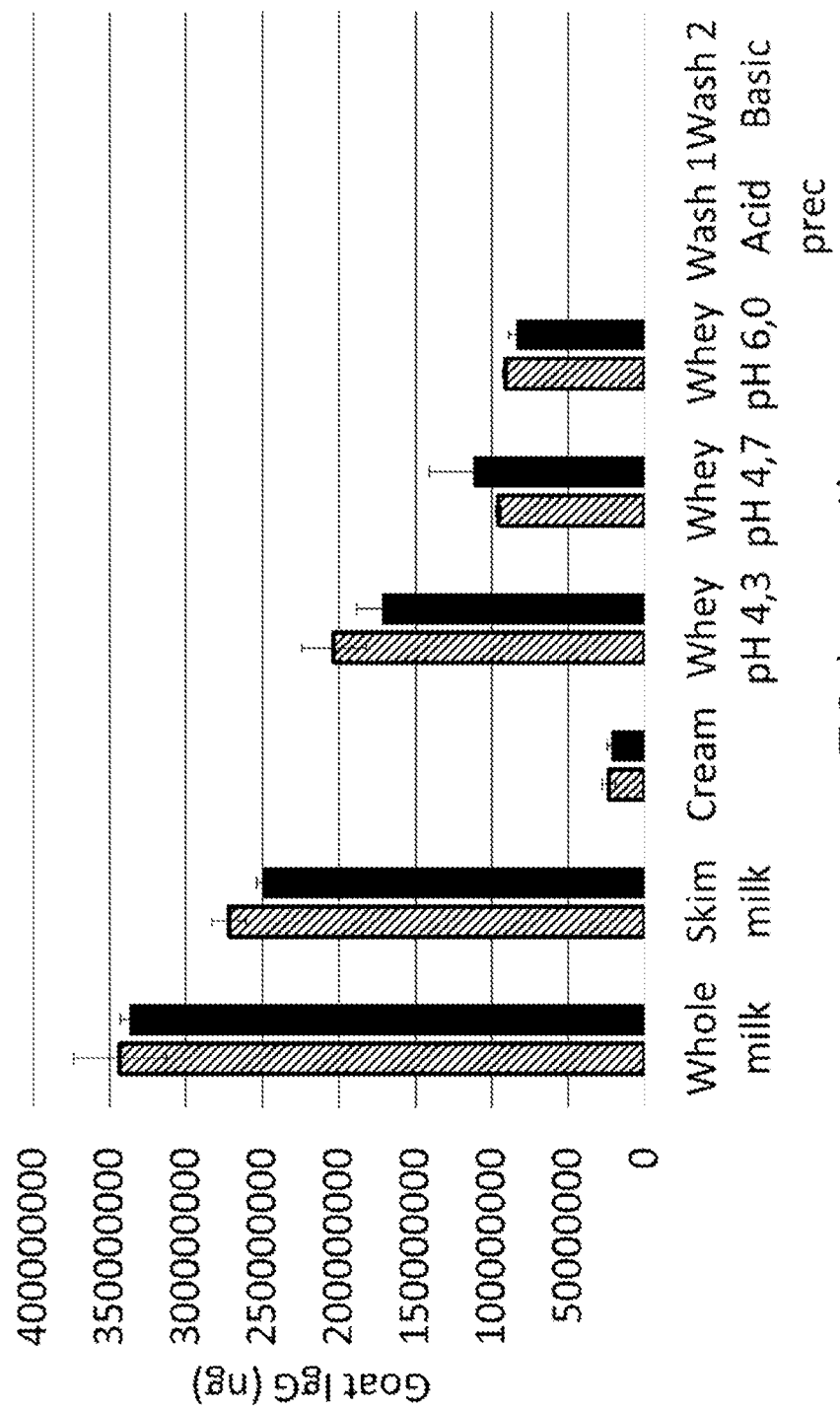
FIGS. 24A-24D: ELISA results of the process samples. Goat IgG (FIGS. 24A and 24B) and Murine antibody (FIGS. 24C and 24D) recoveries are shown in ctrl (left bar) versus (right bar) milk with antibody, i.e with heterologous antibody at 0.1 g/l. Whey at pH 4.3 was separated in two parts, the first was adjusted at pH 4.7 and the second at pH 6.0 to perform both purifications, i.e with sample loading at either pH 4.7 or pH 6.0.
Figure 24B:
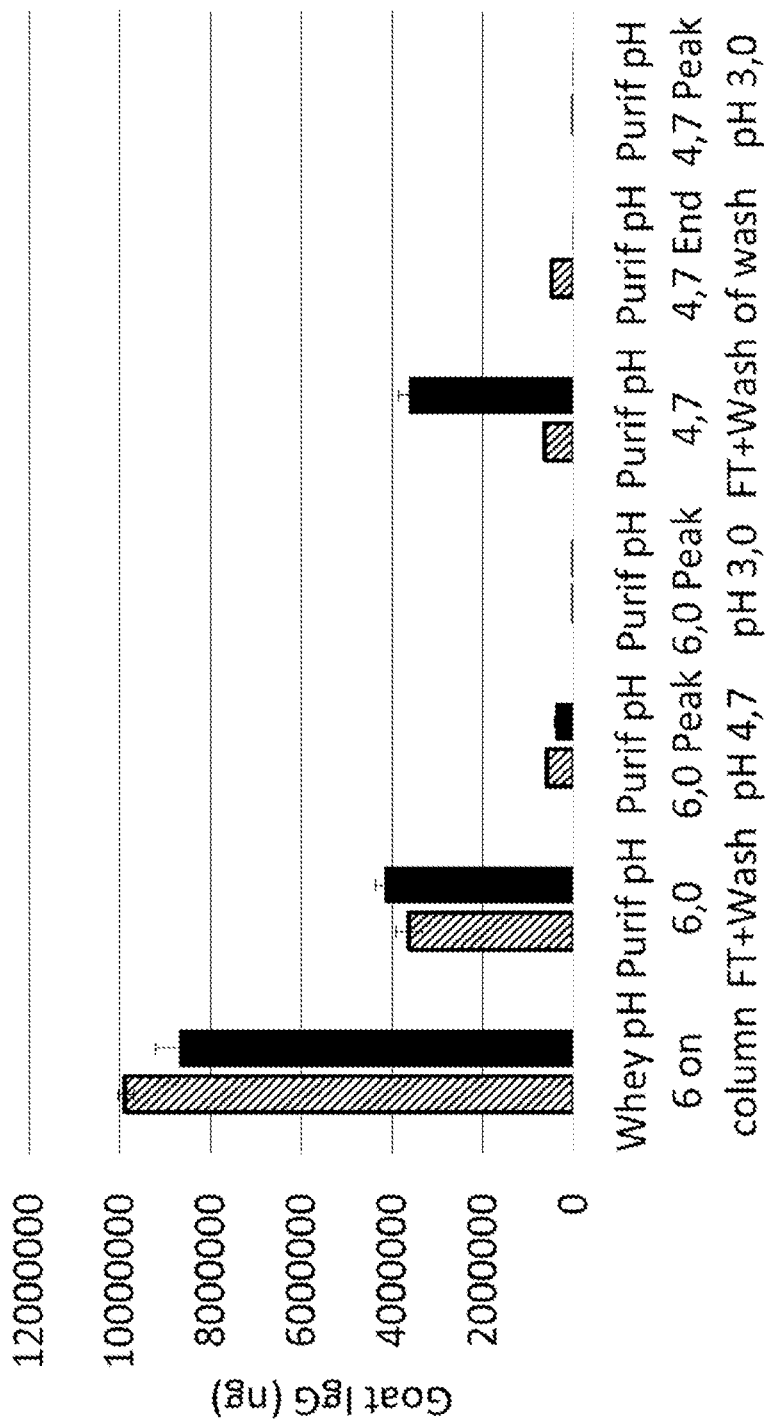
Figure 24C:
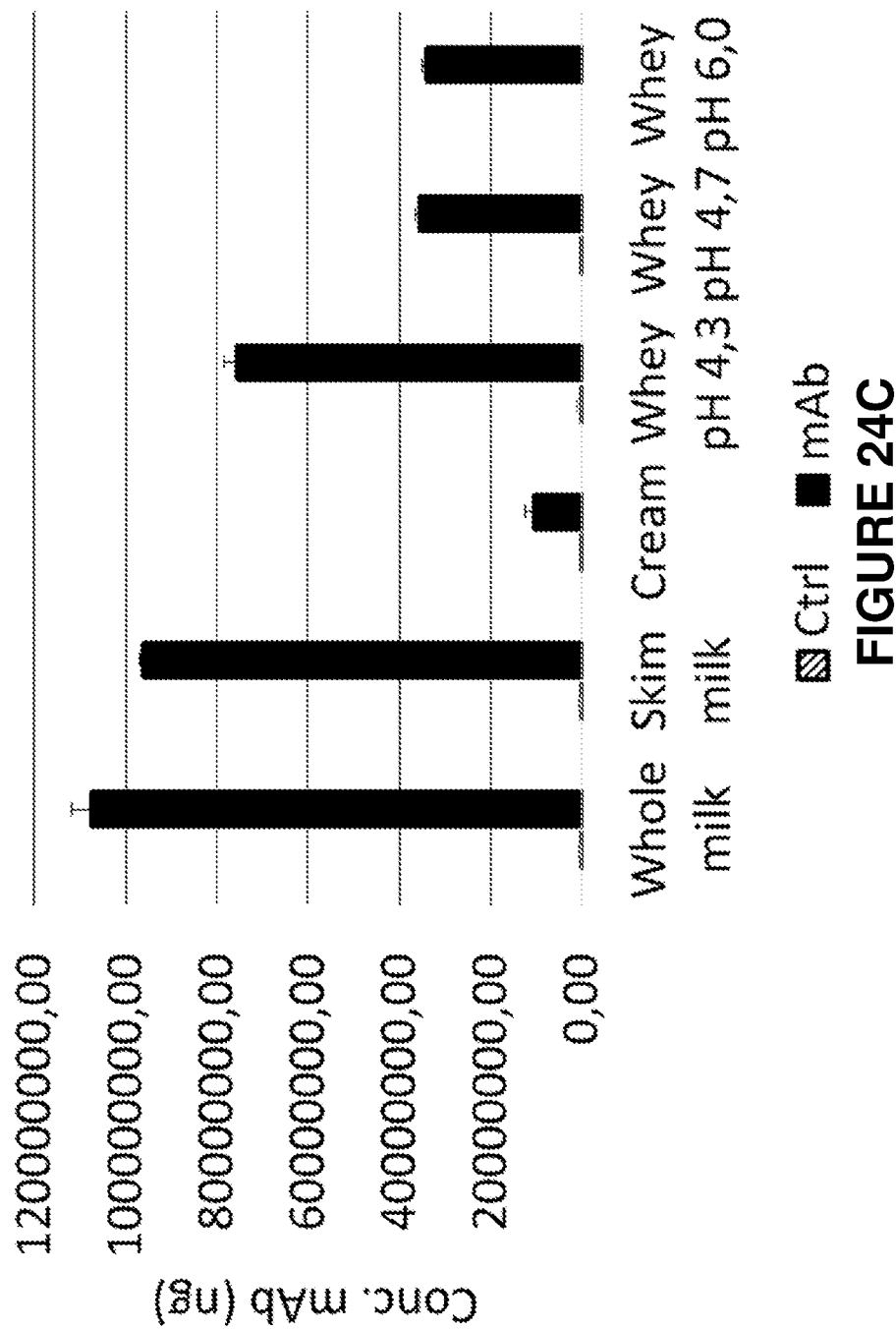
Figure 24D:
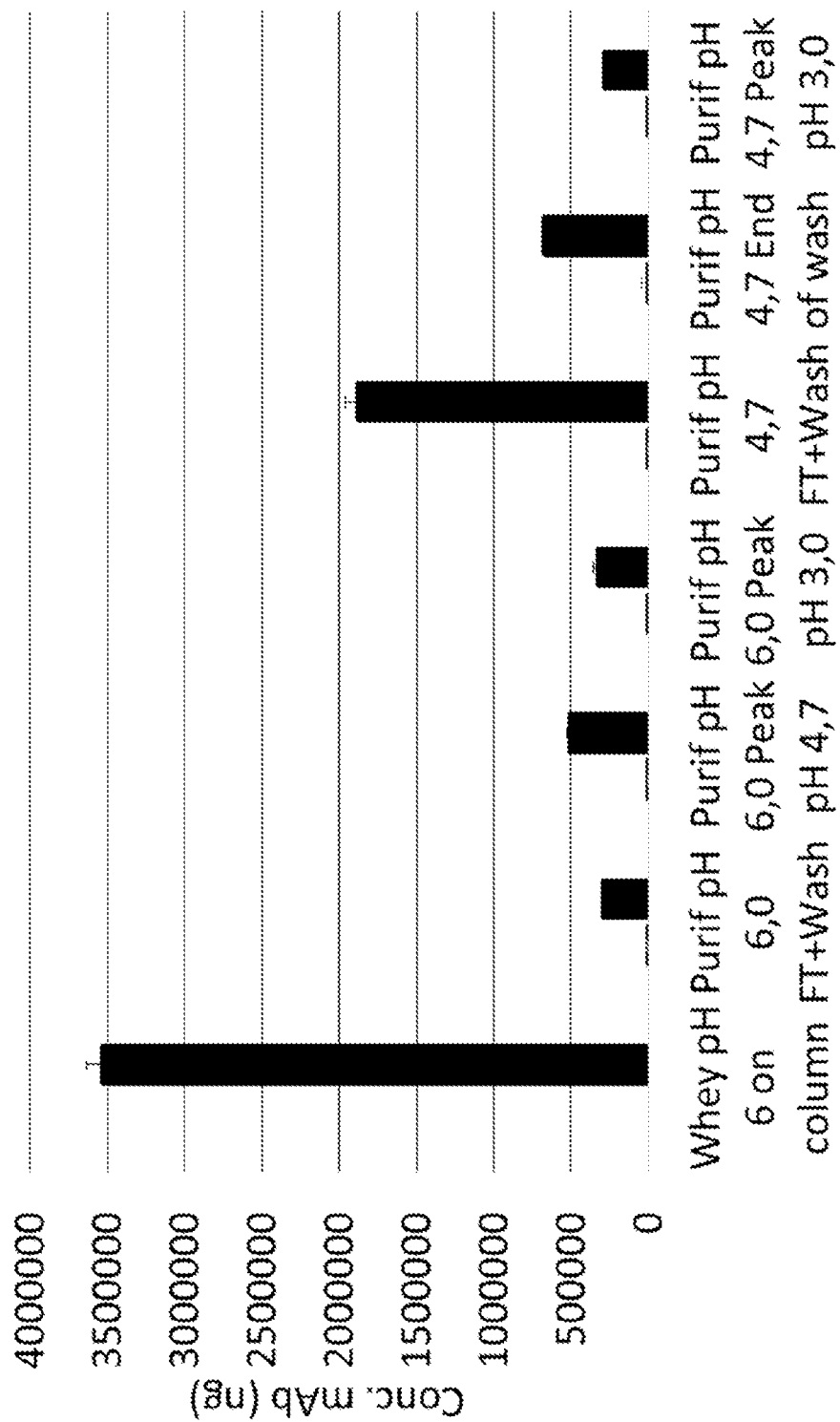
Figure 25:
FIG. 25: Total protein content results of the process samples. A BCA assay was realized on all processed samples obtained from both control (left bar) and (right bar) milk samples with antibody. Samples corresponding to process are whole milk, skim milk, whey at pH 4.3, wheys adjusted at pH 4.7 and pH 6.0 and corresponding purifications fractions—flowthrough and washes, peak pH 4.7 (or end of washes for purification at pH 4.7) and the peak at pH 3.0.
Figure 26:
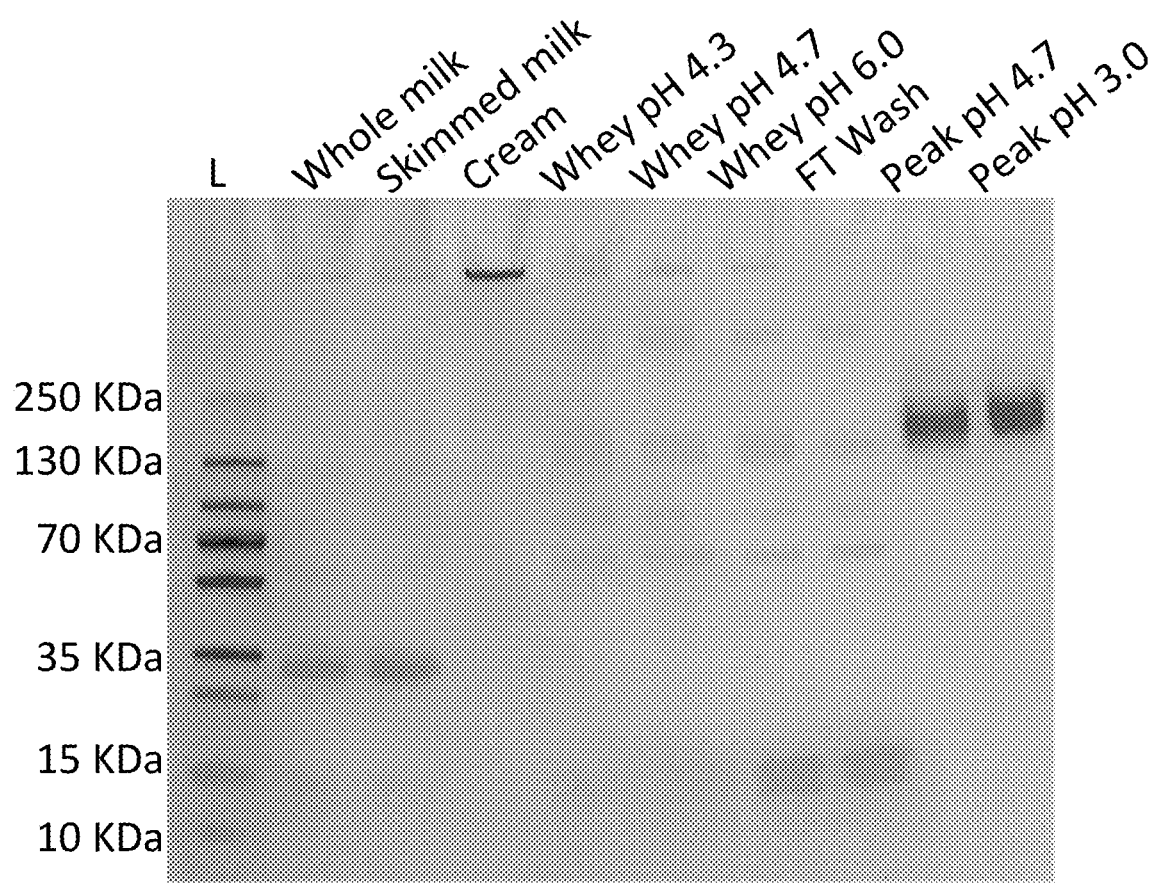
FIG. 26: SDS-PAGE results of the process samples. Native SDS-PAGE results are shown for process samples obtained from milk with antibody. Five (5) µg of proteins were loaded in each well.

Example 1.2 was repeated, but whole goat milk containing 0, 1, 2 or 3 mg/ml of canine monoclonal antibody was treated. The results were identical to those in Example 1. Moreover, we observed that a higher concentration was retrieved from samples with higher heterologous antibody concentrations (FIG. 22).

5. Murine Heterologous Antibody

Example 1.2.a was repeated, but whole goat milk containing monoclonal murine antibody is treated. The results are similar to those in Example 1.2.a (FIG. 23-26).

6. Goat Colostrum Containing Heterologous Antibody

Example 1.2. was repeated for the sample preparation, but goat colostrum was treated. The skimming was identical to those in Example 1.2. Caseins precipitation was not complete at pH 4.3. Precipitated caseins were removed by centrifugation at 3000 g for 15 min at 20° C. The antibodies were mainly found in the supernatant, called whey. Pellet was washed using 5% initial milk volume of 50 mM sodium acetate, 50 mM NaCl at pH 4.3 in order to harvest residual antibody present in caseins pellet. Wash and whey were mixed, adjusted to pH 6 with NaOH 1M and filtered 2 times through 3 m and 0.22 m respectively before the loading on the matrix. The mixture of whey and washes was named "loading sample".

Purification of heterologous antibody was carried out by affinity chromatography using 5 ml cartridge containing protein-A (praesto, purolite). Run was performed as followed: 1 column volume (CV) of the loading sample was loaded on cartridge equilibrated in 50 mM sodium acetate, 500 mM NaCl at pH 6.0 at a flow rate of 1 ml/min. Cartridge was washed with 10 CV with equilibration buffer at a flow rate of 4 ml/min. A first elution was performed using 5 CV of 50 mM sodium acetate, 100 mM NaCl at pH 4.7. The second elution was performed using 5 CV of 100 mM glycine at pH 3.0. Heterologous antibody were collected by 2 mL fraction and neutralized using 200 µL of 1.5 M of Tris-HCl at pH 8.5 to a pH stabilizing antibody. Fractions having the heterologous antibody were pooled.

Monoclonal heterologous antibody concentration was measured by biolayer interferometry (BLI). Proteins were visualized by SDS-PAGE. The residual goat antibody in the final product was measured by ELISA. Recovery yield (%) was calculated using the following equation:

$$\frac{Cf \times Vf}{Ci \times Vi} \times 100$$

Figure 27:
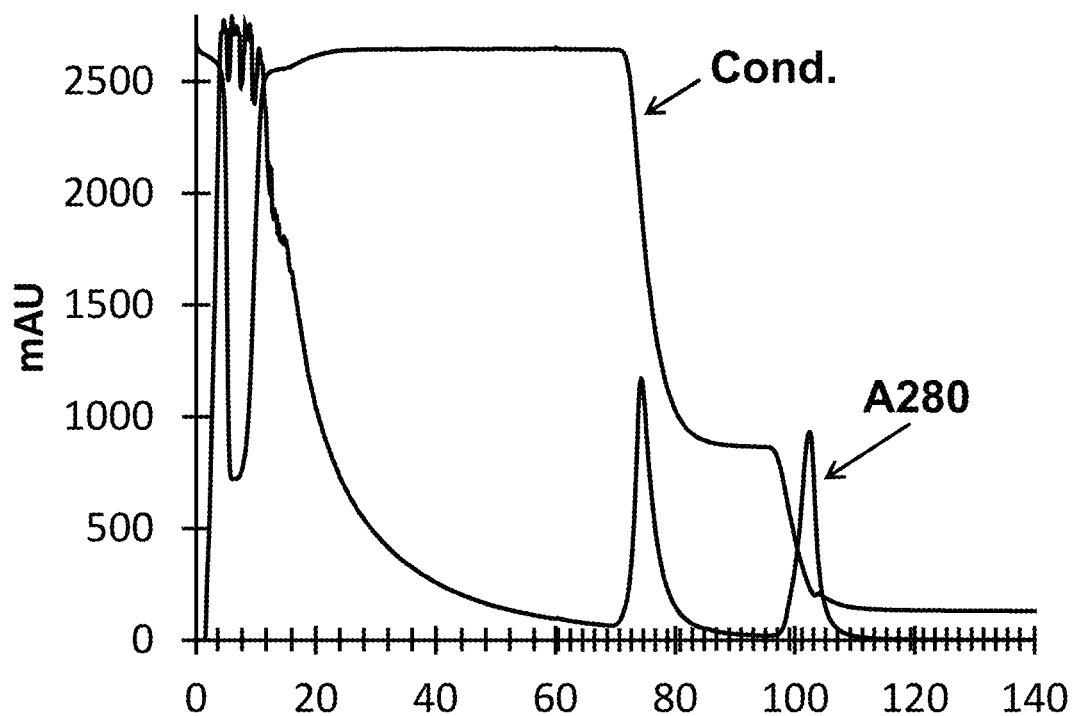
FIG. 27: Chromatogram of the purification by affinity chromatography. The absorbance at 280 nm at the outlet of the column and the conductivity are represented respectively by the lines as indicated. The sample of goat whey is loaded onto the column and then the column is washed with the equilibration buffer at pH 6. Proteins which are not bind to the column are recovered in the flow through (FT) and wash fractions. Elution at pH 4.7 and 3 are applied in order to elute antibodies.

(with Cf=concentration of the molecule of interest in the final product (g/l), Vf=volume of the final product (l), Ci=concentration of the molecule of interest in the initial product which correspond to loading sample (g/l), Vi=volume of the initial product which correspond to loading sample (l)). Chromatogram of the purification is shown in FIG. 27.

Colostrum is a form milk generate just prior to giving birth. Colostrum contains more antibodies than conventional milk. Purification of colostrum confirms that the present process is robust. Indeed, colostrum is the worst case because it contains a lot of goat antibodies (>31 mg/ml compared at 0.25 mg/ml for conventional milk). Result for skimming of colostrum was similar to these for conventional milk: i) the same volume of skimmed colostrum was recovered and ii) the same percentages of goat antibodies and heterologous antibodies were harvested in the skimmed colostrum. However, whereas the precipitation of the caseins of the conventional milk was total at pH 4.3, it was not the case for colostrum: only a portion of caseins precipitated at pH 4.3. On the other hand, the loss of antibodies in the casein pellet was comparable to that of conventional milk.

In the present example, the affinity chromatography was carried out using the 3 steps gradient (pH 6.0, pH 4.7 and pH 3.0). The partially clarified colostrum was injected onto the matrix containing protein A. The chromatogram shows that many proteins do not bind to the matrix (FIG. 27). The SDS-PAGE shows that proteins that do not bind are mainly caseins, α-lactalbumin and β-lactoglobulin (data not shown). The goat antibodies fixed on the column were eluted at pH 4.7. The protein eluted at pH 3 is the heterologous antibody.

From 10 ml of whey containing 2 mg canine monoclonal antibody, >80% of the monoclonal antibody was recovered with a purity of more than >90%.

7. Goat Colostrum

Example 1.1. was repeated for the sample preparation, but goat colostrum was treated. The skimming was identical to those in Example 1.1. Caseins precipitation was not complete at pH 4.3. Precipitated caseins were removed by centrifugation at 3000 g for 15 min at 20° C. The antibodies were mainly found in the supernatant, called whey. Pellet was washed using 5% initial milk volume of 50 mM sodium acetate, 50 mM NaCl at pH 4.3 in order to harvest residual antibody present in caseins pellet. Wash and whey were mixed, adjusted to pH 6 with NaOH 1M and filtered 2 times through 3 m and 0.22 m respectively before the loading on the matrix. The mixture of whey and washes was named "loading sample".

Purification was carried out by affinity chromatography using 5 ml cartridge containing protein-A (praesto, purolite). Run was performed as followed: 1 column volume (CV) of the loading sample was loaded on cartridge equilibrated in 50 mM sodium acetate, 500 mM NaCl at pH 6.0 at a flow rate of 1 ml/min. Cartridge was washed with 10 CV with equilibration buffer at a flow rate of 4 mL/min. A first elution was performed using 5 CV of 50 mM sodium acetate, 100 mM NaCl at pH 4.7. The second elution was performed using 5 CV of 100 mM glycine at pH 3.0.

The goat antibody in the final product was measured by ELISA. Recovery yield (%) was calculated using the following equation:

$$\frac{Cf \times Vf}{Ci \times Vi} \times 100$$

Figure 28:
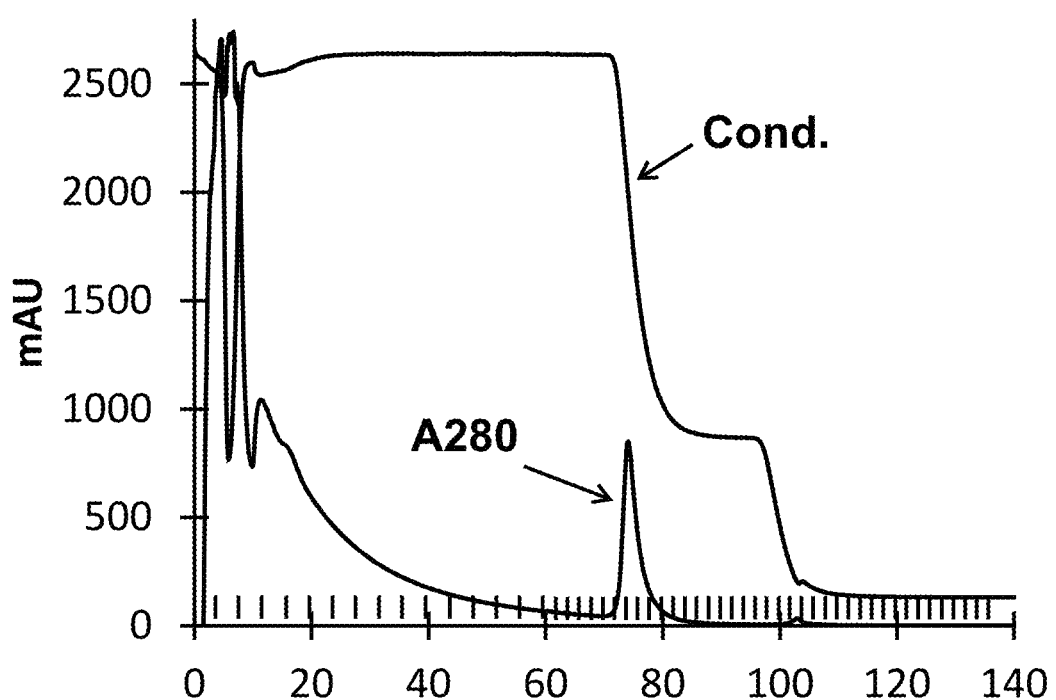
FIG. 28: Chromatogram of the purification by affinity chromatography. The absorbance at 280 nm at the outlet of the column and the conductivity are represented respectively by the lines as indicated. The fractions and fraction numbers are marked in red. The sample of goat whey is loaded onto the column and then the column is washed with the equilibration buffer at pH 6. Proteins which are not bind to the column are recovered in the flow through (FT) and wash fractions. Elution at pH 4.7 and 3 are applied in order to elute antibodies.

(with Cf=concentration of the molecule of interest in the final product (g/l), Vf=volume of the final product (l), Ci=concentration of the molecule of interest in the initial product which correspond to loading sample (g/l), Vi=volume of the initial product which correspond to loading sample (l)). Chromatogram of the purification is shown in FIG. 28.

By monitoring the absorbance at 280 nm on the chromatogram, it is noted that practically all the goat proteins and antibodies were eluted at about pH ≥4.7. This example clearly shows that the stage at about pH 4.7 is necessary. Upon elution at pH 3, a low level of goat antibody was eluted, it is expressed by a small peak of absorbance at 280 nm.

This example, compared with the above example (see FIG. 27), carried out under the same conditions, shows that at pH >3 all the whey colostrum proteins were eluted and that pH=3, the heterologous antibody was eluted.

8. Colostrum and 2 Steps Gradient (pH 6 and pH 3.0) Purification

Example 1.1. was repeated for the sample preparation, but goat colostrum was treated. The skimming was identical to those in example 1.1. Caseins precipitation was not complete at pH 4.3. Precipitated caseins were removed by centrifugation at 3000 g for 15 min at 20° C. The antibodies were mainly found in the supernatant, called whey. Pellet was washed using 5% initial milk volume of 50 mM sodium acetate, 50 mM NaCl at pH 4.3 in order to harvest residual heterologous antibody present in caseins pellet. Wash and whey were mixed, adjusted to pH 6 with NaOH 1M and filtered 2 times through 3 µm and 0.22 µm respectively before the loading on the matrix. The mixture of whey and washes was named "loading sample".

Figure 29:
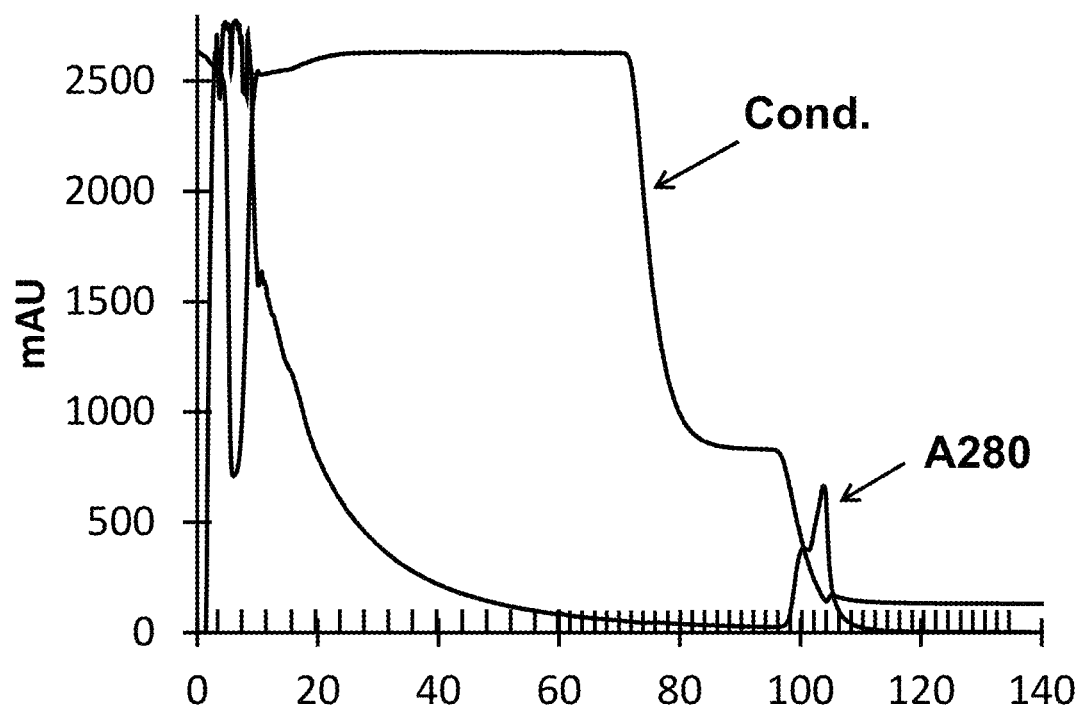
FIG. 29: Chromatogram of the purification by affinity chromatography. The absorbance at 280 nm at the outlet of the column and the conductivity are represented respectively by the lines as indicated. The sample of goat whey is loaded onto the column and then the column is washed with the equilibration buffer at pH 6 then with the equilibration buffer containing 100 mM NaCl. Proteins which are not bind to the column are recovered in the flow through (FT) and washes fractions. Elution at pH 3 are applied in order to elute goat antibodies.

Purification was carried out by affinity chromatography using 5 ml cartridge containing protein-A (praesto, purolite). Run was performed as followed: 1 column volume (CV) of the loading sample was loaded on cartridge equilibrated in 50 mM sodium acetate, 500 mM NaCl at pH 6.0 at a flow rate of 1 ml/min. Cartridge was washed with 10 CV with equilibration buffer at a flow rate of 4 mL/min. Then cartridge was washed with 5 CV with 50 mM sodium acetate, 100 mM NaCl at pH 6.0 at a flow rate of 4 mL/min. The elution was performed using 5 CV of 100 mM glycine at pH 3.0 at a flow rate of 4 ml/min. Chromatogram of the purification is shown in FIG. 29.

This example shows that if a plateau at about pH 4.7 is not carried out, the goat antibodies are eluted at pH=3. As shown in the previous examples, elution at pH 3 elutes the heterologous antibodies.

In order for the heterologous antibodies to be recovered at a high purity level, a plateau at about pH 4.7 is advantageous.

9. Dilution of the Whey Before Loading

Example 4 section 2.a.ii is repeated but pH of the whey was reached not only at pH 6 but also at pH 6.5 and 7.0 with acetate 1 M pH 7.5. This pH adjustment induced whey sample volume to increase from 17 ml undiluted to 117 ml, 436.7 ml and 1354 ml at pH 6, 6.5 and 7.0, respectively. Samples were then loaded on the protein A resin. The results were identical to those in Example 4 section 2.a.ii.

Example 6: Assays Used in Examples 1-5

1. ELISA a) Heterologous Antibody

The ELISA protocol used is as follows. Affinity purified Sheep anti-Dog IgG (LabNed LN0801904) was loaded in amount 0.5 µg on a polystyrene microtiter plate in carbonate buffer 0.05M pH 9.6 and incubated at 4° C., overnight. Saturation of wells was performed by incubation (min. 30 min at RT) in 50 mM Tris, 0.14 M NaCl, 1% BSA, pH 8 (TBS-BSA). After 5 washing steps with TBS-T buffer (0.1% Tween 20), standards (affinity-purified heterologous antibody) or samples are added in the wells and incubated for 1 h at RT. Next, wells were washed and the same procedure was followed for the incubation of 1 µg of neutralite avidin-conjugated sheep anti-dog IgG (Bethyl Lab, in house coupling). Each of these steps was preceded and followed by five washes in TBS-T, to remove unbound mAb. TMB was used as substrate to measure immobilised peroxidase activity and the reaction is stopped using H3PO4 1 M. Plate was read at 450 nm. Standard curve is plotted (OD versus concentration) and a 4 parameter logistic curve was modelized. Sample concentrations were determined using the equation of the standard curve.

b) Caprine Antibody

The ELISA protocol used is based on that provided by the kit "Goat IgG ELISA Quantification Set" ((Bethyl Laboratories, Inc.). Affinity purified Rabbit anti-Goat IgG-Fc (Bethyl Laboratories, Inc.) was loaded in amount 0.5 µg on a polystyrene microtiter plate and incubated at 4° C., overnight. Saturation of wells was performed by incubation (1 h at RT) in 50 mM Tris, 0.14 M NaCl, 0.1% tween 20, pH 8 (TBS-T). Standard (Goat Reference Serum, Bethyl Laboratories, Inc.) or sample are added in the well and incubated for 1 h at RT. After, the same procedure was followed for the incubation of 1 µg of HRP Conjugated Rabbit anti-Goat IgG-Fc Detection Antibody (Bethyl Laboratories, Inc.). Each of these steps was preceded and followed by five washes in TBS-T, to remove unbound mAb. TMB was used as substrate to measure immobilised peroxidase activity and the reaction is stopped using H2SO4 0.18 M. Plate was read at 450 nm. Standard curve is plotted (OD versus concentration) and a 4 parameter logistic curve was modelized. Sample concentrations were determined using the equation of the standard curve.

2. BLI a) Heterologous Antibody

The quantification of heterologous antibody was determined using an Octet HTX System (ForteBio, Pall Life Sciences, Menlo Park, Calif.). Samples, standards or buffer were dispensed into 96-well microtiter plates (Greiner Bio-one) at a volume of 200 µL per well. Operating temperature was maintained at 25° C. Protein-A-coated biosensor tips (ForteBio, Inc., Menlo Park, Calif.) were pre-wetted for 10 min with TRIS 50 mM, NaCl 140 mM, 0.1% BSA, 0.05% tween 20, 0.05% azide at pH 8.0. Standard curves were constructed by diluting the purified antibody at concentrations from 0 to 150 µg/mL (150 µg/ml, 100 µg/ml, 75 µg/ml, 50 µg/ml, 10 µg/ml, 5 µg/ml, 1 µg/ml and 0 µg/ml (blank)) in 50 mM Tris, 140 mM NaCl, 0.1% BSA, 0.05% tween 20, pH 8 (neutralization buffer). For each assay, 2 replicates of 8 point standard curves were generated by dipping the tips in each standard for 60 sec with 1000 RPM shaking of microplate. Measure of sample binding rates were performed by dipping the tips in sample diluted in neutralization buffer to fall within the concentration range of the standards for 60 sec at 1000 rpm. Sensors were regenerated after each measure by dipping successively the tips 3 times in 10 mM Glycine at pH 1.7 then in neutralization buffer with 400 rpm and 1000 rpm shaking of microplate respectively for 5 sec for each buffer. Data are loaded into Octet Data Analysis 4.0 and analyzed using the initial slope rate equation.

3. BCA

Total protein content was measured by BCA Pierce assay, microplate protocol, from ThermoFisher (Cat #23225). Standard curve was prepared using bovine serum albumin reference at concentrations of 1500-1000-750-500-250-125-25 and 0 µg/ml in PBS. Sample are diluted in PBS to fall within the concentration range of the standards. Next, both standards and samples were deposited in a flat-bottom 96-well clear microplate, 25 µl per sample in triplicate. Reagent solution is then prepared by mixing 50 parts of reagent A with 1 part of reagent B, then 200 µl of this solution is deposited in each well and the microplate is incubated at 37° C. for 30 min. After letting the plate cool to room temperature, the OD at 570 nm was read. Standard curve was plotted (OD versus concentration) and a linear regression curve was modelized. Sample concentrations were determined using the equation of the standard curve.

4. SDS-PAGE/Western Blots

Purity and impurities were determined using gel electrophoresis SDS-PAGE as follows. Precast gels (4-20%, Biorad Criterion) were prepared according to manufacturer instructions and mounted on the device to run the gel. TGX buffer was prepared from TGX 10× buffer (Biorad) by diluting it in water, then this buffer was added into the electrophoresis tank. Samples were diluted and prepared by mixing with loading buffer (reduced or not reduced) in a 1:1 ratio. For native conditions gels, samples were not heated, but in other cases samples were heated for 5 min at 90° C. before to be centrifuged and deposited on the gel. Five microliters of the protein ladder (ThermoFisher) were deposited in the first well of the gel, then 15 l of each sample were added in following wells. Gel was then run at 200V for 35-40 min before to be rinsed with water 3 times for 5 min and incubated with the coloring solution (Bio-safe Coomassie, Bio-rad) for 1 hour. Next, gel was decolored with water, 1 hour for the first rinsing and then overnight at room temperature. A picture of the gel was then taken with a camera and the gel was analysed.

For Western Blot analysis, proteins in the gel were transferred on a PVDF membrane using a blotter. After blocking the membrane, anti-heterologous antibody conjugated to Alkaline Phosphatase was incubated, the membrane was washed and then revealed with AEC. The membrane was then pictured for ongoing analysis.

5. EC

Purity of purified products was determined using a capillary electrophoresis device (Experion, Biorad). Protein chips (Experion, Bio-rad) were prepared with the running gel according to the manufacturer instructions. Samples were prepared by mixing their with loading reagent (reduced or not) and then heated at 95° C. for 5 min. Samples were then loaded onto the chip that was then placed in the capillary electrophoresis device. During the run, fluorescence is detected to identify protein peaks and intensity. After running the experiment, a reconstituted gel electrophoresis profile is generated with a table compiling all appearing bands, molecular weights and relative purity.

6. HCP (Goat Milk Proteins ELISA)

The goat milk protein assay is a sandwich immunoenzymetric assay (Cygnus Technologies, Cat #F240). An affinity purified capture polyclonal antibody (against 30 milk proteins) is pre-coated by the manufacturer in a 96-well ELISA microplate which is then washed, saturated and stabilized. The preparation of samples is performed so that they are in the range of the ELISA, between 0 and 25 ng/ml goat milk proteins. Standards and samples are then deposited 25 µl per well in duplicate. Anti-goat milk antibody conjugated to HRP is then added to the well, 100 µl/well. After an incubation of 2 hours at RT on rotator at 500 rpm, wells are washed 4 times with 350 µl of washing buffer. Finally, 100 µl of TMB substrate is added to all wells, allowed to react for 30 minutes and stopped with 100 µl of stop solution. The plate is then read at 450 and 650 nm and concentrations of goat milk proteins are performed following the same principle as for heterologous antibody ELISA.

Example 7: Purification of Different Heterologous Antibodies

Purification of goat milk containing a canine monoclonal heterologous antibody no 1 is compared to the purification of goat milk containing a canine monoclonal heterologous antibody no 2. Heterologous antibody no 1 exhibits ~85% of sequence identity with the heterologous antibody no 2.

Example 1.2 was repeated for the sample preparation: Whole goat milk containing ~1 g/l canine monoclonal heterologous antibody was heated at 50° C. then centrifuged at 3000 g for 10 min. The flask was cooled in order to solidify the fat. The cream at the top of the flask was removed. Skimmed milk caseins were precipitated at 20° C. by addition of HCl 1 M until pH 4.3. Precipitated caseins were removed by centrifugation at 3000 g for 20 min at 20° C.

Pellet was washed using 5% initial milk volume of 50 mM sodium acetate, 50 mM NaCl at pH 5 in order to harvest residual heterologous antibody present in caseins pellet. Washes and whey were mixed, adjusted to pH 6 with NaOH 1M and filtered through 0.22 m before the loading on the chromatography matrix. The mixture of whey and washes is named "loading sample". The volume of milk obtained after each step was determined by weighing.

Figure 30:
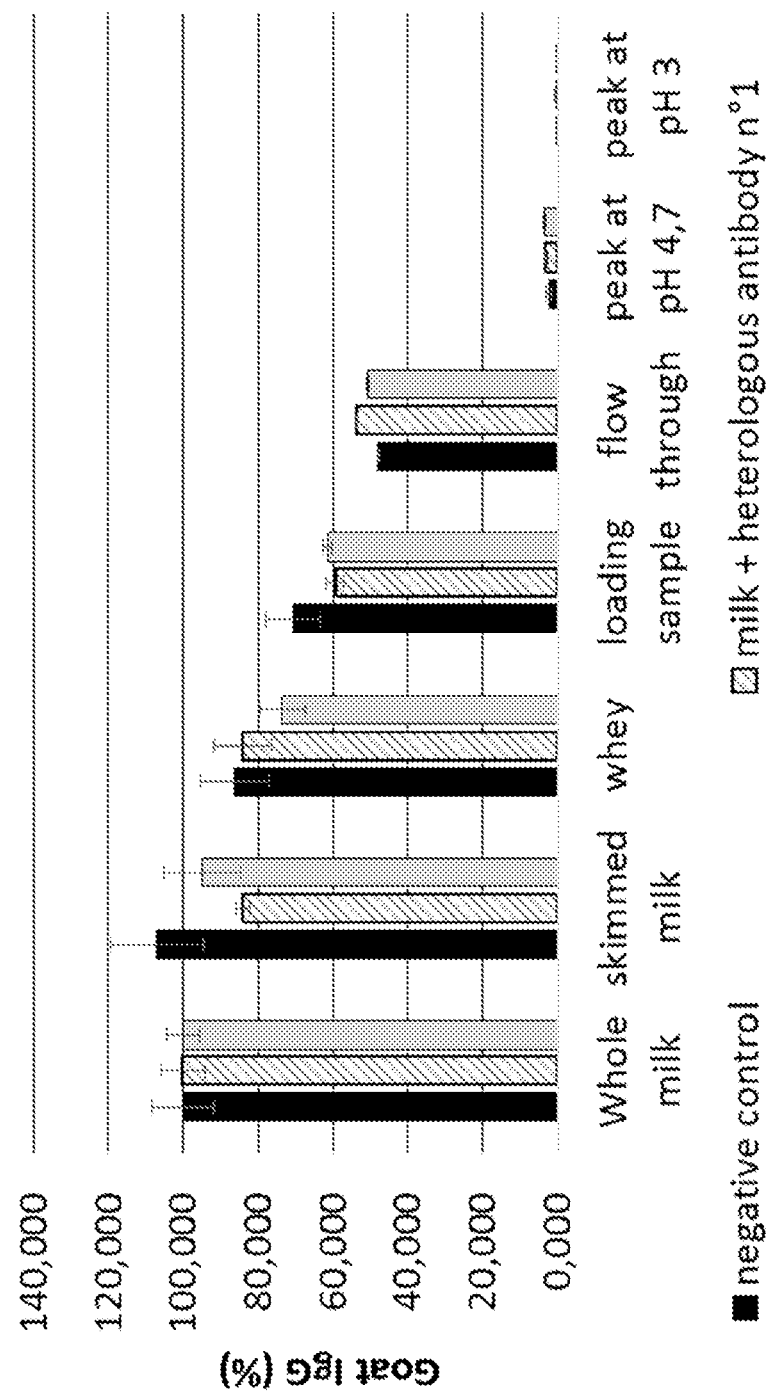
FIG. 30: Comparison of recovery yields of goat IgG during different steps of milk treatment.
Figure 31A:
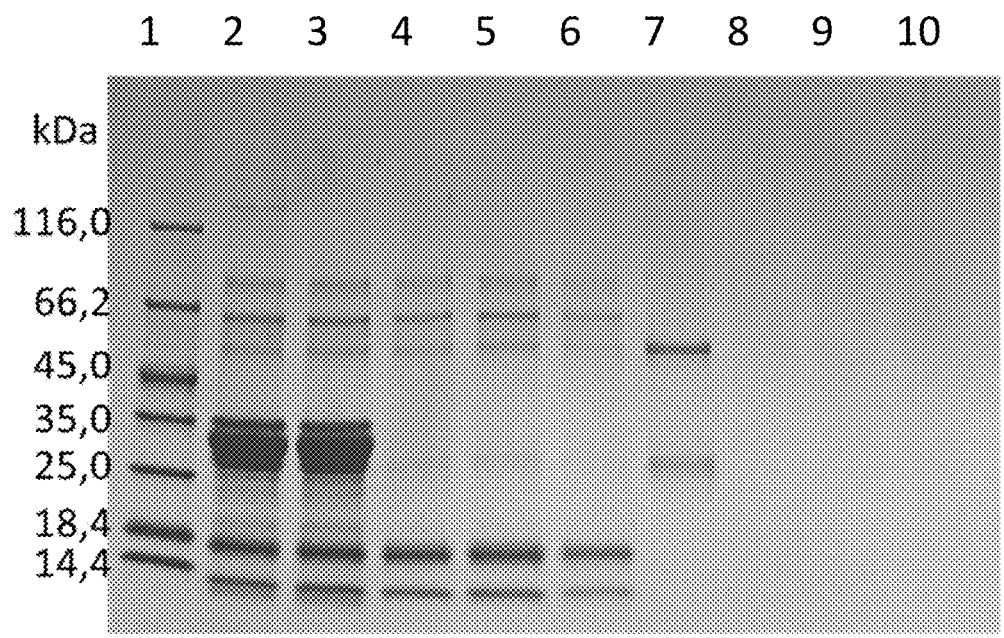
FIGS. 31A-31C: SDS-PAGE analysis (reduced conditions). The description of the samples loaded is reported in Table 8.
Figure 31B:
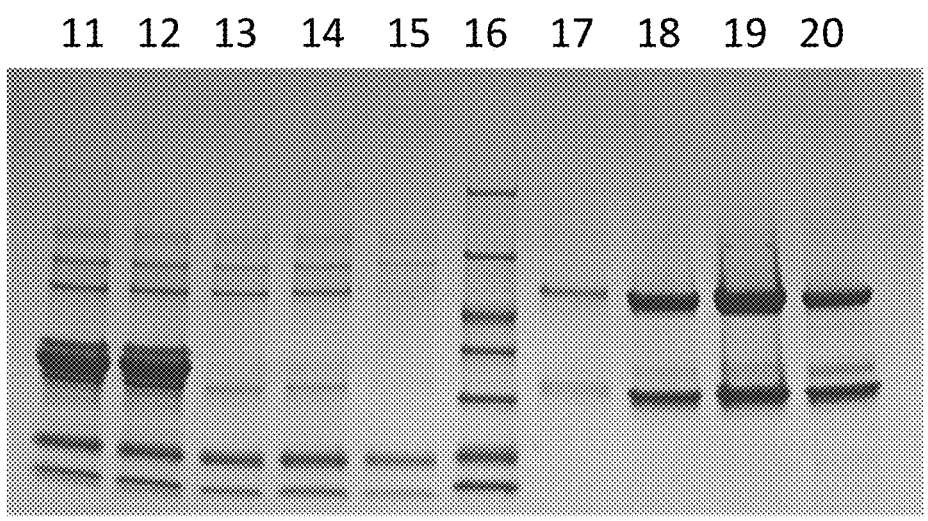
Figure 31C:
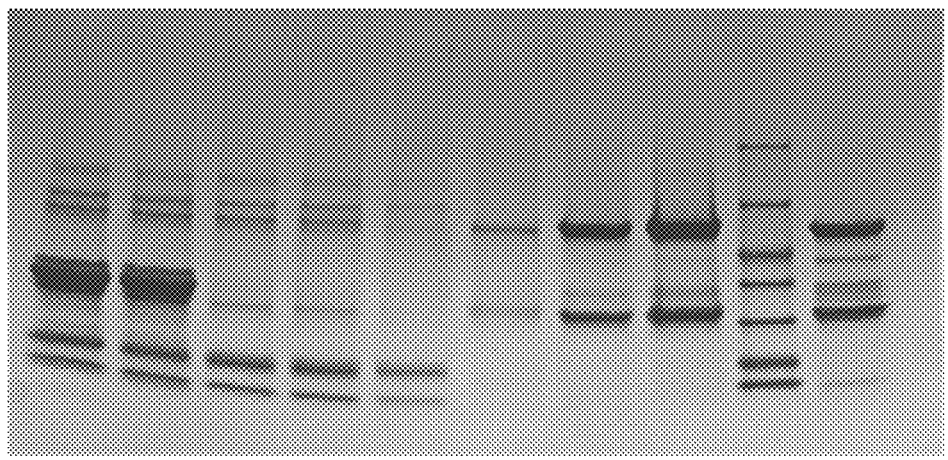

When preparing the "loading samples", goat milk containing heterologous antibody no 1 behaved like goat milk containing heterologous antibody no 2. Indeed, the skimming and caseins precipitation were performed under identical conditions and identical results were observed for the 2 samples: i) the same volumes of skimmed milk and whey were recovered: From 42 ml of whole milk, more than 90% of skimmed milk was harvested and more than 85% of whey was harvested. A dead volume is lost during filtration so 85% of loading sample is recovered, ii) the same quantities of goat antibodies were recovered. The goat antibody concentration measured by ELISA is reported in FIG. 30, iii) SDS-PAGE analysis for milk samples show the same profile (FIG. 31 and Table 8).

Figure 32:
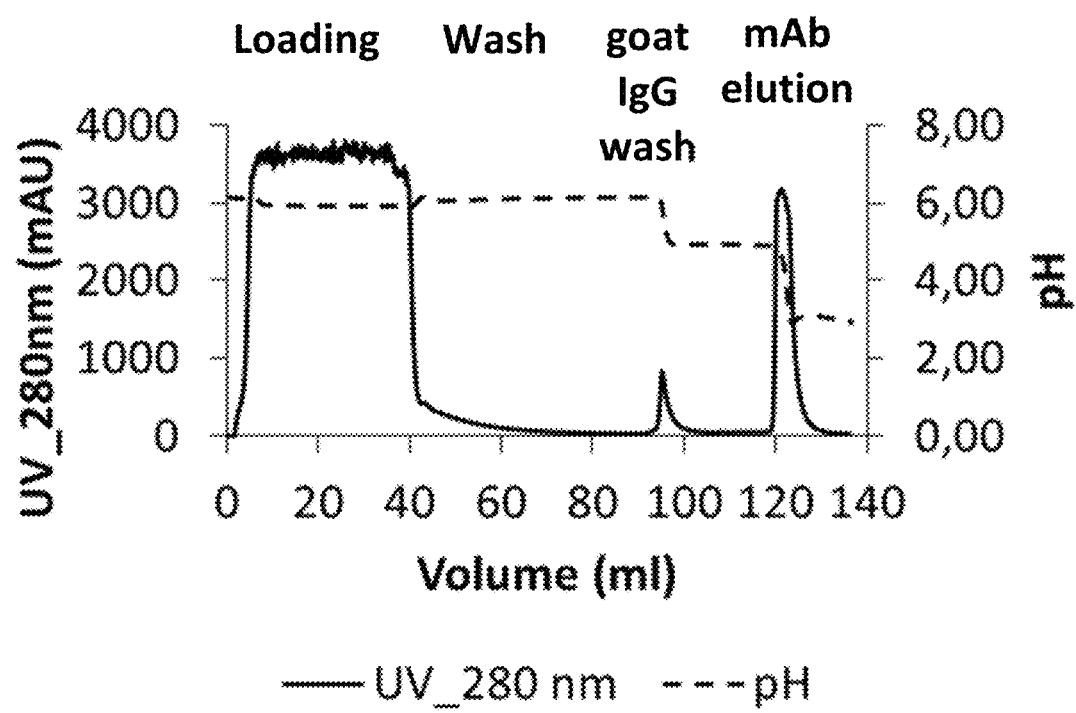
FIG. 32: Chromatogram of the purification by affinity chromatography using the Praesto AP Minichrom resin. The absorbance at 280 nm at the outlet of the column and the pH are represented respectively by lines as indicated. The sample containing heterologous antibody no 1 was loaded onto the column and then the column was washed with the equilibration buffer at pH 6. Proteins which were not bound to the column were recovered in the flow through and wash fractions. Step gradients at pH 4.7 and 3 were applied in order to harvest the goat IgG (peak retention volume=95 ml) and heterologous antibody no 1 (peak retention volume=121 ml) respectively.
Figure 33:
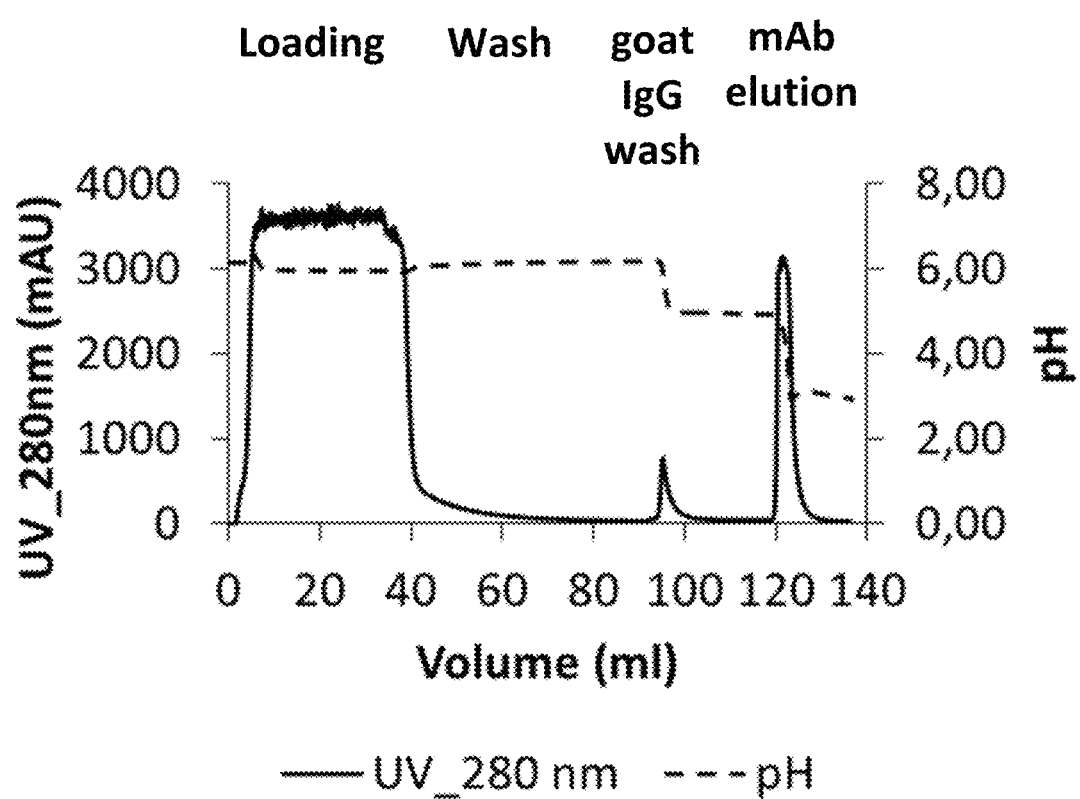
FIG. 33: Chromatogram of the purification by affinity chromatography using the Praesto AP Minichrom resin. The absorbance at 280 nm at the outlet of the column and the pH are represented respectively by lines as indicated. The sample containing heterologous antibody no 2 was loaded onto the column and then the column was washed with the equilibration buffer at pH 6. Proteins which were not bound to the column were recovered in the flow through and wash fractions. Step gradients at pH 4.7 and 3 were applied in order to harvest the goat IgG (peak retention volume=95 ml) and heterologous antibody n°2 (retention volume=121 ml) respectively.

Purification of heterologous antibody was carried out by affinity chromatography using 5 ml cartridge containing protein-A (Praesto AP Minichrom (purolite)). Run was performed as follows: 7 column volumes (CV) of the loading sample were loaded at a flow rate of 1 ml/min on cartridge equilibrated in 50 mM sodium acetate, 500 mM NaCl at pH 6.0. Cartridge was washed with 10 CV at a flow rate of 4 ml/min with equilibration buffer. A second wash was performed using 5 CV of 50 mM sodium acetate, 100 mM NaCl at pH 4.7 at a flow rate of 4 ml/min. The elution was performed using 5 CV of 100 mM glycine at pH 3.0 at a flow rate of 4 ml/min. Purification chromatograms of the heterologous antibody no 1 and no 2 are reported in FIG. 32 and FIG. 33 respectively. Peaks are integrated with the help of the Unicorn software.

Figure 34:
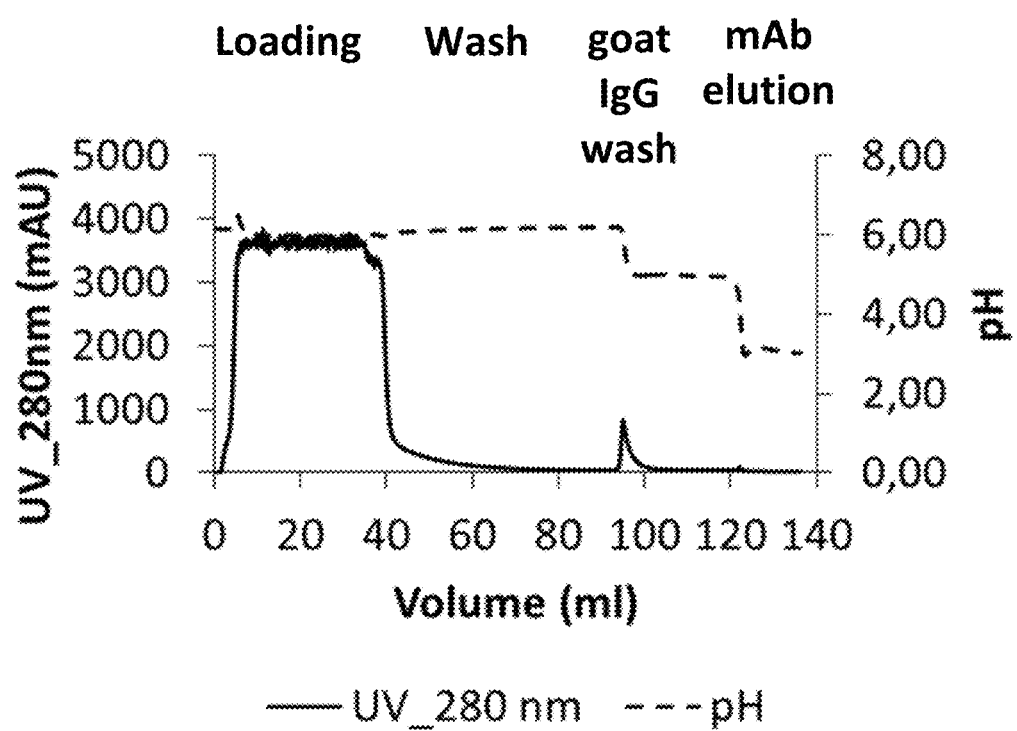
FIG. 34: Chromatogram of the purification by affinity chromatography using the Praesto AP Minichrom resin. The absorbance at 280 nm at the outlet of the column and the pH are represented respectively by lines as indicated. The sample without heterologous antibody was loaded onto the column and then the column was washed with the equilibration buffer at pH 6. Proteins which were not bound to the column were recovered in the flow through and wash fractions. Step gradients at pH 4.7 and 3 were applied in order to harvest the goat IgG (peak retention volume=99 ml) and residual goat proteins (retention volume=122 ml) respectively.

A negative control (goat milk without heterologous antibody) is treated and purified according to the same parameters as described above. The chromatogram of the purification of the negative control is reported in FIG. 34.

TABLE 8

Description of the samples loaded on the gels of FIG. 31.
The marker is Thermo Scientific ™ Pierce ™ Unstained
Protein Molecular Weight Marker (# 11882114).

| well | Loading volume (µl) | Loading sample on gels | Sample from | Total dilution of the loading sample |
|---|---|---|---|---|
| 1 | 10 | Protein Molecular Weight Marker | / | / |
| 2 | 10 | Whole milk | Negative control | 1/40 |
| 3 | 10 | Skimmed milk | Negative control | 1/40 |
| 4 | 10 | Whey | Negative control | 1/40 |
| 5 | 10 | Loading sample | Negative control | 1/40 |
| 6 | 10 | Flow through | Negative control | 1/40 |
| 7 | 10 | Step at pH 4.7 | Negative control | 1/2 |
| 8 | 10 | Step at pH 3.0 | Negative control | 1/2 |
| 9 | 20 | Step at pH 3.0 | Negative control | 1/2 |
| 10 | 10 | Step at pH 3.0 | Negative control | 1/2 |
| 11 | 10 | Whole milk | Sample containing heterologous antibody n° 1 | 1/40 |
| 12 | 10 | Skimmed milk | Sample containing heterologous antibody n° 1 | 1/40 |
| 13 | 10 | Whey | Sample containing heterologous antibody n° 1 | 1/40 |
| 14 | 10 | Loading sample | Sample containing heterologous antibody n° 1 | 1/40 |
| 15 | 10 | Flow through | Sample containing heterologous antibody n° 1 | 1/40 |
| 16 | 10 | Protein Molecular Weight Marker | / | / |
| 17 | 10 | Step at pH 4.7 | Sample containing heterologous antibody n° 1 | 1/2 |
| 18 | 10 | Elution at pH 3 | Sample containing heterologous antibody n° 1 | 1/2 |
| 19 | 20 | Elution at pH 3 | Sample containing heterologous antibody n° 1 | 1/2 |
| 20 | 10 | Purified reference heterologous antibody n° 1 (10 µg) | / | / |
| 21 | 10 | Whole milk | Sample containing heterologous antibody n° 2 | 1/40 |
| 22 | 10 | Skimmed milk | Sample containing heterologous antibody n° 2 | 1/40 |
| 23 | 10 | Whey | Sample containing heterologous antibody n° 2 | 1/40 |

TABLE 8-continued

Description of the samples loaded on the gels of FIG. 31.
The marker is Thermo Scientific™ Pierce™ Unstained
Protein Molecular Weight Marker (# 11882114).

| well | Loading volume (μl) | Loading sample on gels | Sample from | Total dilution of the loading sample |
|---|---|---|---|---|
| 24 | 10 | Loading sample | Sample containing heterologous antibody n° 2 | 1/40 |
| 25 | 10 | Flow through | Sample containing heterologous antibody n° 2 | 1/40 |
| 26 | 10 | Step at pH 4.7 | Sample containing heterologous antibody n° 2 | 1/2 |
| 27 | 10 | Elution at pH 3 | Sample containing heterologous antibody n° 2 | 1/2 |
| 28 | 20 | Elution at pH 3 | Sample containing heterologous antibody n° 2 | 1/2 |
| 29 | 10 | Protein Molecular Weight Marker | / | / |
| 30 | 10 | Purified reference heterologous antibody n° 2 (10 μg) | / | / |

Figure 35A:
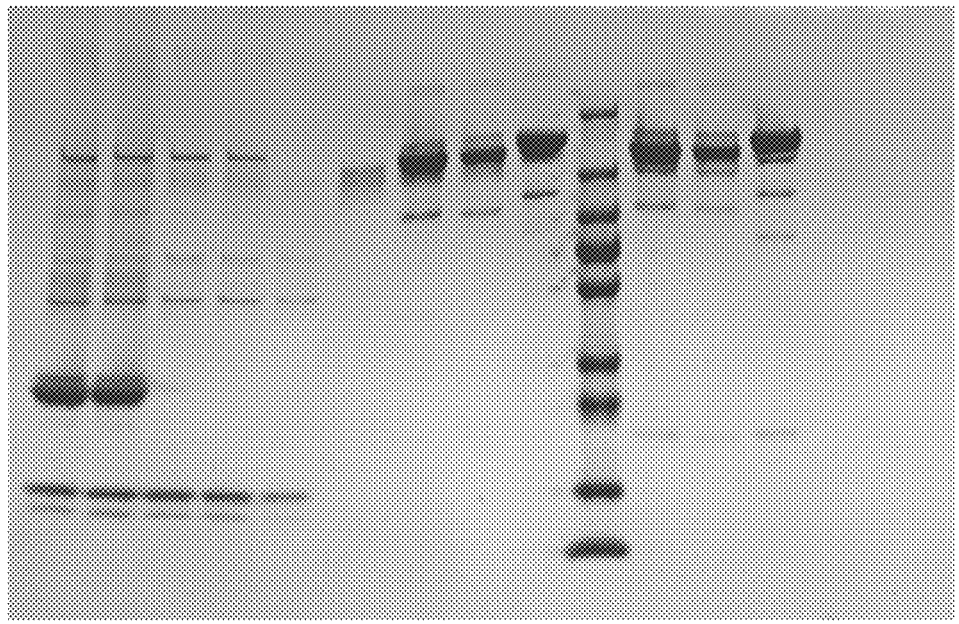
Figure 35B:
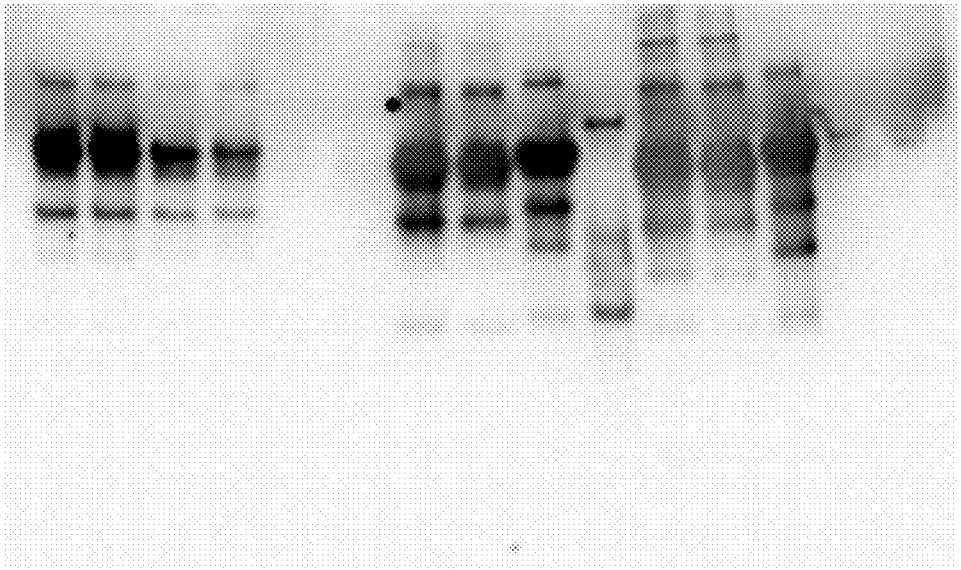

Monoclonal heterologous antibody concentration was measured by enzyme-linked immunosorbent assay (ELISA). Proteins were visualized by SDS-polyacrylamide gel electrophoresis (SDS-PAGE) (FIG. 31 and FIG. 35). Monoclonal heterologous antibody was visualized by western Blot (FIG. 35). The goat antibody concentration was measured by ELISA (FIG. 30). Recovery yield (%) was calculated using the following equation: $(C_f \times V_f)/(C_i \times V_i) \times 100$ (with $C_f$=concentration of molecule of interest in the final product (g/l), $V_f$=volume of the final product (l), $C_i$=concentration of molecule of interest in the initial product (g/l), $V_i$=volume of initial product (l)).

Chromatograms and SDS-PAGE analysis show that goat proteins (including goat antibodies) loaded were mainly harvested in the flow through and washes (FIGS. 30-35). Around 3.5% of goat antibodies loaded were harvested in step gradient at pH 4.7 (peak retention volume=99 ml). Conversely, as shown by canine western blot, heterologous antibody having high affinity for protein-A resin was weakly lost in the flow through, washes and step gradient at pH 4.7 (FIG. 35). Canine ELISA reveals that more than 80% of the monoclonal antibody no 1 and no 2 loaded were harvested in elution at pH 3 (peak retention volume=121 ml). Purification of the negative control indicates that residual goat proteins are eluted in step gradient at pH 3 (peak retention volume=122 ml, FIG. 34). The small peak area (more than 280 times weaker than the elution peak at pH 3 for purification of antibody no 1 or 2) and no detectable band by SDS-PAGE analysis prove that this amount of residual proteins is small and negligible compared to purified heterologous antibody no 1 and 2.

The results are identical for the purification of heterologous antibody no 1 and no 2. These results prove the robustness of the steps of milk treatment and the purification of heterologous antibodies in goat milk.

TABLE 9

Description of the samples loaded on the gels of FIG. 35.
The marker is PageRuler™ Plus Prestained
Protein Ladder, 10 to 250 kDa (ThermoFisher # 26619).

| well | Loading volume (μl) | Loading sample on gel | Sample from | Total dilution of the loading sample |
|---|---|---|---|---|
| 1 | 10 | Whole milk | Sample containing heterologous antibody n° 2 | 1/40 |
| 2 | 10 | Skimmed milk | Sample containing heterologous antibody n° 2 | 1/40 |
| 3 | 10 | Whey | Sample containing heterologous antibody n° 2 | 1/40 |
| 4 | 10 | Loading sample | Sample containing heterologous antibody n° 2 | 1/40 |
| 5 | 10 | Flow through | Sample containing heterologous antibody n° 2 | 1/40 |
| 6 | 10 | Step at pH 4.7 | Sample containing heterologous antibody n° 2 | 1/2 |
| 7 | 10 | elution at pH 3.0 | Sample containing heterologous antibody n° 2 | 1/2 |
| 8 | 5 | elution at pH 3.0 | Sample containing heterologous antibody n° 2 | 1/2 |
| 9 | 10 | Purified reference heterologous antibody n° 2 (10 μg) | / | / |
| 10 | 10 | Protein Molecular Weight Marker | / | / |
| 11 | 10 | elution at pH 3.0 | Sample containing heterologous antibody n° 1 | 1/2 |
| 12 | 5 | elution at pH 3.0 | Sample containing heterologous antibody n° 1 | 1/2 |
| 13 | 10 | Purified reference heterologous antibody n° 1 (10 μg) | / | / |
| 14 | 10 | Step at pH 3.0 | Negative control | 1/2 |
| 15 | 15 | Step at pH 3.0 | Negative control | 1/2 |

Example 8: Purification with Different Protein a Matrix

1. Linear Gradient

Example 1.2 was repeated for the sample preparation: Whole fresh goat milk containing canine monoclonal heterologous antibody (1 mg/ml) was heated at 50° C. then centrifuged at 3000 g for 10 min. The flask was cooled in order to solidify the fat. The cream at the top of the flask was removed. Skimmed milk caseins were precipitated at 20° C. by addition of HCl 1M until pH 4.3. Precipitated caseins were removed by centrifugation at 3000 g for 15 min at 20° C. The supernatant (called whey) was adjusted to pH 6 with NaOH 1M and filtered through 0.22 μm before the loading on the chromatography matrix.

Figure 36:
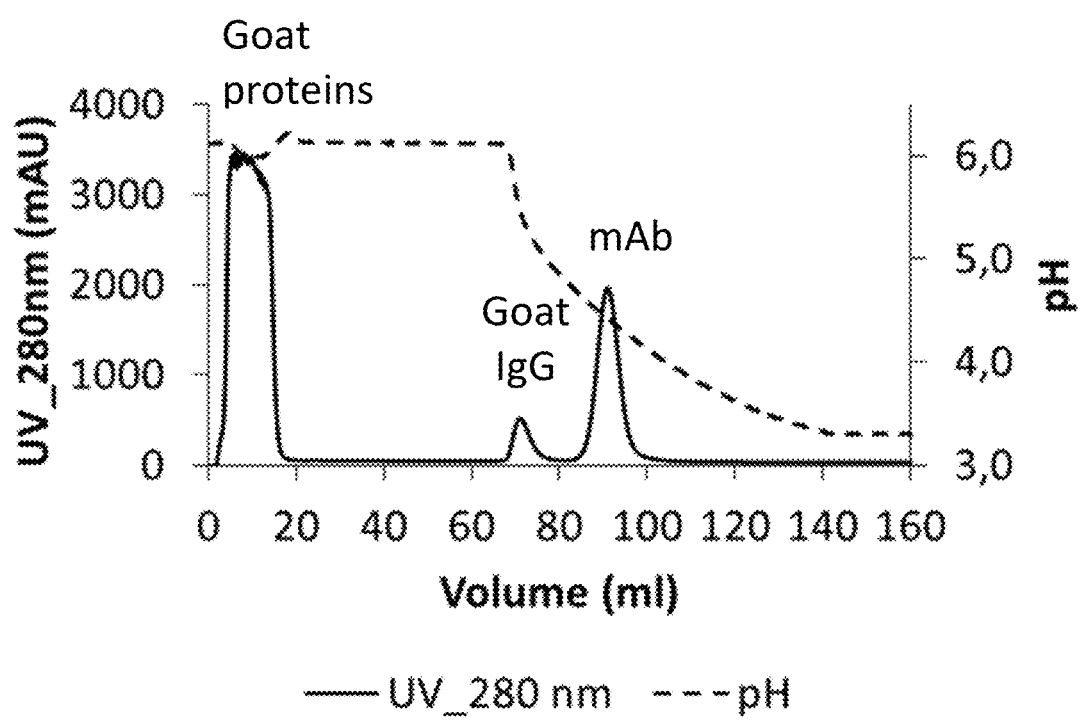
FIG. 36: Chromatogram of the purification by affinity chromatography using the MabSelect PrismA resin. The absorbance at 280 nm at the outlet of the column and the pH are represented respectively by lines as indicated. The sample containing the heterologous antibody was loaded onto the column and then the column was washed with the equilibration buffer at pH 6. Proteins which were not bound to the column were recovered in the flow through and wash fraction. A linear gradient of pH 6 to 3 was applied. Goat IgG Western Blot analysis of the purification is reported in FIG. 40.
Figure 40:
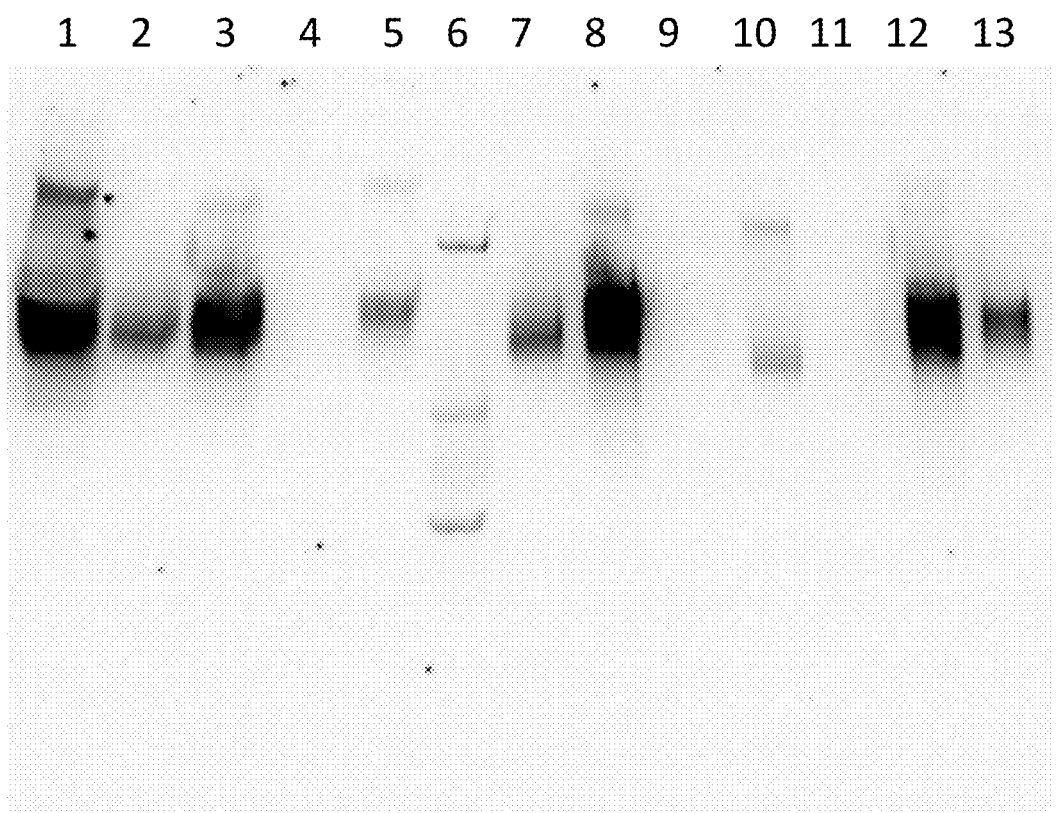
FIG. 40: Goat IgG WB analysis (not reduced conditions) of the purification by affinity chromatography using the MabSelect PrismA resin (chromatograms from FIG. 36 and FIG. 39). The description of the samples loaded is reported in Table 10.

Purification of heterologous antibody was carried out by affinity chromatography using 5 ml cartridge containing protein-A (HiTrap MabSelect PrismA, GE Healthcare). Run was performed as follows: 2 column volumes (CV) of the sample was loaded at a flow rate of 1 ml/min on cartridge equilibrated in 50 mM sodium acetate, 50 mM NaCl at pH 6.0. Cartridge was washed with 10 CV with equilibration buffer at a flow rate of 2.5 ml/min. Elution was performed with a linear gradient of 10 CV between equilibration buffer and 0.1 M sodium citrate at pH 3 at a flow rate of 2.5 ml/min. Fractions eluted at pH <4.8 are neutralized using 1M Tris-HCl at pH 8.5. Chromatogram is reported in FIG. 36. Proteins and heterologous antibody of loading sample, flow through, fractions collected at pH >4.8 (peak retention volume=~70 ml) and fractions collected at pH <4.8 (peak retention volume=~92 ml) are analysed by SDS-PAGE and western Blot (FIG. 40). Monoclonal heterologous antibody concentration was measured by bio-layer interferometry (BLI). Recovery yield of mAb (%) was calculated using the following equation: $(Cf \times Vf)/(Ci \times Vi) \times 100$ (with Cf=concentration of mAb in the final product (g/l), Vf=volume of the final product (l), Ci=concentration of mAb in the loading sample (g/l), Vi=volume of the loading sample (l)). BLI reveals that more than 80% of the monoclonal antibody loaded were harvested in fractions collected at pH <4.8 (peak retention volume=~92 ml).

Two other purifications were performed by i) loading clarified goat milk (without heterologous antibody) and ii) heterologous antibody at 1 g/l in phosphate buffer saline (PBS) at pH 7.2 using the same purification parameters as described above. Chromatograms are reported in FIG. 37 and FIG. 38 respectively.

Figure 37:
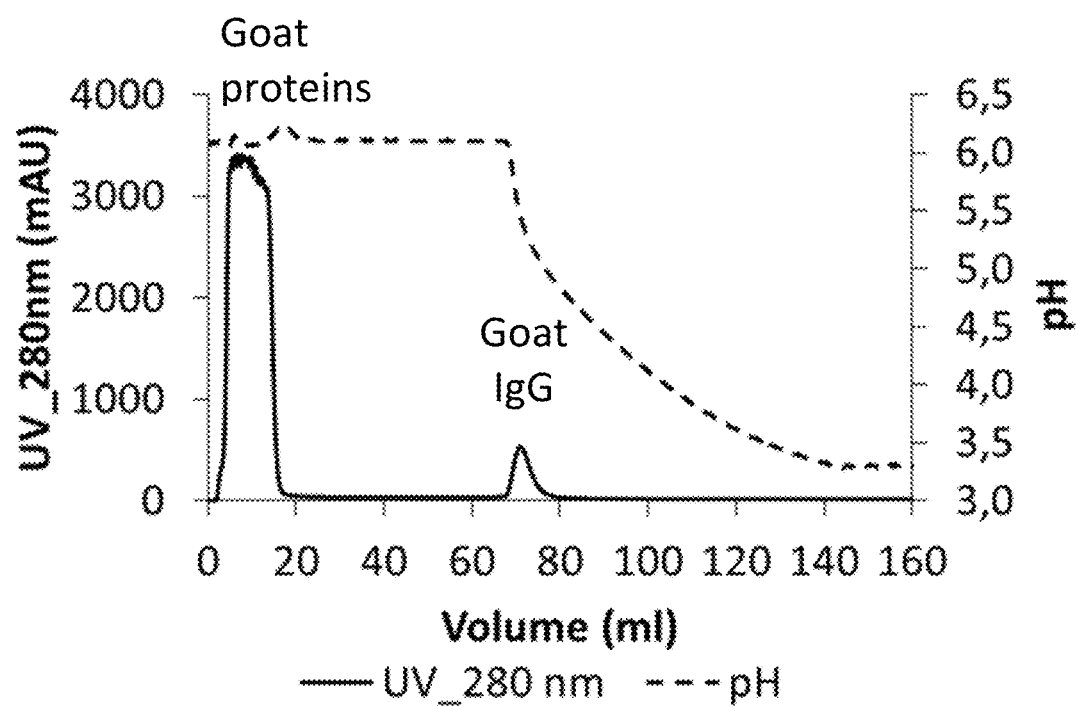
FIG. 37: Chromatogram of the purification by affinity chromatography using the MabSelect PrismA resin. The absorbance at 280 nm at the outlet of the column and the pH are represented respectively by lines as indicated. The sample without heterologous antibody was loaded onto the column and then the column was washed with the equilibration buffer at pH 6. Proteins which were not bound to the column were recovered in the flow through and wash fraction. A linear gradient of pH 6 to 3 was applied.
Figure 38:
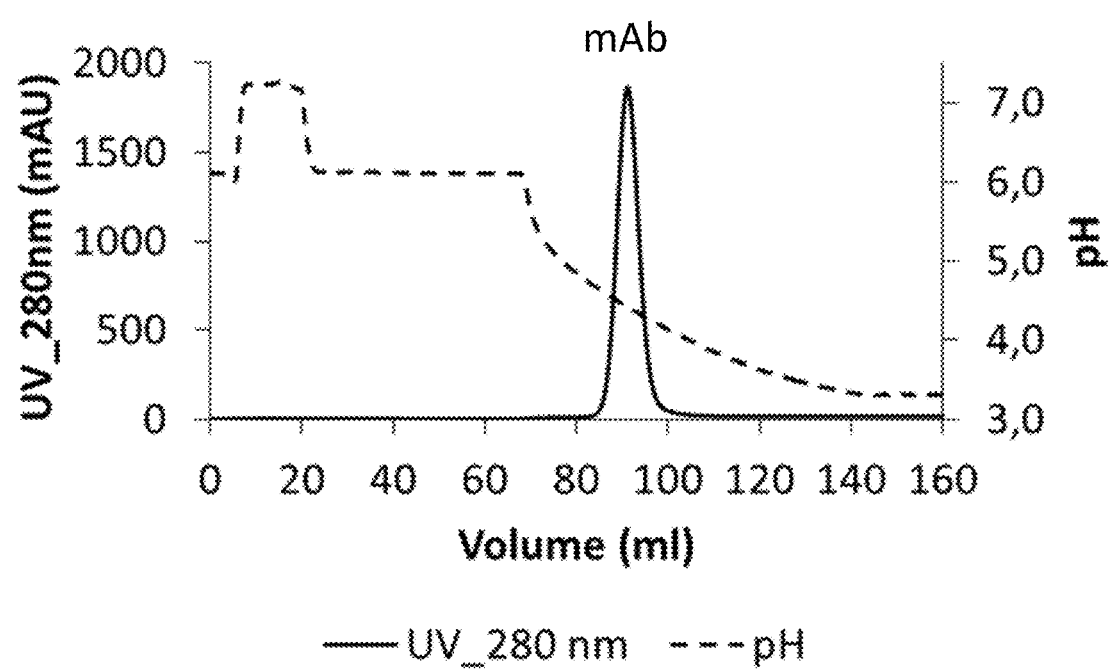
FIG. 38: Chromatogram of the purification by affinity chromatography using the MabSelect PrismA resin. The absorbance at 280 nm at the outlet of the column and the pH are represented respectively by lines as indicated. The sample (heterologous antibody in buffer) was loaded onto the column and then the column was washed with the equilibration buffer at pH 6. Proteins which were not bound to the column were recovered in the flow through and wash fraction. A linear gradient of pH 6 to 3 was applied.

FIG. 37 show that the majority of goat milk proteins do not bind to the protein A resin and are harvested in the flow through. The goat milk proteins (including goat IgG) loaded and bound at pH 6 were harvested in the first part of elution at pH >4.8. FIG. 38 show that all monoclonal heterologous antibody is eluted in the second part of elution at pH <4.8 and more exactly at pH ~4.0.

The comparison of these results obtained with the results of the example 4.2.a (linear gradient) confirms that goat milk proteins (including goat IgG) and heterologous antibody can be purified using different protein A resins.

2. Step Gradient

In order to better separate goat IgG and heterologous antibody, elution was performed using 3 steps of pH. The loading sample is the same as above (purification on MabSelect PrismA resin by linear gradient): whey goat milk containing ~1 g/l heterologous antibody.

Purification of heterologous antibody was carried out by affinity chromatography using 5 ml cartridge containing protein-A (HiTrap MabSelect PrismA, GE Healthcare). Run was performed as follows: 2 column volumes (CV) of the sample were loaded at a flow rate of 1 ml/min on cartridge equilibrated in 50 mM sodium acetate, 50 mM NaCl at pH 6.0. Cartridge was washed with 10 CV at a flow rate of 2.5 ml/min with equilibration buffer. A first elution was performed using 5 CV of 50 mM sodium acetate, 100 mM NaCl at pH 4.7 at a flow rate of 2.5 ml/min. The second elution was performed using 5 CV of 100 mM glycine at pH 3.0 at a flow rate of 2.5 ml/min. The heterologous antibody eluted at pH 3 are neutralized using 1M Tris-HCl at pH 8.5. Chromatogram is reported in FIG. 39.

Monoclonal heterologous antibody concentration was measured by bio-layer interferometry (BLI). Recovery yield of mAb (%) was calculated using the following equation: $(Cf \times Vf)/(Ci \times Vi) \times 100$ (with Cf=concentration of mAb in the final product (g/l), Vf=volume of the final product (l), Ci=concentration of mAb in the loading sample (g/l), Vi=volume of the loading sample (l)). Goat IgG were visualized by western Blot (FIG. 40).

TABLE 10

Description of the samples loaded on the gels of FIG. 40. The marker is PageRuler ™ Plus Prestained Protein Ladder, 10 to 250 kDa (ThermoFisher # 26619)

| well | Loading volume (μl) | Loading sample on gel | Sample from | Total dilution of the loading sample |
|---|---|---|---|---|
| 1 | 10 | Loading sample | Step & linear | 1/2 |
| 2 | 10 | Flow through | Linear gradient | 1/2 |
| 3 | 10 | Peak pH >4.8 | Linear gradient | 1/2 |
| 4 | / | / | / | |
| 5 | 10 | Pic ph <4.8 | Linear gradient | 1/2 |
| 6 | 10 | Protein Molecular Weight Marker | / | / |
| 7 | 10 | Flow through | Step gradient | 1/2 |
| 8 | 10 | Peak at pH = 4.78 | Step gradient | 1/2 |
| 9 | | | | |
| 10 | 10 | Peak at pH = 3 | Step gradient | 1/2 |
| 11 | / | | | |
| 12 | 10 | Goat serum (WB control) | / | 1/1000 |
| 13 | 10 | Goat serum (WB control) | / | 1/10000 |

Figure 39:
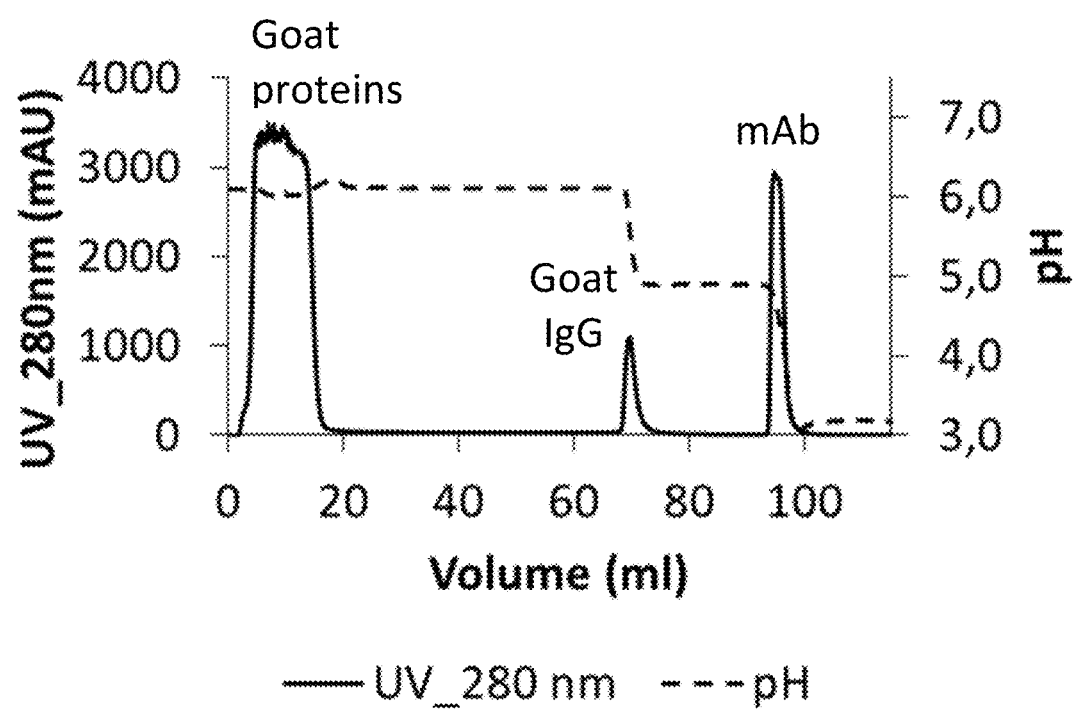
FIG. 39: Chromatogram of the purification by affinity chromatography using the MabSelect PrismA resin. The absorbance at 280 nm at the outlet of the column and the pH are represented respectively by lines as indicated. The sample containing heterologous antibody was loaded onto the column and then the column was washed with the equilibration buffer at pH 6. Proteins which were not bound to the column were recovered in the flow through and wash fraction. Step gradients at pH 4.7 and 3 were applied.

Under the experimental conditions, the chromatogram shows that goat proteins loaded were mainly harvested in the flow through (FIG. 39). Whether for step gradient or linear gradient purification, goat IgG western blot analysis show that goat antibodies loaded were mainly harvested at pH ≥4.7 (FIG. 40). Conversely, heterologous antibody having high affinity for protein-A resin was weakly lost in the flow through, washes and at pH ≥4.7. BLI reveals that more than 80% of the monoclonal antibody loaded was harvested in elution at pH 3 (peak retention volume=121 ml). The purified heterologous antibody contains residual goat IgG that the purification is carried out by step gradient or linear gradient (FIG. 40).

These results confirm that goat milk proteins (including goat IgG) and heterologous antibody can be purified using different protein A resins.

3. Dynamic Binding Capacity

Figure 41:
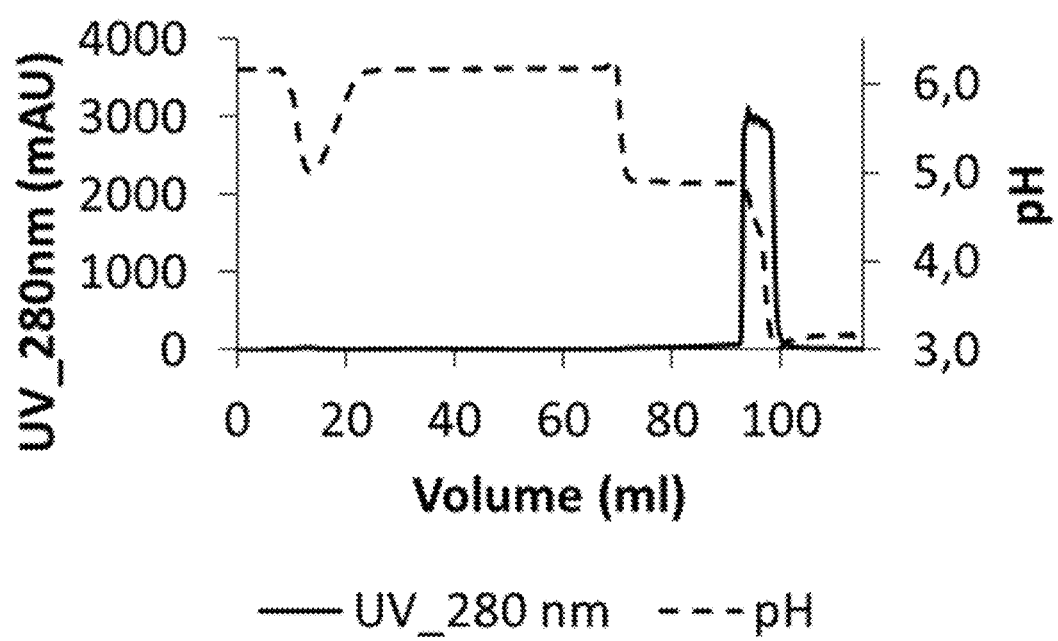
FIG. 41: Chromatogram of the purification by affinity chromatography using the MabSelect PrismA resin. 140 mg of heterologous antibody were loaded onto the 5 ml column and then the column was washed with the equilibration buffer at pH 6. Step gradients at pH 4.7 and 3 were applied. The absorbance at 280 nm at the outlet of the column and the pH are represented respectively by lines as indicated.

Purification of heterologous antibody was carried out by affinity chromatography using 5 ml cartridge containing protein-A (HiTrap MabSelect PrismA, GE Healthcare). Run was performed as follows: 2 column volumes (CV) of the 14 g/l heterologous antibody in 50 mM acetate at pH 5 were loaded at a flow rate of 0.8 ml/min on cartridge equilibrated in 50 mM sodium acetate, 500 mM NaCl at pH 6.0. Cartridge was washed with 10 CV at a flow rate of 2.5 ml/min with equilibration buffer. A first pH step was performed using 5 CV of 50 mM sodium acetate, 100 mM NaCl at pH 4.7 at a flow rate of 2.5 ml/min. The second elution was performed using 5 CV of 100 mM glycine at pH 3.0 at a flow rate of 2.5 ml/min. Fractions collected during elution at pH 3 (retention volume from 92 to 103 ml) are neutralized using 1M Tris-HCl at pH 8.5. Chromatogram is reported in FIG. 41. Peaks are integrated with the help of the Unicorn software.

28 mg of heterologous antibody/ml of resin were loaded. Antibody was weakly recovered in the flow through and the step gradient at pH 4.7 (peak area from 5 ml to 16 ml and from 71 ml to 92 ml are 149 mAU*ml and 295 mAU*ml respectively). The heterologous antibody was mainly eluted in the step gradient at pH 3 (peak area from 92 ml to 103 ml is 17225 mAU*ml). The DBC is estimated at 26 mg heterologous antibody/ml of PrismA resin under the purification conditions.

4. Loading pH

Purification of heterologous antibody was carried out by affinity chromatography using 5 ml cartridge containing protein-A (HiTrap MabSelect PrismA, GE Healthcare). Run was performed as follows: 2 column volumes (CV) of the sample (1 g/l heterologous antibody in the equilibration buffer) were loaded at a flow rate of 1 ml/min on cartridge equilibrated in 50 mM sodium acetate, 100 mM NaCl at pH 4.7. Cartridge was washed with 10 CV at a flow rate of 2.5 ml/min with equilibration buffer. Four pH steps were performed at a flow rate of 2.5 ml/min using 5 CV of 50 mM sodium acetate, 100 mM NaCl at pH 4.5, 5 CV of 50 mM sodium acetate, 100 mM NaCl at pH 4.3, 5 CV of 50 mM sodium acetate, 100 mM NaCl at pH 3.5 and 5 CV of 100 mM sodium acetate at pH 3.0 respectively. The heterologous antibody eluted at pH 3.5 are neutralized using 1M Tris-HCl at pH 8.5. Chromatogram is reported in FIG. 42.

Figure 42:
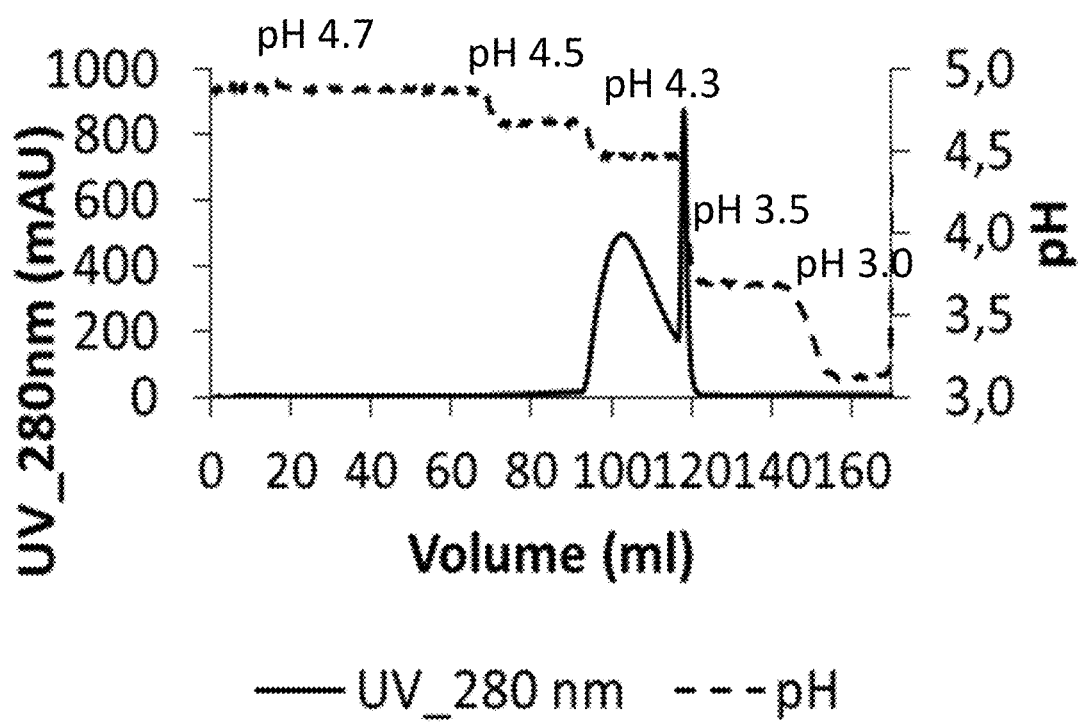
FIG. 42: Chromatogram of the purification by affinity chromatography. The absorbance at 280 nm at the outlet of the column and the pH are represented respectively by lines as indicated. The heterologous antibody in buffer was loaded onto the column and then the column was washed with the equilibration buffer at pH 4.7. Then, step gradients at pH 4.5, 4.3, 3.5 and 3 were applied.

Absorbance at 280 nm of FIG. 42 shown that the heterologous antibody is bound on the protein A resin at pH ≥4.5. According to this result, the sample could be loaded at pH ≥4.5. At pH 4.3, the heterologous antibody was released progressively from the matrix. At pH 3.5, the elution of heterologous antibody is complete. At pH 3.0, no peak is observed. The heterologous antibody could also be eluted at pH 3.5.

Figure 46A:
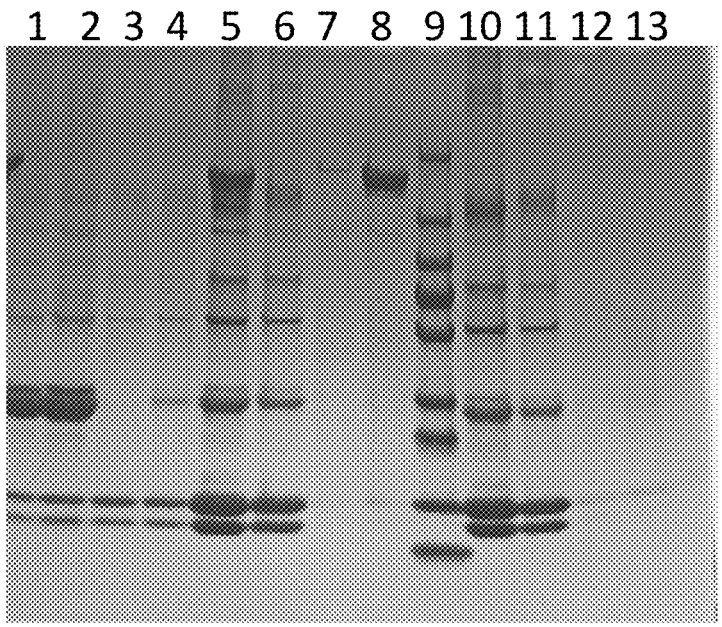
FIGS. 46A and 46B: SDS-PAGE analysis (FIG. 46A) and corresponding Goat IgG western blot analysis (FIG. 46B) of the heterologous antibody purification (not reduced conditions). The description of the samples loaded is reported in Table 11.
Figure 46B:
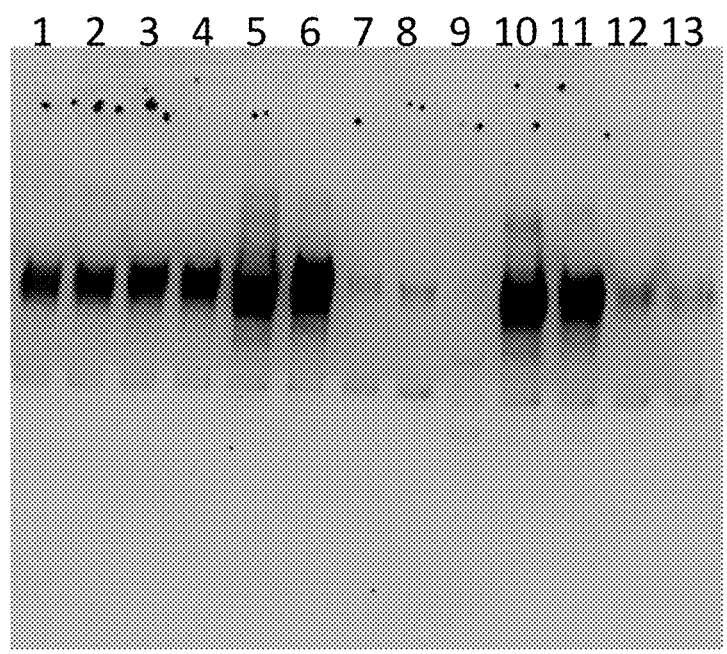

To confirm the previous result, two loading samples were prepared as follows: Whole fresh goat milk was heated at 50° C. then centrifuged at 3000 g for 10 min. The flask was cooled in order to solidify the fat. The cream at the top of the flask was removed. For the first sample, skimmed milk caseins were precipitated at 20° C. by addition of HCl 1M until pH 4.3 and for the second sample, skimmed milk caseins were precipitated at 20° C. by addition of HCl 1M until pH 4.5. Precipitated caseins were removed by centrifugation at 10000 g for 20 min at 20° C. NaCl is added to the supernatant to a conductivity of 50 mS/cm. The mixture (supernatant+NaCl) was filtered through 0.22 μm before the loading on the chromatography matrix. The milk samples were analysed by SDS-PAGE and goat IgG western Blot (FIG. 46).

Figure 43:
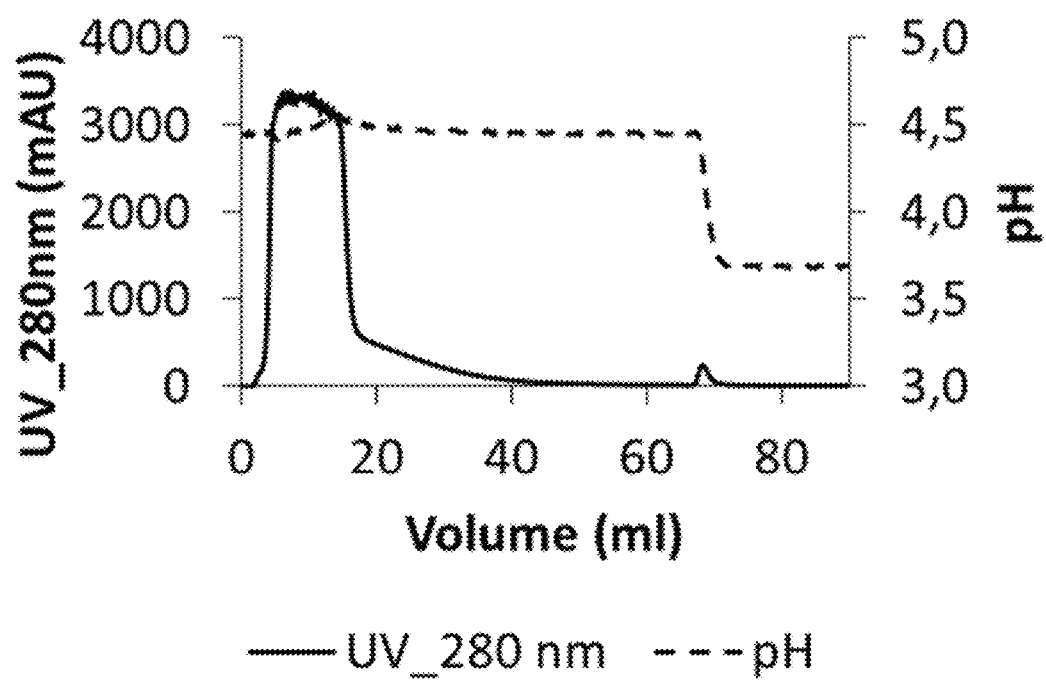
FIG. 43: Chromatogram of the purification by affinity chromatography. The absorbance at 280 nm at the outlet of the column and the pH are represented respectively by lines as indicated. The sample containing heterologous antibody was loaded onto the column and then the column was washed with the equilibration buffer at pH 4.3. Elution was performed at pH 3.5.

Purification of heterologous antibody was carried out by affinity chromatography using 5 ml cartridge containing protein-A (HiTrap MabSelect PrismA, GE Healthcare). Run was performed as follows: For the first loading sample, 2 column volumes (CV) of the loading sample at pH 4.3 containing canine monoclonal heterologous antibody (~1 mg/ml) were loaded at a flow rate of 1 ml/min on cartridge equilibrated in 50 mM sodium acetate, 100 mM NaCl at pH 4.3. Cartridge was washed with 10 CV at a flow rate of 2.5 ml/min with equilibration buffer. The elution step was performed at a flow rate of 2.5 ml/min using 5 CV of 50 mM sodium acetate, 100 mM NaCl at pH 3.5. The heterologous antibody eluted at pH 3.5 are neutralized using 1M Tris-HCl at pH 8.5. Chromatogram is reported in FIG. 43. For the second loading sample, 2 column volumes (CV) of the loading sample at pH 4.5 containing canine monoclonal heterologous antibody (~1 mg/ml) were loaded at a flow rate of 1 ml/min on cartridge equilibrated in 50 mM sodium acetate, 100 mM NaCl at pH 4.5. Cartridge was washed with 10 CV at a flow rate of 2.5 ml/min with equilibration buffer. The elution step was performed at a flow rate of 2.5 ml/min using 5 CV of 50 mM sodium acetate, 100 mM NaCl at pH 3.5. The heterologous antibody eluted at pH 3.5 are neutralized using 1M Tris-HCl at pH 8.5. Chromatogram is reported in FIG. 44.

A negative control (goat milk without heterologous antibody) is treated and purified according to the same parameters as the second sample (at pH 4.5). The chromatogram of the purification of the negative control is reported in FIG. 45. Samples were analysed by SDS-PAGE and goat IgG western Blot (FIG. 46).

TABLE 11

Description description of the samples loaded on the gels of FIG. 46. The marker is PageRuler ™ Plus Prestained Protein Ladder, 10 to 250 kDa (ThermoFisher # 26619)

| well | Loading volume (μl) | Loading sample on gel | Sample from | Total dilution of the loading sample |
|---|---|---|---|---|
| 1 | 10 | Whole milk | Milk treatment | 1/20 |
| 2 | 10 | Skimmed milk | Milk treatment | 1/20 |
| 3 | 10 | Whey at pH 4.3 | Milk treatment | 1/20 |
| 4 | 10 | Whey at pH 4.5 | Milk treatment | 1/20 |
| 5 | 10 | Loading sample at pH 4.5 | Loading sample at pH 4.5 + mAb | 1/2 |
| 6 | 10 | Flow through | Loading sample at pH 4.5 + mAb | 1/2 |
| 7 | 10 | wash | Loading sample at pH 4.5 + mAb | 1/2 |
| 8 | 10 | Elution at pH 3.5 | Loading sample at pH 4.5 + mAb | 1/2 |
| 9 | 10 | Protein Molecular Weight Marker | / | / |
| 10 | 10 | Loading sample at pH 4.5 | Loading sample at pH 4.5 (CTRL-) | 1/2 |
| 11 | 10 | Flow through | Loading sample at pH 4.5 (CTRL-) | 1/2 |
| 12 | 10 | wash | Loading sample at pH 4.5 (CTRL-) | 1/2 |
| 13 | 10 | Elution at pH 3.5 | Loading sample at pH 4.5 (CTRL-) | 1/2 |

Figure 44:
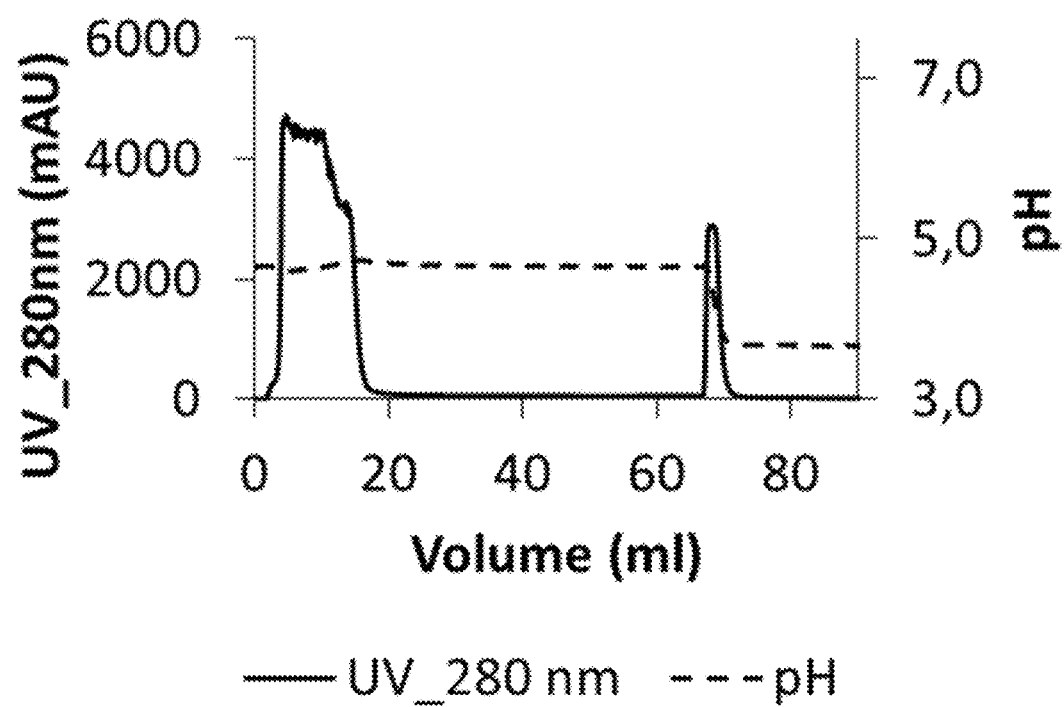
FIG. 44: Chromatogram of the purification by affinity chromatography. The absorbance at 280 nm at the outlet of the column and the pH are represented respectively by lines as indicated. The sample containing heterologous antibody was loaded onto the column and then the column was washed with the equilibration buffer at pH 4.5. Elution was performed at pH 3.5.

SDS-PAGE analysis reveals that caseins precipitate completely at pH 4.3 whereas at pH 4.5 there are caseins visible on gel (MW caseins=19-25 kDa) (FIG. 46). The low area of elution peak in FIG. 43 (peak retention volume≈68 ml) reveals that when the sample is loaded at pH 4.3, the heterologous antibody is very weakly bound to the protein A resin. These results are consistent with previous results (FIG. 42). In our purification conditions, the sample is preferably loaded at pH >4.3. On the contrary, when the sample is loaded at pH 4.5, the heterologous antibody is well bound to the protein A resin (FIG. 44). SDS-PAGE and goat IgG western blot analysis show that goat milk proteins (including Goat IgG) loaded are harvested in the flow through and the heterologous antibody (MW 150 kDa) is mainly harvested in the elution at pH 3.5 with significant purity. Monoclonal heterologous antibody concentration was measured by bio-layer interferometry (BLI). mAb recovery yield (%) was calculated using the following equation: $(Cf \times Vf)/(Ci \times Vi) \times 100$ (with Cf=concentration of mAb in the final product (g/l), Vf=volume of the final product (l), Ci=concentration of mAb in the loading sample at pH 4.5 (g/l), Vi=volume of the loading sample at pH 4.5 (l)). BLI reveals that more than 80% of the monoclonal antibody loaded were harvested in the elution at pH 3.5.

Figure 45:
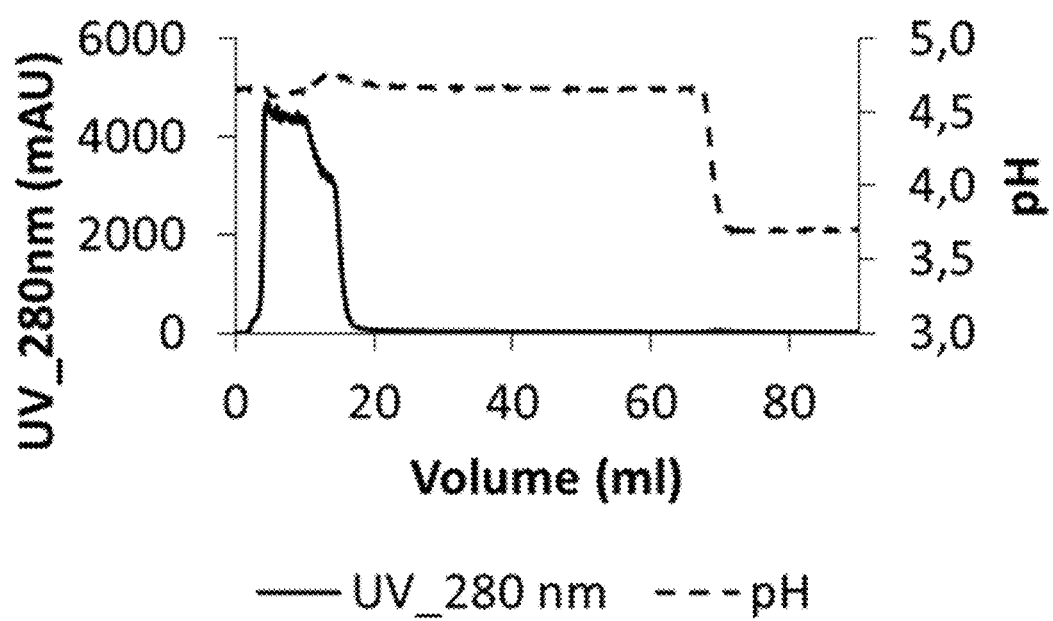
FIG. 45: Chromatogram of the purification by affinity chromatography. The absorbance at 280 nm at the outlet of the column and the pH are represented respectively by lines as indicated. The sample without heterologous antibody was loaded onto the column and then the column was washed with the equilibration buffer at pH 4.5. Proteins which were not bound to the column were recovered in the flow through and wash fractions. Step gradient at pH 3.5 was applied.

Chromatogram of the purification of the negative control shows a small peak area for the elution at pH 3.5 which indicates that residual goat proteins are eluted in step gradient at pH 3.5 (peak retention volume=~70 ml, FIG. 45). The SDS-PAGE analysis proves that this amount of residual proteins is small and negligible compared to purified heterologous antibody (FIG. 46). Goat IgG Western blot indicates that residual goat IgG is present in the purified heterologous antibody.

These previous examples indicate that the sample could be loaded on the protein A resin at pH 4.5. The main advantages are: i) have only two pH steps (pH 4.5 and pH 3.5) and ii) do not bind goat IgG on the resin (therefore increase its dynamic binding capacity for heterologous antibodies).

Example 9: Salt Concentration in Loading Sample

Loading samples were prepared as follows: Whole fresh goat milk was heated at 50° C. then centrifuged at 3000 g for 10 min. The flask was cooled in order to solidify the fat. The cream at the top of the flask was removed. Skimmed milk caseins were precipitated at 20° C. by addition of HCl 1M until pH 4.3. Precipitated caseins were removed by centrifugation at 10000 g for 20 min at 20° C. For the first sample, NaCl is added to the supernatant to a conductivity of 50 mS/cm and for the second sample, nothing is added to the supernatant. The mixture (supernatant+NaCl) or supernatant were filtered through 0.22 μm before the loading on the chromatography matrix.

Purifications of heterologous antibody were carried out by affinity chromatography using 5 ml cartridge containing protein-A (Praesto AP Minichrom (purolite)) using the same conditions for the first and second sample. Runs were performed as follows: 6 column volumes (CV) of the loading sample containing canine monoclonal heterologous antibody (~1 mg/ml) were loaded at a flow rate of 1 ml/min on cartridge equilibrated in 50 mM sodium acetate, 500 mM NaCl at pH 6.0. Cartridge was washed with 10 CV at a flow rate of 4 ml/min with equilibration buffer. A second wash was performed using 5 CV of 50 mM sodium acetate, 100 mM NaCl at pH 4.7 at a flow rate of 4 ml/min. The elution was performed using 5 CV of 100 mM acetate at pH 3.0 at a flow rate of 4 ml/min. The heterologous antibody eluted at pH 3.0 were neutralized using 1M Tris-HCl at pH 8.5. Chromatograms are reported in FIG. 47 and FIG. 48. Peaks are integrated with the help of the Unicorn software.

Figure 47:
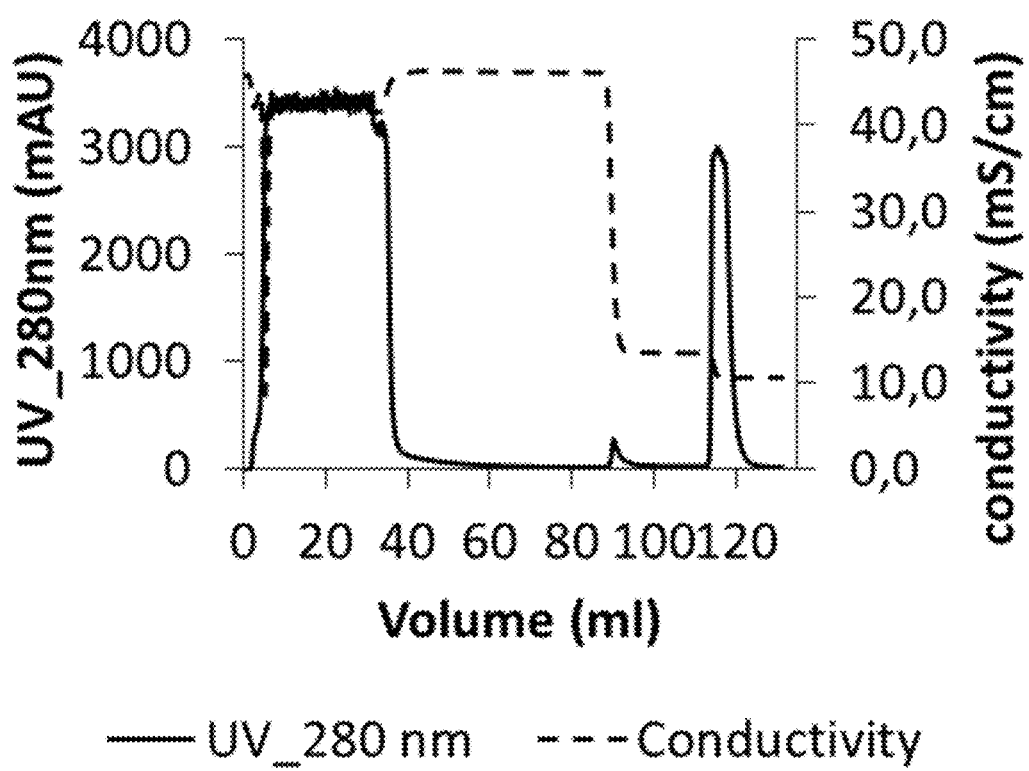
FIG. 47: Chromatogram of the purification by affinity chromatography using the Praesto AP Minichrom resin. The absorbance at 280 nm at the outlet of the column and the conductivity are represented respectively by lines as indicated. The sample containing heterologous antibody+NaCl was loaded onto the column and then the column was washed with the equilibration buffer at pH 6. Proteins which were not bound to the column were recovered in the flow through and wash fractions. Step gradients at pH 4.7 and 3 were applied in order to harvest the goat IgG (peak retention volume=90 ml) and heterologous antibody (peak retention volume=116 ml) respectively.
Figure 48:
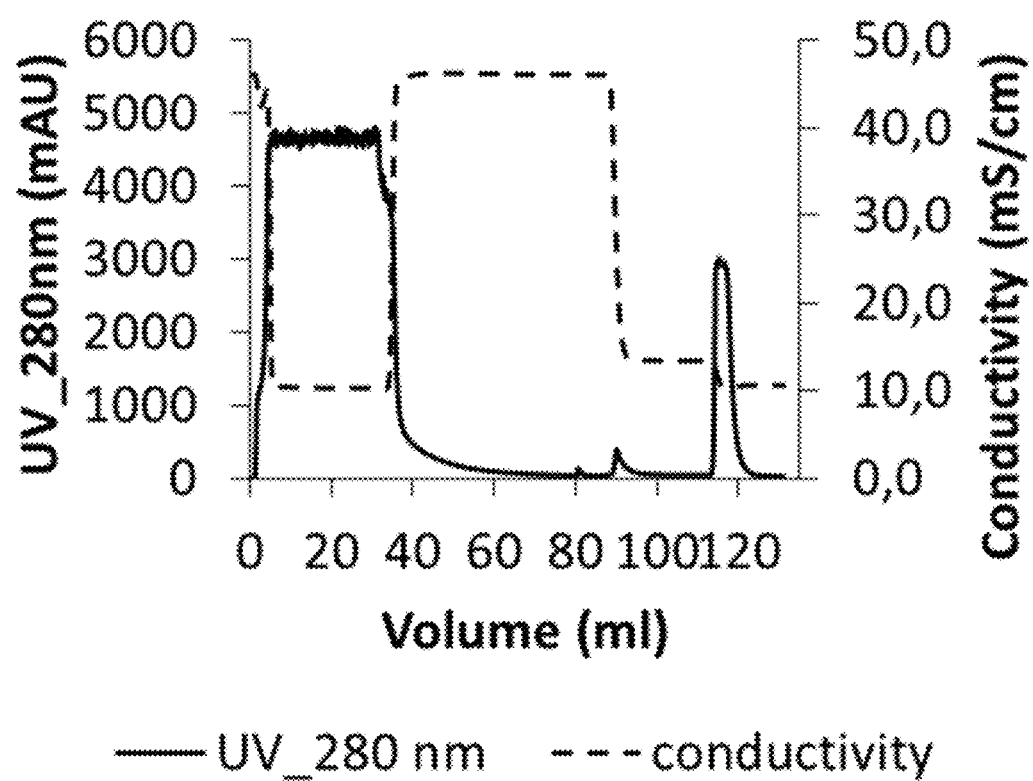
FIG. 48: Chromatogram of the purification by affinity chromatography using the Praesto AP Minichrom resin. The absorbance at 280 nm at the outlet of the column and the conductivity are represented respectively by lines as indicated. The sample containing heterologous antibody (without NaCl) was loaded onto the column and then the column was washed with the equilibration buffer at pH 6. Proteins which were not bound to the column were recovered in the flow through and wash fractions. Step gradients at pH 4.7 and 3 were applied in order to harvest the goat IgG (peak retention volume=90 ml) and heterologous antibody (peak retention volume=115 ml) respectively.

Comparison of the 280 nm absorbance of the chromatograms of FIG. 47 and FIG. 48 shows that if NaCl is added to the loading sample, proteins that have no affinity for the resin are more quickly recovered in the flow through. Indeed, the baseline for the absorption at 280 nm is reached more quickly when the sample is loaded with NaCl.

The areas of the elution peaks at pH 3.0 (retention volume≈115 ml) of the chromatograms of FIG. 47 and FIG. 48 are highly similar, which reveals that if the sample is loaded with NaCl there is no difference in the recovery yield of the heterologous antibody. SDS-PAGE analysis shows that the heterologous antibody eluted at pH 3 has a significant purity whatever the load conditions used (with or without NaCl) (data not shown).

The addition of NaCl in loading sample is advantageous in order to decrease the washing volumes (for example 10 CV to 5 CV) while maintaining the same yield and purity of the heterologous antibody after the chromatography.

The invention claimed is:

1. A method for purifying antibodies, the method comprising:
 providing caprine whey comprising a monoclonal heterologous antibody;
 contacting the caprine whey with a protein A containing matrix;
 separating the protein A containing solid matrix from the caprine whey; and
 eluting the heterologous antibody from the protein A containing matrix;
 wherein, prior to eluting the heterologous antibody, endogenous caprine antibodies are eluted at a pH which is higher than the pH for eluting the heterologous antibodies; and
 wherein
 endogenous caprine antibodies are eluted at a pH ranging from 4.0 to 5.0; and/or
 heterologous antibodies are eluted at a pH ranging from 2.0 to 4.0; and/or
 the protein A containing matrix and/or the caprine whey is equilibrated to a pH ranging from 6 to 7 before contacting the caprine whey with the protein A containing matrix.

2. The method according to claim 1, further comprising:
 providing caprine milk comprising the heterologous antibody;
 removing casein from the caprine milk so as to provide the caprine whey.

3. The method according to claim 2, further comprising: skimming the caprine milk.

4. The method according to claim 1, wherein the method comprises chromatography.

5. The method according to claim 1, wherein the protein A containing matrix and/or the caprine whey is equilibrated to a pH ranging from 5 to 8, before contacting the caprine whey with the protein A containing matrix.

6. The method according to claim 1, wherein the heterologous antibody is not a caprine antibody.

7. The method according to claim 1, wherein the heterologous antibody is a murine, bovine, porcine, canine, feline, or equine antibody.

8. The method according to claim 1, wherein the heterologous antibody is an IgG antibody.

9. The method according to claim 1, wherein the whey comprises native endogenous caprine antibodies.

10. The method according to claim 1, wherein removing casein from the caprine milk comprises:
 adjusting the pH of the caprine milk to a pH ranging from 3.5 to 5.0, and removing precipitated casein.

11. The method according to claim 3, wherein skimming the caprine milk comprises;
 heating the caprine milk to a temperature ranging from 30 to 60° C., and removing fat from the heated caprine milk.

12. The method according to claim 4, wherein the chromatography is packed bed chromatography.

13. The method according to claim 10, wherein adjusting the pH of the caprine milk comprises adjusting the pH of the caprine milk to a pH ranging from 4.0 to 4.5.

14. The method according to claim 11, wherein heating the caprine milk comprises heating the caprine milk to a temperature ranging from 45 to 55° C.

* * * * *